US008124842B2

(12) United States Patent
Frohberg et al.

(10) Patent No.: US 8,124,842 B2
(45) Date of Patent: Feb. 28, 2012

(54) PLANTS HAVING AN INCREASED CONTENT OF AMINO SUGARS

(75) Inventors: Claus Frohberg, Kleinmachnow (DE); Bernd Essigmann, Berlin (DE)

(73) Assignee: Bayer Cropscience AG, Monheim Am Rhein (DE)

( * ) Notice: Subject to any disclaimer, the term of this patent is extended or adjusted under 35 U.S.C. 154(b) by 551 days.

(21) Appl. No.: 12/089,292

(22) PCT Filed: Oct. 5, 2006

(86) PCT No.: PCT/EP2006/009776
§ 371 (c)(1),
(2), (4) Date: Sep. 18, 2008

(87) PCT Pub. No.: WO2007/039317
PCT Pub. Date: Apr. 12, 2007

(65) Prior Publication Data
US 2009/0304889 A1    Dec. 10, 2009

(30) Foreign Application Priority Data

Oct. 5, 2005 (EP) ................................. 05090279
Sep. 22, 2006 (EP) ................................. 06090177

(51) Int. Cl.
*C12N 15/29* (2006.01)
*C12N 15/63* (2006.01)
*C12N 15/82* (2006.01)
*C12N 15/09* (2006.01)
*A01H 5/00* (2006.01)
*A01H 5/10* (2006.01)

(52) U.S. Cl. ..... 800/288; 800/278; 800/284; 435/320.1; 435/468; 536/23.1; 536/23.2; 536/23.5; 536/23.7

(58) Field of Classification Search ........................ None
See application file for complete search history.

(56) References Cited

FOREIGN PATENT DOCUMENTS

| WO | WO 00/11192    | 3/2000 |
| WO | WO 2006/032538 | 3/2006 |
| WO | WO 2005/012529 | 5/2006 |
| WO | WO 2007/039314 | 4/2007 |
| WO | WO 2007/039315 | 4/2007 |
| WO | WO 2007/039316 | 4/2007 |
| WO | WO 2007/039317 | 4/2007 |

OTHER PUBLICATIONS

Milewski (Jun. 3, 2002) "Glucosamine-6-phosphate Synthase—the multi-facets enzyme." Biochimica et Biophysica Acta 1597(2): 173-192.

*Primary Examiner* — Brent T Page
*(74) Attorney, Agent, or Firm* — Hunton & Williams, LLP

(57) ABSTRACT

The present invention relates to plant cells and plants having an increased content of N-acetylated glucosamine derivatives. Furthermore, the present invention relates to plant cells and plants which synthesize glucosaminoglycans. The present invention also provides processes for producing said plants and compositions comprising said plant cells.

41 Claims, No Drawings

PLANTS HAVING AN INCREASED CONTENT OF AMINO SUGARS

CROSS-REFERENCE TO RELATED APPLICATIONS

This application is the U.S. National Stage filing of International Application No. PCT/EP2006/09776, filed Oct. 5, 2006, which claims priority to EP 05090279.0, filed Oct. 5, 2005; U.S. Provisional Patent Application No. 60/725,388, filed Oct. 11, 2005; and EP 06090177.4, filed Sep. 22, 2006, the disclosures of each of which are hereby incorporated by reference.

BACKGROUND OF THE INVENTION (i) Field of the Invention

The present invention relates to plant cells and plants having an increased content of N-acetylated glucosamine derivatives. Furthermore, the present invention relates to plant cells and plants synthesizing glucosaminoglycans. The present invention also provides processes for producing said plants and compositions comprising said plant cells.

(ii) Description of the Related Art

The amino sugar glucosamine, glucosamine derivatives and polymers comprising glucosamine derivatives are used, inter alia, as food supplements for the prophylaxis of joint disorders in animals and man. In the medical field, too, some glucosamine derivative-containing polymers are used for treating disorders.

WO 06 032538 describes transgenic plants which had been transformed with nucleic acid molecules coding for hyaluronan synthases. The synthesis of hyaluronan in the plants in question could be demonstrated unambiguously.

WO 98 35047 (U.S. Pat. No. 6,444,878) describes a metabolic path for the synthesis of GlcNAc in plant cells where glucosamine is converted by a number of successive enzymatically catalyzed reaction steps with formation of the metabolites GlcNAc, N-acetylglucosamine 6-phosphate, N-acetylglucosamine 1-phosphate into UDP-GlcNAc. A metabolic path which was described as an alternative for plants comprises the conversion of fructose 6-phosphate and glutamine into glucosamine 6-phosphate which is then converted by a number of successive enzymatically catalyzed reaction steps with formation of the metabolites glucosamine 1-phosphate and N-acetylglucosamine 1-phosphate into UDP-GlcNAc. The conversion of fructose 6-phosphate and glutamine into glucosamine 6-phosphate is catalyzed by a protein having the activity of a glutamine:fructose 6-phosphate amidotransferase (GFAT) (Mayer et al., 1968, Plant Physiol. 43, 1097-1107). Relatively high concentrations of glucosamine 6-phosphate are toxic for plant cells (WO 98 35047).

WO 00 11192 describes the endosperm-specific overexpression of a nucleic acid molecule from corn coding for a protein having the enzymatic activity of a plant GFAT in transgenic corn plants with the aim of synthesizing a cationic starch having 2-amidoanhydroglucose molecules in plants. The metabolic path described which, according to the description of WO 00 11192, should result in the incorporation of 2-aminoanhydroglucose into the starch, comprises inter alia the incorporation of UDP-glucosamine by starch and/or glycogen synthases into the starch. It was possible to demonstrate increased amounts of UDP-glucosamine in the flour of endosperm of the transgenic corn plants in question overexpressing a nucleic acid molecule coding for a protein having the enzymatic activity of a plant GFAT translationally fused with a plastid signal peptide. When the protein having the enzymatic activity of a GFAT was expressed without signal peptide, it was possible to demonstrate an increased amount of glucosamine 1-phosphate in the corresponding flour from corn endosperm tissue. It was not possible to detect cationic starch or increased amounts of N-acetylated glucosamine derivatives, such as, for example, UDP-GlcNAc or N-acetylglucosamine 6-phosphate, in the transgenic plants.

The amino sugar beta-D-glucosamine (glucosamine) and/or derivatives of glucosamine are components of various polymers (glucosaminoglycans) which, inter alia, are essential components of the exoskeleton of arthropods, the extracellular matrix of mammals or the exopolysaccharides of some bacterial microorganisms.

Thus, for example, N-acetyl-D-glucos-2-amine (N-acetylglucosamine, GlcNAc) is a glucosamine derivative acetylated at the nitrogen atom. GlcNAc is, for example, a molecular building block of hyaluronan (beta-1,4-[glucuronic acid beta-1,3-GlcNAc]$_n$), which is an essential component of the synovial fluid.

In the medical field, hyaluronan-containing products are currently used for the intra-articular treatment of arthrosis and as ophthalmics used for eye surgery. Derivatized cross-linked hyaluronan is used for treating joint disorders (Fong Chong et al., 2005, Appl Microbiol Biotechnol 66, 341-351). In addition, hyaluronan is a component of some rhinologics which, for example in the form of eye drops and nasalia, serve to moisten dry mucous membranes. Hyaluronan-containing solutions for injection are used as analgesics and antirheumatics. Patches comprising hyaluronan or derivatized hyaluronan are employed in wound healing. As dermatics, hyaluronan-containing gel implants are used for correcting skin deformations in plastic surgery. In cosmetic surgery, hyaluronan preparations are among the suitable skin filler materials. By injecting hyaluronan, for a limited period of time, it is possible to smooth wrinkles or to increase the volume of lips.

In cosmetic products, in particular in skin creams and lotions, hyalauronan is frequently used as a moisturizer by virtue of its high water-binding capacity. Furthermore, hyaluronan-containing preparations are sold as so-called neutraceuticals (food supplements) which can also be used in animals (for example dogs, horses) for the prophylaxis and alleviation of arthrosis.

The catalysis of the hyaluronan synthesis is effected by a single membrane-integrated or membrane-associated enzyme, i.e. hyaluronan synthase (DeAngelis, 1999, CMLS, Cellular and Molecular Life Sciences 56, 670-682). Hyaluronan synthase catalyzes the synthesis of hyaluronan from the substrates UDP-glucuronic acid (UDP-GlcA) and UDP-N-acetylglucosamine (UDP-GlcNAc).

Hyaluronan used for commercial purposes is currently isolated from animal tissues (roostercombs) or prepared fermentatively using bacterial cultures.

Proteoglycans, a class of glycoproteins, are, inter alia, an essential component of cartilage and have, attached to a core protein, glucosaminoglycans composed of repetitive disaccharide units. The repetitive disaccharide units for their part are covalently attached to the core protein via a characteristic carbohydrate binding sequence. Depending on the composition of the disaccharide units, a distinction is made, inter alia, of the glucosaminoglycans heparan/heparin sulfate, keratan sulfate and chondroitin/dermatan sulfate, whose disaccharide units each contain a molecule which is either glucosamine or a glucosamine derivative. In these substances, sulfate groups are introduced at various atoms or substituents of the disaccharide units, so that the respective substances mentioned are not uniform polymers but polymer groups summarized under the respective generic term. Here, the individual molecules of the polymer groups in question may differ both in the degree of sulfation and in the position of the monomers containing sulfate groups.

The synthesis of the disaccharide chain of the chondroitin/dermatan ([beta-1,4]-[glucuronic acid beta-1,4-N-acetylgalactosamine]$_n$) is catalyzed by a chondroitin synthase starting with UDP-GlcA and UDP-N-acetylgalactosamine, an epimer of UDP-GlcNAc (Kitagawa et al., 2001, J Biol Chem 276 (42), 38721-38726). The glucuronic acid molecules of chondroitin can be converted by an epimerase into iduronic acid. If more than 10% of the glucuronic acid molecules are present as iduronic acid, the polymer is referred to as dermatan. The introduction of the sulfate groups in various positions of the disaccharide chain of the chondroitin or the dermatan is then catalyzed by further enzymes, resulting in chondroitin/dermatan sulfate. Here, the degree of sulfation may differ from molecule to molecule.

For some time, chondroitin sulfate has been considered as a potential active compound for treatment of osteoarthritis (Clegg et al., 2006, The New England Journal of Medicine 354(8), 795-808).

The synthesis of the disaccharide chain of heparin/heparan (heparosan) ([alpha-1,4]-[glucuronic acid beta-1,4-glucosamine]$_n$ or [alpha-1,4]-[iduronic acid alpha-1,4-glucosamine]$_n$) is catalyzed by a heparin/heparosan synthase from UDP-GlcA and UDP-GlcNAc (DeAngelis und White, 2004, J. Bacteriology 186(24), 8529-8532). The glucuronic acid molecules of the heparin/heparosan can be converted by an epimerase into iduronic acid. The introduction of the sulfate groups in various positions of the disaccharide chain of the heparosan is then catalyzed by further enzymes, giving rise to heparin sulfate or heparan sulfate. Heparin sulfate has a considerably higher substitution by sulfate groups than heparan sulfate. Heparin sulfate has about 90% iduronic acid molecules, whereas in the case of heparan sulfate the fraction of glucuronic acid molecules predominates (Gallagher et al., 1992, Int. J. Biochem 24, 553-560). As in the case of chondroitin/dermatan sulfate, in the case of heparin/heparan sulfate, too, the degree of sulfation may differ from molecule to molecule.

Heparin sulfate is used, inter alia, as an anticoagulant, for example for the prophylaxis and treatment of thromboses.

Chondroitin/dermatan sulfate and heparin/heparan sulfate are currently produced by isolation from animal tissues. Chondroitin sulfate is mainly isolated from bovine or shark cartilage, and heparin/heparan sulfate is isolated from porcine intestine or bovine lungs. Since the disaccharide chains of chondroitin/dermatan sulfate or heparin/heparan sulfate have no uniform sulfation pattern, it is difficult to obtain a uniform specific product. Accordingly, the products are always mixtures of molecules with varying degrees of sulfation.

The glucosaminoglycan chitin ([beta-1,4-GlcNAc]$_n$) is one of the main components of the cell wall of fungi and the exoskeleton of insects, millipedes, arachnids and crustaceans and is a polymer which is insoluble in water. The enzyme chitin synthase catalyzes the synthesis of chitin by linking UDP-GlcNAc (Merzendorfer and Zimoch, 2003, J. Experimental Biology 206, 4393-4412).

As a raw material source for isolating chitin, use is to date mainly made of crustaceans (prawns, crabs) and fungi, such as, for example, *Aspergillus* spec., *Penicillium* spec. *Mucor* spec. WO 03 031435 describes, for example, a method for preparing GlcNAc by fermentation of yeasts. Depending on the method by which chitin is isolated from the raw material source in question, chitin contains in addition to GlcNAc also its deacetylated form glucosamine as a building block. If more than 50% of the building blocks are GlcNAc, the polymer is referred to as chitin, whereas polymers comprising more than 50% of glucosamine are referred to as chitosan. These days, glucosamine or derivatives thereof, such as, for example, GlcNAc, are produced by degradation of chitin. Chitin may either be deacetylated first, resulting in the formation of chitosan, or be degraded directly, resulting in the formation of GlcNAc.

Chitin can be deacetylated enzymatically with the aid of chitin deacetylases (Kafetzopoulos et al., 1993, Pro. Natl. Acad. Sci. 90, 2564-2568) or by chemical deacetylation.

The degradation of chitin or of chitosan can also take place both enzymatically (for example using chitinases, glucanases, beta-N-acetylglucosaminidases), and by chemical hydrolysis.

The degradation of chitosan or the deacetylation of GlcNAc results in the formation of glucosamine.

A substantial disadvantage of all methods for preparing amino sugars by degradation of chitin consists in the fact that, owing to incomplete hydrolysis and/or incomplete deacetylation, what is obtained is not a uniform product but a mixture of various mono- and oligomers.

An alternative process for preparing glucosamine with the aid of recombinant microorganisms, in particular *Escherichia coli*, which does not require the degradation of chitin, is described in US 2002/0160459.

For some time, glucosamine and glucosamine-containing substances, too, have been considered as potential active compounds for the treatment of osteoarthritis (Clegg et al., 2006, The New England Journal of Medicine 354(8), 795-808). Glucosamine or glucosamine-containing substances are also present in many food supplements. Foods enriched with GlcNAc are described, for example, in US 2006/0003965.

As already described, glucosaminoglycans, such as, for example chondroitin sulfate, heparin/heparan sulfate or chitin are currently isolated from animal tissues. In addition to the substances desired in each case, these tissues also contain other glucosaminoglycans. The separation of the individual glucosaminoglycans, if a complete separation is possible at all, is difficult and complicated. Furthermore, the potential presence, in animal tissues, of pathogenic microorganisms and/or of other substances, such as, for example, the BSE pathogen or the bird flu pathogen, which may cause diseases in man, represent a problem when using glucosaminoglycans isolated from animal tissue. The use of medicinal preparations contaminated with animal proteins may, in the patient, result in unwanted immunological reactions of the body (for hyaluronan preparations, see, for example, U.S. Pat. No. 4,141,973), in particular if the patient is allergic to animal proteins.

A further problem during the isolation of glucosaminoglycans from animal tissues consists in the fact that the molecular weight of the glucosaminoglycans is frequently reduced during purification, since animal tissues also contain enzymes which degrade glucosaminoglycan.

Glucosamine or derivatives thereof isolated from crustaceans frequently contain substances (proteins) which may trigger an allergic reaction in man. Glucosamine or derivatives obtained from fungi may contain mycotoxins.

The amounts (yields) of glucosaminoglycans which can be obtained in satisfactory quality and purity from animal tissues are low (for example hyaluronan from roostercombs: 0.079% w/w, EP 0144019, U.S. Pat. No. 4,782,046), which means that large amounts of animal tissues have to be processed.

The production of glucosaminoglycans with the aid of fermentation of bacteria is associated with high costs, since the bacteria have to be fermented in sealed sterile containers under complicated controlled cultivation conditions (for hyaluronan, see, for example, U.S. Pat. No. 4,897,349). Furthermore, the amount of glucosaminoglycans which can be produced by fermentation of bacteria strains is limited by the existing production facilities. Here, it has also been taken into account that, owing to physical limitations, it is not possible to construct fermenters for relatively large culture volumes. In this context, mention may be made in particular of homogeneous mixing, required for efficient production, of fed-in substances (for example essential nutrient sources for bacteria, reagents for regulating the pH, oxygen) with the culture medium, which, if at all, can be ensured in large fermenters only with high technical expenditure.

Furthermore, substances prepared from animal raw materials are unacceptable for certain ways of life, such as, for example, veganism or for kosher food preparation.

Plants do not naturally produce glucosaminoglycans, such as, for example, hyaluronan, chitin, heparan/heparin sulfate, keratan sulfate or chondroitin/dermatan sulfate.

For the synthesis of glucosaminoglycans, it is necessary, inter alia, for sufficient amounts of acetylated glucosamine derivatives (in particular UDP-GlcNAc) and/or UDP-GlcA to be available as substrate for the respective enzymes involved in the synthesis. There is no information with regard to the amounts of N-acetylated glucosamines present in plant cells. WO 2005 035710 describes a process which allows the glucosamine content of plant material to be increased by drying. The highest glucosamine content in fresh, wet plant material was determined for chicory with 10 mg of glucosamine per 1 kg of fresh weight, which, at a molecular weight of 178 for glucosamine, corresponds to about 56 nmol of glucosamine per 1 gram fresh weight of plant material. WO 2005 035710 contains no information concerning the content of N-acetylated glucosamine derivatives in plants.

Furthermore, from the prior art described above, it is evident that the paths of glucosamine metabolism in plants have not yet been fully elucidated. In WO 00 11192, it was possible to generate plants by transformation with a nucleic acid molecule coding for a protein having the activity of a plant GFAT, which plants had an elevated content of glucosamine derivatives (UDP-glucosamine or glucosamine 1-phosphate); however, increased amounts of N-acetylated glucosamine derivatives were not found.

SUMMARY OF THE INVENTION

Accordingly, it is an object of the present invention to provide alternative sources of N-acetylated glucosamine derivatives and processes for preparing said alternative sources for N-acetylated glucosamine derivatives.

A first aspect of the present invention relates to plant cells or plants having a content of N-acetylated glucosamine derivatives of at least 2.50 µmol per gram of fresh weight, preferably of at least 5.00 µmol per gram of fresh weight, particularly preferably of at least 10.00 µmol per gram of fresh weight, very particularly preferably of at least 15.00 µmol per gram of fresh weight, especially preferably of at least 20.00 µmol per gram of fresh weight.

Preferably, plant cells according to the invention or plants according to the invention have a content of N-acetylated glucosamine derivatives of at most 250 µmol per gram of fresh weight, preferably of at most 200 µmol per gram of fresh weight, particularly preferably of at most 150 µmol per gram of fresh weight, very particularly preferably of at most 100 µmol per gram of fresh weight, especially preferably of at most 50 µmol per gram of fresh weight.

DETAILED DESCRIPTION OF THE INVENTION

Compared to the prior art, plant cells according to the invention or plants according to the invention offer the advantage that they contain higher amounts of N-acetylated glucosamine derivatives. Compared to the production of N-acetylated glucosamine derivatives by fermentation of microorganisms or the isolation of N-acetylated glucosamines from animal raw material sources or fungi, plant cells according to the invention or plants according to the invention of the present invention offer the advantage that plant cells according to the invention and plants according to the invention can be propagated infinitely in a vegetative or sexual manner, and that they continuously produce N-acetylated glucosamine derivatives. Furthermore, compared to known plants, plants according to the invention offer the advantage that they are better suitable for preparing glucosaminoglycans, such as, for example, chondroitin, hyaluronan, chitin, heparosan, since they contain a higher amount of substrates for the enzymes involved in the catalysis of the glucosaminoglycans mentioned (glucosaminoglycan synthases).

N-Acetylated glucosamine derivatives can be detected using methods known to the person skilled in the art (Morgan and Elson (1934, Biochem J. 28(3), 988-995). In the context of the present invention, for determining the content of N-acetylated glucosamine derivatives, use is preferably made of the method described under General Methods Item 4.

In the context of the present invention, the term "N-acetylated glucosamine derivatives" is to be understood as meaning all derivatives of glucosamine (2-amino-2-deoxyglucose), which also include epimers, such as, for example, galactosamine (2-amino-2-deoxygalactose) or mannosamine (2-amino-2-deoxymannose), which are measured using the method described under General Methods Item 4. The N-acetylated glucosamine derivatives are preferably N-acetylglucosamine phosphate (N-acetylglucosamine 1-phosphate and/or N-acetylglucosamine 6-phosphate), N-acetylglucosamine and/or UDP-N-acetylglucosamine.

Preferably plant cells according to the invention or plants according to the invention have an increased content of glucosamine phosphate (glucosamine 1-phosphate and/or glucosamine 6-phosphate) in addition to an increased content of N-acetylated glucosamine derivatives.

Plant cells according to the invention or plants according to the invention can be prepared, for example, by introducing foreign nucleic acid molecules coding for a protein having the activity of a glutamine:fructose 6-phosphate amidotransferase (GFAT) of isoform II (GFAT-2) or coding for a protein having the activity of a bacterial GFAT.

In a preferred embodiment of the present invention, the plant cells according to the invention or the plants according to the invention are thus genetically modified plant cells and genetically modified plants, respectively.

Surprisingly, it has been found that plant cells or plants containing a nucleic acid molecule coding for a protein having the activity of a GFAT-2 or a protein having the activity of a bacterial GFAT contain considerably more N-acetylated glucosamine derivatives than plant cells or plants containing a nucleic acid molecule coding for a protein having the activity of a glutamine:fructose 6-phosphate amidotransferase of isoform I (GFAT-1). As already mentioned, it was not possible to detect increased amounts of acetylated glucosamine derivatives in plants containing a nucleic acid molecule coding for a protein having the activity of a plant GFAT (WO 00 11192).

Accordingly, the present invention also provides genetically modified plant cells or genetically modified plants containing a foreign nucleic acid molecule coding for a protein having the activity of a glutamine:fructose 6-phosphate amidotransferase (GFAT), wherein the foreign nucleic acid molecule codes for a protein having the activity of a glutamine:fructose 6-phosphate amidotransferase of isoform II (GFAT-2) or a protein having the activity of a bacterial glutamine:fructose 6-phosphate amidotransferase (bacterial GFAT).

The genetic modification of a plant cell according to the invention or a plant according to the invention may be any genetic modification suitable for integrating a foreign nucleic acid molecule into a plant cell or plant.

Preferably, the foreign nucleic acid molecule is integrated into the genome; particularly preferably, the foreign nucleic acid molecule is stably integrated into the genome of plant cells according to the invention or plants according to the invention.

A large number of techniques for (stably) integrating nucleic acid molecules into a plant host cell for producing plant cells according to the invention or plants according to the invention is available. These techniques include the transformation of plant cells with T-DNA using *Agrobacterium tumefaciens* or *Agrobacterium rhizogenes* as means of transformation, protoplast fusion, injection, electroporation of DNA, introduction of DNA by the biolistic approach and also further options (review in "Transgenic Plants", Leandro ed., Humana Press 2004, ISBN 1-59259-827-7).

The use of *agrobacterium*-mediated transformation of plant cells has been subject to in-depth studies and has been described exhaustively in EP 120516 and Hoekema, IN: The Binary Plant Vector System Offsetdrukkerij Kanters B. V. Alblasserdam (1985), Chapter V; Fraley et al., Crit. Rev. Plant Sci. 4, 1-46 and in An et al. EMBO J. 4, (1985), 277-287. For the transformation of potatoes see, for example, Rocha-Sosa et al., EMBO J. 8, (1989), 29-33, for the transformation of tomato plants see, for example, U.S. Pat. No. 5,565,347.

The transformation of monocotyledonous plants using vectors based on *Agrobacterium* transformation has been described, too (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). Alternative systems for transforming monocotyledonous plants are the transformation using the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), the protoplast transformation, the electroporation of partially permeabilized cells or the introduction of DNA using glass fibers. In particular the transformation of corn has been described several times in the literature (cf., for example, WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The transformation of other grasses, such as, for example, switchgrass (*Panicum virgatum*) has also been described (Richards et al., 2001, Plant Cell Reporters 20, 48-54).

The successful transformation of other cereal species has likewise already been described, for example for barley (Wan and Lemaux, loc. cit.; Ritala et al., loc. cit.; Krens et al., Nature 296, (1982), 72-74) and for wheat (Nehra et al., Plant J. 5, (1994), 285-297; Becker et al., 1994, Plant Journal 5, 299-307). All of the above methods are suitable in the context of the present invention.

Genetically modified plant cells and genetically modified plants having a foreign nucleic acid molecule can be distinguished from wild-type plant cells and wild-type plants, respectively, not having said foreign nucleic acid molecule, inter alia by the fact that they contain a foreign nucleic acid molecule which does not naturally occur in wild-type plant cells and wild-type plants, respectively. Such an integration of a foreign nucleic acid molecule into a plant cell or plant can be detected using methods known to the person skilled in the art, such as, for example, Southern blot analysis or by PCR.

In the context of the present invention, the term "stably integrated nucleic acid molecule" is to be understood as meaning the integration of a nucleic acid molecule into the genome of the plant. A stably integrated nucleic acid molecule is characterized in that, during the replication of the corresponding integration site, it is multiplied together with the nucleic acid sequences of the host which border on the integration site, so that the integration site in the replicated daughter DNA strand is surrounded by the same nucleic acid sequences as on the read mother strand which serves as a matrix for the replication.

The integration of a nucleic acid molecule into the genome of a plant cell or a plant can be demonstrated by genetic methods and/or methods of molecular biology. A stable integration of a nucleic acid molecule into the genome of a plant cell or into the genome of a plant is characterized in that in the progeny which has inherited said nucleic acid molecule, the stably integrated nucleic acid molecule is present in the same genomic environment as in the parent generation. The presence of a stable integration of a nucleic acid sequence in the genome of a plant cell or in the genome of a plant can be demonstrated using methods known to the person skilled in the art, inter alia with the aid of Southern blot analysis or the RFLP analysis (Restriction Fragment Length Polymorphism) (Nam et al., 1989, The Plant Cell 1, 699-705; Leister and Dean, 1993, The Plant Journal 4 (4), 745-750), with methods based on PCR, such as, for example, the analysis of differences in length in the amplified fragment (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160) or using amplified fragments cleaved using restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

In the context of the present invention, the term "genome" is to be understood as meaning the entire genetic material present in a plant cell. It is known to the person skilled in the art that, in addition to the nucleus, other compartments (for example plastids, mitochondria) also contain genetic material.

A further preferred subject matter of the present invention relates to genetically modified plant cells according to the invention or genetically modified plants according to the invention expressing a foreign nucleic acid molecule coding for a protein having the activity of a glutamine:fructose 6-phosphate amidotransferase of isoform II (GFAT-2) or coding for a protein having the activity of a bacterial glutamine:fructose 6-phosphate amidotransferase (bacterial GFAT).

In the context of the present invention, the term "to express" or "expression" is to be understood as meaning the presence of transcripts (mRNA) coded for by a foreign nucleic acid molecule and/or the presence of proteins having the activity of a GFAT-2 or a bacterial GFAT.

An expression can be demonstrated, for example, by detection of specific transcripts (mRNA) of foreign nucleic acid molecules by Northern blot analysis or RT-PCR.

Whether plant cells or plants contain proteins having the activity of a GFAT-2 or proteins having the activity of a bacterial GFAT can be determined, for example, by immunological methods, such as Western blot analysis, ELISA (Enzyme Linked Immuno Sorbent Assay) or RIA (Radio Immune Assay). The person skilled in the art is familiar with methods for preparing antibodies which react specifically with a certain protein, i.e. which bind specifically to a certain protein (see, for example, Lottspeich and Zorbas (eds.), 1998, Bioanalytik, Spektrum akad, Verlag, Heidelberg, Berlin, ISBN 3-8274-0041-4). Some companies (for example Eurogentec, Belgium) offer the preparation of such antibodies as an order service.

In a further preferred embodiment of the present invention, plant cells according to the invention or plants according to the invention have an activity of a protein having the activity of a glutamine:fructose 6-phosphate amidotransferase of isoform II (GFAT-2) or of coding for a protein having the activity of a bacterial glutamine:fructose 6-phosphate amidotransferase (bacterial GFAT).

The activity of proteins having the activity of a GFAT-2 or proteins having the activity of a bacterial GFAT in extracts of plant cells according to the invention or plants according to the invention can be detected using methods known to the person skilled in the art, such as, for example, described in Samac et al. (2004, Applied Biochemistry and Biotechnology 113-116, Humana Press, Editor Ashok Mulehandani, 1167-1182, ISSN 0273-2289). A preferred method for determining the amount of activity of a protein having the activity of a GFAT is given in General Methods, Item 8.

In the context of the present invention, the term "glutamine:fructose 6-phosphate amidotransferase (GFAT)" (E.C. 2.6.1.16), in the expert literature also referred to as glucosamine synthase, is to be understood as meaning a protein which synthesizes, from the starting materials glutamine and fructose 6-phosphate (Fruc-6-P), glucosamine 6-phosphate (GlcN-6-P). This catalysis proceeds according to the following reaction scheme:

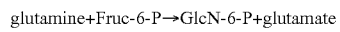
glutamine+Fruc-6-P→GlcN-6-P+glutamate

In the context of the present invention, the term "glutamine:fructose 6-phosphate amidotransferase (GFAT)" is used as a generic term which includes all known isoforms.

A review article by Milewski (2002, Biochimica et Biophysica Acta 1597, 173-193) describes structural features of proteins having the activity of a GFAT. The amino acid sequence of all known proteins having the activity of GFAT contains regions with conserved amino acid sequences. The amino acid sequence of proteins having the activity of a GFAT has an N-terminal glutamine binding domain and a C-terminal fructose 6-phosphate binding domain which are separated by a sequence of 40 to 90 non-conserved amino acids. Both domains are active even if they are present on separate amino acid molecules. Analyses of the crystal structure of a fragment comprising the N-terminal glutamine binding domain of the protein having the activity of a GFAT from *Escherichia coli* showed that the active center of this domain is located at the N-terminus and the amino acid Cys1 is involved in the hydrolysis of glutamine. The amino acids Arg73 and Asp123 interact with carboxyl and amino groups of the glutamine. This interaction is supported by the amino acids Thr76 and His77. The formation of hydrogen bonds with the amido group of the glutamine is attributed to the amino acids Gly99 and Trp74. The amino acids Asn98 and Gly99 stabilize the four-faced pocket of the active center. The amino acids 25 to 29 and 73-80 form flexible loops which, after binding of the substrate glutamine, contribute by a conformational change of the protein to the reaction catalyzed by a protein having the activity of a GFAT. Analysis of the crystal structure of the C-terminal fructose 6-phosphate binding domain of the protein having the activity of a GFAT from *Escherichia coli* showed that this domain is constructed of two topologically identical domains (amino acids 241 to 424 and 425 to 592) followed by a domain present at the C-terminal end as an irregular loop (amino acids 593 to 608), but which has only one active center. The amino acids Ser303, Ser347, Gln348, Ser349 and Thr352 are involved in substrate binding, whereas the amino acids Glu488, His504 and Lys603 are directly involved in the catalysis of the reaction of the protein having the activity of a GFAT.

In particular in animal organisms, it was possible to demonstrate two different isoforms of proteins having the activity of a GFAT (referred to in the literature as GFAT-1 and GFAT-2, respectively). Hu et al. (2004, J. Biol. Chem. 279(29), 29988-29993) describe differences of the respective isoforms of proteins having the activity of a GFAT. In addition to differences in the tissue-specific expression of the isoforms in question having the activity of a GFAT-1 and a GFAT-2, it was possible to show that both isoforms are regulated by phosphorylation by a cAMP-dependent protein kinase. The activity of a protein having the enzymatic activity of a GFAT-1 is inhibited by phosphorylation of a conserved serine residue (serine 205 in the GFAT-1 from the mouse, GenBank Acc No.: AF334736.1) of the amino acid sequence in question, whereas the activity of a protein having the activity of a GFAT-2 is increased by phosphorylation of a conserved serine residue (serine 202 in the GFAT-2 from the mouse, GenBank Acc No.: NM_013529) of the amino acid sequence in question. Both proteins having the activity of a GFAT-1 and proteins having the activity of a GFAT-2 are inhibited in a concentration-dependent manner by UDP-GlcNAc; however, for a protein having the activity of a GFAT-2, the inhibition by UDP-GlcNAc is lower (maximum reduction of activity by UDP-GlcNAc about 15%) compared to a protein having the activity of a GFAT-1 (maximum reduction of activity by UDP-GlcNAc by about 51% or 80%, respectively). There are indications that the inhibition of a protein having the activity of a GFAT-1 in animal organisms is based on the fact that at elevated UDP-GlcNAc concentrations there is an O-glucose-N-acetylglucosamine glycosylation of the proteins in question. Whether a regulation of the activity of proteins by O-glycosylation also takes part in plant cells is not yet fully understood (Huber and Hardin, 2004, Current Opinion in Plant Biotechnology 7, 318-322).

Proteins having the activity of a bacterial GFAT are distinguished by the fact that they are not inhibited by UDP-GlcNAc (Kornfeld, 1967, J. Biol. Chem. 242(13), 3135-3141). Proteins having the activity of a GFAT-1, proteins having the activity of a GFAT-2, and even proteins having the activity of a bacterial GFAT are inhibited by the product glucosamine 6-phosphate formed in their reaction (Broschat et al., 2002, J. Biol. Chem. 277(17), 14764-14770; Deng et al., 2005, Metabolic Engineering 7, 201-214).

In the context of the present invention, the term "protein having the activity of a glutamine:fructose 6-phosphate amidotransferase of isoform I (GFAT-1)" is to be understood as meaning a protein which has the activity of a GFAT and whose activity is inhibited by phosphorylation by a cAMP-dependent protein kinase.

In the context of the present invention, the term "protein having the activity of a glutamine:fructose 6-phosphate amidotransferase of isoform II (GFAT-2)" is to be understood as meaning a protein which has the activity of a GFAT and which is activated by phosphorylation by a cAMP-dependent protein kinase.

In the context of the present invention, the term "protein having the activity of a bacterial glutamine:fructose 6-phosphate amidotransferase (bacterial GFAT)" is to be understood as meaning a protein which has the activity of a GFAT and whose activity is not inhibited by UDP-GlcNAc. Alternatively, "proteins having the activity of a bacterial GFAT" may also be referred to as "proteins having the activity of a non-eukaryotic GFAT".

In the context of the present invention, the term "foreign nucleic acid molecule" is to be understood as meaning such a molecule which either does not naturally occur in corresponding wild-type plant cells or which does not naturally occur in the specific spatial arrangement in wild-type plant cells or which is localized at a site in the genome of the wild-type plant cell where it does not naturally occur.

Preferably, the foreign nucleic acid molecule is a recombinant molecule which consists of various elements (nucleic acid molecules) whose combination or specific spatial arrangement does not naturally occur in plant cells.

In the context of the present invention, the term "recombinant nucleic acid molecule" is to be understood as meaning a nucleic acid molecule which has various nucleic acid molecules which are not naturally present in a combination as present in a recombinant nucleic acid molecule. Thus, recombinant nucleic acid molecules may, in addition to foreign nucleic acid molecules coding for a protein, have, for example, additional nucleic acid sequences which are not naturally present in combination with said protein-encoding nucleic acid molecules. Here, the additional nucleic acid sequences mentioned, which are present in a recombinant nucleic acid molecule in combination with a protein-encoding nucleic acid molecule, may be any sequences. They may, for example, represent genomic and/or plant nucleic acid sequences.

The additional nucleic acid sequences mentioned are preferably regulatory sequences (promoters, termination signals, enhancer, introns), particularly preferably regulatory sequences active in plant tissue, very particularly preferably tissue-specific regulatory sequences active in plant tissue.

Methods for generating recombinant nucleic acid molecules are known to the person skilled in the art and include genetic engineering methods, such as, for example, linking of nucleic acid molecules by ligation, genetic recombination or the novel synthesis of nucleic acid molecules (see, for example, Sambrok et al., Molecular Cloning, A Laboratory Manual, 3rd edition (2001) Cold Spring Harbor Laboratory Press, Cold Spring Harbor, N.Y. ISBN: 0879695773; Ausubel et al., Short Protocols in Molecular Biology, John Wiley & Sons; 5th edition (2002), ISBN: 0471250929).

The present invention preferably provides genetically modified plant cells according to the invention or genetically modified plants according to the invention wherein the foreign nucleic acid molecules coding for a protein having the activity of a GFAT-2 or coding for a protein having the activity of a bacterial GFAT are linked to regulatory elements initiating the transcription in plant cells (promoters). These may be homologous or heterologous promoters. The promoters may be constitutive, tissue-specific or development-specific promoters or promoters regulated by external factors (for example after the application of chemical substances, by action of abiotic factors, such as heat and/or cold, dryness, disease, etc.).

In general, any promoters active in plant cells are suitable for expressing a foreign nucleic acid molecule. Suitable promoters are, for example, the promoter of 35S RNA of the cauliflower mosaic virus or the ubiquitin promoter from corn or the Cestrum YLCV Promoter (Yellow Leaf Curling Virus; WO 01 73087; Stavolone et al., 2003, Plant Mol. Biol. 53, 703-713) for a constitutive expression, the patatingen promoter B33 (Rocha-Sosa et al., EMBO J. 8 (1989), 23-29) for a tuber-specific expression in potatoes or a fruit-specific promoter for tomato, such as, for example, the polygalacturonase promoter from tomato (Montgomery et al., 1993, Plant Cell 5, 1049-1062) or the E8 promoter from tomato (Metha et al., 2002, Nature Biotechnol. 20(6), 613-618) or the ACC oxidase promoter from peach (Moon and Callahan, 2004, J. Experimental Botany 55 (402), 1519-1528) or a promoter which ensures expression only in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451) or for an endosperm-specific expression the HMWG promoter from wheat, the USP promoter, the phaseolin promoter, promoters of zein genes from corn (Pedersen et al., Cell 29 (1982), 1015-1026; Quatroccio et al., Plant Mol. Biol. 15 (1990), 81-93), a glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), a globulin promoter (Nakase et al., 1996, Gene 170(2), 223-226), a prolamin promoter (Qu and Takaiwa, 2004, Plant Biotechnology Journal 2(2), 113-125) or a shrunken-1 promoter (Werr et al., EMBO J. 4 (1985), 1373-1380). However, it is also possible to use promoters which are only active at a point in time determined by external factors (see, for example, WO 9307279). Of particular interest here may be promoters of heat-shock proteins which permit a simple induction. It is furthermore possible to use seed-specific promoters, such as, for example, the USP promoter from *Vicia faba* which ensures a seed-specific expression in *Vicia faba* and other plants (Fiedler et al., Plant Mol. Biol. 22 (1993), 669-679; Baumlein et al., Mol. Gen. Genet. 225 (1991), 459-467).

The use of promoters present in the genome of algae-infecting viruses is also suitable for expressing nucleic acid sequences in plants (Mitra et al., 1994, Biochem. Biophys Res Commun 204(1), 187-194; Mitra and Higgins, 1994, Plant Mol Biol 26(1), 85-93, Van Etten et al., 2002, Arch Virol 147, 1479-1516).

In the context of the present invention, the term "tissue specific" is to be understood as meaning the substantial limitation of a manifestation (for example initiation of transcription) to a certain tissue.

In the context of the present invention, the terms "tuber, fruit or endosperm cell" are to be understood as meaning all cells present in a tuber, a fruit and in an endosperm of a seed, respectively.

In the context of the present invention, the term "homologous promoter" is to be understood as meaning a promoter which is naturally present in plant cells or plants used for the preparation of genetically modified plant cells according to the invention and genetically modified plants according to the invention, respectively, (homologous with respect to the plant cell or the plant) or as meaning a promoter which regulates the regulation of the expression of a gene in the organism from which the respective foreign nucleic acid molecule coding for a protein was isolated (homologous with respect to the nucleic acid molecule to be expressed).

In the context of the present invention, the term "heterologous promoter" is to be understood as meaning a promoter which is not naturally present in plant cells or plants used for the preparation of genetically modified plant cells according to the invention and in genetically modified plants according to the invention, respectively, (heterologous with respect to the plant cell or plant) or as meaning a promoter which is, in the organism from which the respective foreign nucleic acid molecule coding for a protein was isolated, not naturally present for regulating the expression of said foreign nucleic acid molecule (heterologous with respect to the nucleic acid molecule to be expressed).

Also present may be a termination sequence (polyadenylation signal) which serves to add a poly-A tail to the transcript. The poly-A tail is thought to act in stabilizing the transcripts. Such elements are described in the literature (cf. Gielen et al., EMBO J. 8 (1989), 23-29) and can be exchanged as desired.

It is also possible for intron sequences to be present between the promoter and the coding region of the foreign nucleic acid molecule. Such intron sequences may lead to stability of expression and an increased expression in plants (Callis et al., 1987, Genes Devel. 1, 1183-1200; Luehrsen, and Walbot, 1991, Mol. Gen. Genet. 225, 81-93; Rethmeier et al., 1997; Plant Journal 12(4), 895-899; Rose and Beliakoff, 2000, Plant Physiol. 122 (2), 535-542; Vasil et al., 1989, Plant Physiol. 91, 1575-1579; X U et al., 2003, Science in China Series C Vol. 46 No. 6, 561-569). Suitable intron sequences are, for example, the first intron of the sh1 gene from corn, the first intron of the poly-ubiquitin gene 1 from corn, the first intron of the EPSPS gene from rice or one of the first two introns of the PAT1 gene from *Arabidopsis*.

According to the invention, the foreign nucleic acid molecule coding for a protein having the enzymatic activity of a GFAT-2 may originate from any eukaryotic organism; preferably, said nucleic acid molecule originates from animals, particularly preferably from mammals and very particularly preferably from the mouse.

According to the invention, the foreign nucleic acid molecule coding for a protein having the enzymatic activity of a bacterial GFAT may originate from any non-eukaryotic organism or from a virus genome; preferably, said nucleic acid molecule originates from bacteria or viruses; particularly preferably, said nucleic acid molecule originates from *Escherichia coli*. Since amino acid sequences coding for viral proteins having the activity of a GFAT have a considerably higher identity with amino acid sequences coding for proteins having the activity of a bacterial GFAT and a considerably lower identity with proteins having the activity of a GFAT-1 or a GFAT-2, viral proteins having the activity of a GFAT are classed with the bacterial proteins having the activity of a GFAT (Landstein et al., 1998, Virology 250, 388-396).

With regard to viruses, the foreign nucleic acid molecule coding for a protein having the enzymatic activity of a GFAT preferably originates from an algae-infecting virus, with preference a virus which infects algae of the genus *Chlorella*, particularly preferably from a *Paramecium bursaria Chlorella* virus and very particularly preferably from a *Paramecium bursaria Chlorella* virus of an H1 strain.

Instead of a naturally occurring nucleic acid molecule coding for a protein having the activity of a GFAT-2 or coding for a protein having the activity of a bacterial GFAT, a nucleic acid molecule introduced into genetically modified plant cells according to the invention or genetically modified plants according to the invention may also have been generated by mutagenesis, where said mutagenized foreign nucleic acid molecule is characterized in that it codes for a protein having the activity of a GFAT-2 or a protein having the activity of a bacterial GFAT which has reduced inhibition by metabolites (for example of the glucosamine metabolism). In an exemplary manner, the preparation of such mutagenized nucleic acid molecules is described in Deng et al. (2005, Metabolic Engineering 7, 201-214; WO 04 003175) for a protein having the activity of a bacterial GFAT from *Escherichia coli*. Mutants of a protein having the activity of a GFAT-2 from the mouse are described, for example, in Hu et al. (2004, J. Biol. Chem. 279 (29), 29988-29993).

Nucleic acid molecules coding for a protein having the activity of a GFAT are known to the person skilled in the art and described in the literature. Thus, nucleic acid molecules coding for a protein having the activity of a bacterial GFAT are described, for example, for *Escherichia coli* (Dutka-Malen, 1988, Biochemie 70 (2), 287-290; EMBL acc No: L10328.1), *Bacillus subtilis* (EMBL acc No U21932), *Haemophilus influenzae* (EMBL acc Nos AB006424.1, BAA33071). Nucleic acid molecules coding for a protein having the activity of a bacterial GFAT are also described for viruses, such as, for example, the *Chlorella* virus k2 (EMBL acc No AB107976.1).

Nucleic acid molecules coding for a protein having the activity of a GFAT-2 are described inter alia from insects, for example for *Drosophila melanogaster* (NCBI acc No NM_143360.2), from vertebrates, for example for *Homo sapiens* (NCBI acc No BC000012.2, Oki et al., 1999, Genomics 57 (2), 227-34) or *Mus musculus* (EMBL acc No AB016780.1).

In a preferred embodiment, the present invention relates to genetically modified plant cells according to the invention and genetically modified plants according to the invention where the foreign nucleic acid molecule coding for a protein having the activity of a GFAT-2 or coding for a protein having the activity of a bacterial GFAT is selected from the group consisting of a) nucleic acid molecules coding for a protein having the amino acid sequence given under SEQ ID NO 7 (GFAT-2) or a protein having the amino acid sequence given under SEQ ID NO 9 (bacterial GFAT);

b) nucleic acid molecules coding for a protein whose sequence is at least 60%, preferably at least 70%, more preferably at least 80%, particularly preferably at least 90%, very particularly preferably at least 95% and most preferably at least 98% identical to the amino acid sequence shown under SEQ ID NO 7 (GFAT-2) or under SEQ ID NO 9 (bacterial GFAT);

c) nucleic acid molecules comprising the nucleotide sequence shown under SEQ ID NO 6 (GFAT-2) or under SEQ ID NO 8 (bacterial GFAT) or under SEQ ID NO 10 (bacterial GFAT) or a sequence complementary thereto;

d) nucleic acid molecules which are at least 60%, preferably at least 70%, more preferably at least 80%, particularly preferably at least 90%, very particularly preferably at least 95% and most preferably at least 98% identical to the nucleic acid sequences shown under a) or c);

e) nucleic acid molecules which hybridize under stringent conditions with at least one strand of the nucleic acid sequences described under a) or c);

f) nucleic acid molecules whose nucleotide sequence differs from the sequence of the nucleic acid molecules mentioned under a) or c) owing to the degeneracy of the genetic code and g) nucleic acid molecules which are fragments, allelic variants and/or derivatives of the nucleic acid molecules mentioned under a), b), c), d), e) or f).

In the context of the present invention, the term "hybridization" means a hybridization under conventional hybridization conditions, preferably under stringent conditions, as described, for example, in Sambrook et al. (Molecular Cloning, A Laboratory Manual, 3rd edition (2001) Cold Spring Harbor Laboratory Press, Cold Spring Harbor, N.Y. ISBN: 0879695773) or Ausubel et al. (Short Protocols in Molecular Biology, John Wiley & Sons; 5th edition (2002), ISBN: 0471250929). With particular preference, "hybridization" means a hybridization under the following conditions:
hybridization buffer:
2×SSC; 10×Denhardt solution (Fikoll 400+PEG+BSA; ratio 1:1:1); 0.1% SDS; 5 mM EDTA; 50 mM $Na_2HPO_4$; 250 µg/ml of herring sperm DNA; 50 µg/ml of tRNA;
or
25 M sodium phosphate buffer pH 7.2; 1 mM EDTA; 7% SDS
hybridization temperature:
T=65 to 68° C.
wash buffer: 0.1×SSC; 0.1% SDS
wash temperature: T=65 to 68° C.

Nucleic acid molecules which hybridize with nucleic acid molecules coding for a protein having the activity of a GFAT-2 or coding for a protein having the activity of a bacterial GFAT may originate from any organism; accordingly, they may originate from bacteria, fungi, animals, plants or viruses.

Nucleic acid molecules which hybridize with nucleic acid molecules coding for a protein having the activity of a GFAT-2 preferably originate from animals, particularly preferably from mammals and very particularly preferably from the mouse.

Nucleic acid molecules which hybridize with nucleic acid molecules coding for a protein having the activity of a bacterial GFAT preferably originate from bacteria or viruses, particularly preferably from *Escherichia coli*.

Nucleic acid molecules which hybridize with the molecules mentioned may be isolated, for example, from genomic or from cDNA libraries. Such nucleic acid molecules can be identified and isolated using the nucleic acid molecules mentioned or parts of these molecules or the reverse complements of these molecules, for example by hybridization according to standard methods (see, for example, Sambrook et al., Molecular Cloning, A Laboratory Manual, 3rd edition (2001) Cold Spring Harbor Laboratory Press, Cold Spring Harbor, N.Y. ISBN: 0879695773; Ausubel et al., Short Protocols in Molecular Biology, John Wiley & Sons; 5th edition (2002), ISBN: 0471250929) or by amplification using PCR.

As hybridization sample for isolating a nucleic acid sequence coding for a protein having the activity of a GFAT-2, it is possible to use, for example, nucleic acid molecules having exactly or essentially the nucleic acid sequences described under SEQ ID NO 6 or fragments of these nucleic acid sequences. As hybridization sample for isolating a nucleic acid sequence coding for a protein having the activity of a bacterial GFAT, it is possible to use, for example, nucleic acid molecules having exactly or essentially the nucleic acid sequences described under SEQ ID NO 8 or fragments of these nucleic acid sequences.

The fragments used as hybridization samples may also be synthetic fragments or oligonucleotides prepared using the customary synthesis techniques, whose sequence is essentially identical to the nucleic acid molecule described in the context of the present invention. Once genes which hybridize with the nucleic acid sequences described in the context of the present invention are identified and isolated, the sequence should be determined and the properties of the proteins coded for by this sequence should be analyzed to determine whether they are proteins having the activity of a GFAT-2 or the activity of a bacterial GFAT. Methods of how to determine whether a protein has the activity of a protein having the activity of a GFAT-2 or having the activity of a bacterial GFAT are known to the person skilled in the art and described, inter alia, in the literature (bacterial GFAT: for example Deng et al., 2005, Metabolic Engineering 7, 201-214; Kornfeld, 1967, J. Biol. Chem. 242(13), 3135-3141; GFAT-2: for example Hu et al., 2004, J. Biol. Chem. 279 (29), 29988-29993). The molecules hybridizing with the nucleic acid molecules described in the context of the present invention comprise in particular fragments, derivatives and allelic variants of the nucleic acid molecules mentioned. In the context of the present invention, the term "derivative" means that the sequences of these molecules differ in one or more positions from the sequences of the nucleic acid molecules described above and are highly identical to these sequences. The differences to the nucleic acid molecules described above may, for example, be due to deletion (in particular deletion of N- and/or C-terminal regions), addition, substitution, insertion or recombination.

In the context of the present invention, the term "identity" means a sequence identity over the entire length of the coding region of a nucleic acid molecule or the entire length of an amino acid sequence coding for a protein of at least 60%, in particular an identity of at least 70%, preferably of at least 80%, particularly preferably of at least 90%, very particularly preferably of at least 95% and most preferably at least 98%. In the context of the present invention, the term "identity" is to be understood as meaning the number of identical amino acids/nucleotides (identity) with other proteins/nucleic acids, expressed in percent.

Preferably, the identity with respect to a protein having the activity of a GFAT-2 is determined by comparisons with the amino acid sequence given under SEQ ID NO 7 and the identity with respect to a nucleic acid molecule coding for a protein having the activity of a GFAT-2 as determined by comparisons of the nucleic acid sequence given under SEQ ID NO 6 with other proteins/nucleic acids with the aid of computer programs. Preferably, the identity with respect to a protein having the activity of a bacterial GFAT is determined by comparisons of the amino acid sequence given under SEQ ID NO 9 and the identity with respect to a nucleic acid molecule coding for a protein having the activity of a bacterial GFAT is determined by comparisons of the nucleic acid sequence given under SEQ ID NO 8 or SEQ ID NO 10 with other proteins/nucleic acids with the aid of computer programs. If sequences to be compared with one another are of different length, the identity is to be determined by determining the identity in percent of the number of amino acids/nucleotides which the shorter sequence shares with the longer sequence. Preferably, the identity is determined using the known and publicly available computer program ClustalW (Thompson et al., Nucleic Acids Research 22 (1994), 4673-4680). ClustalW is made publicly available by Julie Thompson and Toby Gibson, European Molecular Biology Laboratory, Meyerhofstrasse 1, D 69117 Heidelberg, Germany. ClustalW can also be downloaded from various Internet pages, inter alia from IGBMC (Institut de Genetique et de Biologie Moleculaire et Cellulaire, B.P. 163, 67404 Illkirch Cedex, France) and from EBI and all mirrored Internet pages of the EBI (European Bioinformatics Institute, Wellcome Trust Genome Campus, Hinxton, Cambridge CB10 ISD, UK).

Preferably, use is made of the ClustalW computer program of version 1.8 to determine the identity between proteins described in the context of the present invention and other proteins. Here, the parameters have to be set as follows: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, use is made of the ClustalW computer program of version 1.8 to determine the identity for example between the nucleotide sequence of the nucleic acid molecules described in the context of the present invention and the nucleotide sequence of other nucleic acid molecules. Here, the parameters have to be set as follows: KTUPLE=2, TOPDIAGS=4, PAIRGAP=5, DNAMATRIX:IUB, GAPOPEN=10, GAPEXT=5, MAXDIV=40, TRANSITIONS:unweighted.

Identity furthermore means that there is a functional and/or structural equivalence between the nucleic acid molecules in question or the proteins encoded by them. The nucleic acid molecules which are homologous to the molecules described above and represent derivatives of these molecules are generally variations of these molecules which represent modifications having the same biological function, i.e. coding for a protein having the activity of a GFAT-2 or the activity of a bacterial GFAT. They may be either naturally occurring variations, for example sequences from other species, or mutations, where these mutations may have occurred in a natural manner or were introduced by systematic mutagenesis. Furthermore, the variations may be synthetically produced sequences. The allelic variants may be either naturally occurring variants or synthetically produced variants or variants generated by recombinant DNA techniques. A special form of derivatives are, for example, nucleic acid molecules which differ from the nucleic acid molecules described in the context of the present invention as a result of the degeneracy of the genetic code.

In a further preferred embodiment, the present invention relates to genetically modified plant cells according to the invention or genetically modified plants according to the invention where nucleic acid molecules coding for a protein having the activity of a GFAT-2 or coding for a protein having the activity of a bacterial GFAT are characterized in that the codons of said nucleic acid molecules are different from the codons of the nucleic acid molecules which code for said protein having the activity of a GFAT-2 or said protein having the activity of a bacterial GFAT of the parent organism. Particularly preferably, the codons of the nucleic acid molecules coding for a protein having the activity of a GFAT-2 or coding for a protein having the activity of a bacterial GFAT are changed such that they are adapted to the frequency of use of the codons of the plant cell or the plant into whose genome they are integrated or to be integrated.

As a result of the degeneracy of the genetic code, amino acids can be encoded by one or more codons. In different organisms, the codons coding for an amino acid are used at different frequencies. Adapting the codons of a coding nucleic acid sequence to the frequency of their use in the plant cell or in the plant into whose genome the sequence to be expressed is to be integrated may contribute to an increased amount of translated protein and/or to the stability of the mRNA in question in the particular plant cells or plants. The frequency of use of codons in the plant cells or plants in question can be determined by the person skilled in the art by examining as many coding nucleic acid sequences of the organism in question as possible for the frequency with which certain codons are used for coding a certain amino acid. The frequency of the use of codons of certain organisms is known to the person skilled in the art and can be determined in a simple and rapid manner using computer programs. Such computer programs are publicly accessible and provided for free inter alia on the Internet (for example Graphic Codon Usage Analyser; Codon Usage Database; and Computational Molecular Biology and Evolutionary Bioinformatics websites). Adapting the codons of a coding nucleic acid sequence to the frequency of their use in the plant cell or in the plant into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany). Adapting the codons of a coding nucleic acid sequence to the frequency of their use in the plant cell or in the plant into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany).

All of the nucleic acid molecules mentioned are suitable for producing plant cells according to the invention or plants according to the invention.

The genetically modified plant cells according to the invention or the genetically modified plants according to the invention may, in principle, be plant cells and plants, respectively, of any plant species, i.e. both monocotyledonous and dicotyledonous plants. They are preferably crop plants, i.e. plants cultivated by man for the purpose of feeding man and animal or for producing biomass and/or for preparing substances for technical, industrial purposes. The genetically modified plant cells according to the invention or the genetically modified plants according to the invention are particularly preferably corn, rice, wheat, rye, oats, barley, manioc, potato, tomato, switchgrass (*Panicum virgatum*), sago, mung beans, peas, sorghum, carrots, eggplant, radish, oilseed rape, alfalfa, soybean, peanuts, cucumbers, pumpkins, melons, leek, garlic, cabbage, spinach, sweet potato, asparagus, zucchini, lettuce, artichokes, sweetcorn, parsnip, salsify, Jerusalem artichoke, banana, sugar beet, sugar cane, beetroot, broccoli, cabbage, onion, beet, dandelion, strawberry, apple, apricot, plum, peach, grapevines, cauliflower, celery, bell peppers, swede, rhubarb. They are preferably corn, rice, wheat, rye, oat or barley plants, very particularly preferably rice, tomato or potato plants.

In the context of the present invention, the term "potato plant" or "potato" is to be understood as meaning plant species of the genus *Solanum*, particularly tuber-producing species of the genus *Solanum* and in particular *Solanum tuberosum*.

In the context of the present invention, the term "tomato plant" or "tomato" is to be understood as meaning plant species of the genus *Lycopersicon*, in particular *Lycopersicon esculentum*.

In the context of the present invention, the term "rice plant" is to be understood as meaning plant species of the genus *Oryza*, in particular plant species of the genus *Oryza* agriculturally cultivated for commercial purposes, particularly preferably *Oryza saliva*.

As already discussed, plant cells according to the invention or plants according to the invention are suitable for producing glucosaminoglycans, such as, for example, chondroitin, hyaluronan, chitin, heparin (heparosan), since they contain a higher amount of substrates for the enzymes involved in the catalysis of the glucosaminoglycans mentioned.

Accordingly, the present invention furthermore relates to plant cells or plants synthesizing glucosaminoglycan, preferably at least 500 µg of glucosaminoglycan per gram of fresh weight, more preferably at least 1500 µg of glucosaminoglycan per gram of fresh weight, particularly preferably at least 3500 µg of glucosaminoglycan per gram of fresh weight, very particularly preferably at least 4000 µg of glucosaminoglycan per gram of fresh weight and especially preferably at least 5500 µg of glucosaminoglycan per gram of fresh weight. In this context, the glucosaminoglycan is preferably chondroitin, hyaluronan, chitin or heparin (heparosan), particularly preferably hyaluronan.

Plant cells according to the invention or plants according to the invention preferably have a glucosaminoglycan content of at most 25 000 µmol per gram of fresh weight, preferably at most 20 000 µmol per gram of fresh weight, particularly preferably at most 15 000 µmol per gram of fresh weight, very particularly preferably at most 10 000 µmol per gram of fresh weight, especially preferably at most 6500 µmol per gram of fresh weight.

Plant cells according to the invention or plants according to the invention which synthesize glucosaminoglycan can be produced, for example, by introducing foreign nucleic acid molecules coding for a protein having the activity of a GFAT and coding for a protein having the activity of a glucosaminoglycan synthase into a plant cell.

Accordingly, the present invention also relates to genetically modified plant cells or genetically modified plants containing a first foreign nucleic acid molecule coding for a protein having the activity of a GFAT-2 or a bacterial GFAT and a second foreign nucleic acid molecule coding for a protein having the activity of a glucosaminoglycan synthase.

In the context of the present invention, the term "protein having the activity of a glucosaminoglycan synthase" is to be understood as meaning a protein which uses UDP-GlcNAc or UDP-N-acetylgalactosamine, an epimer of UDP-GlcNAc, as substrate for synthesizing a glucosaminoglycan. The protein having the activity of a glucosaminoglycan synthase is preferably a hyaluronan synthase, chondroitin synthase, heparosan/heparin synthase, keratan synthase or chitin synthase.

Nucleic acid molecules and corresponding protein sequences coding for glucosaminoglycan synthases are known to the person skilled in the art and described as hyaluronan synthase for example from viruses (for example *Paramecium bursaria Chlorella* Virus 1, EMBL U42580.3, PB42580, US 20030235893), as chondroitin synthase for example from mammals (for example *Homo sapiens*, WO 03 012099, US 2005048604, US 2006052335), bacteria (for example *Escherichia coli*, US2003109693, EP 1283259, *Pasteurella multicoda* US 2003104601), as chitin synthase for example from bacteria (for example *Azorhizobium caulinodans* EMBLCDS:AAB51164), from fungi (for example *Chaetomium globosum* EMBLCDS:EAQ92361, *Aspergillus nidulans* EMBL AB00125, *Arthroderma benhamiae* EMBLCDS:BAB32692 *Neurospora crassa* EMBL M73437.4), from insects (for example *Aedes aegypti* EMBLCDS:EAT46081, *Tribolium castaneum* EMBLCDS: AAQ55061), nematodes (for example *Dirofilaria immitis* EMBL AF288618, *Caenorhabditis elegans* EMBL AY874871), from viruses (for example *Chlorella* virus EMBLCDS: BAB83509, *Paramecium bursaria Chlorella* virus CVK2 EMBLCDS: BAE48153), as heparin/heparosan synthase for example from bacteria (for example *Pasteurella multocida* EMBL AF425591, AF439804, US 20030099967, *Escherichia coli* X77617.1).

The second foreign nucleic acid molecule coding for a protein having the activity of a glucosaminoglycan synthase is preferably a recombinant nucleic acid molecule. Preferred embodiments of recombinant nucleic acid molecules have already been described and are to be used here in a corresponding manner.

In a further preferred embodiment, the second foreign nucleic acid molecule coding for a protein having the activity of a glucosaminoglycan synthase is characterized in that the codons are modified compared to the codons of the nucleic acid molecule coding for said protein having the activity of a glucosaminoglycan synthase of the parent organism. Particularly preferably, the codons of the nucleic acid molecules coding for a protein having the activity of a glucosaminoglycan synthase are modified such that they are adapted to the frequency of use of the codons of the plant cell or the plant into whose genome they are integrated or to be integrated.

What was stated above for nucleic acid molecules coding for a protein having the activity of a GFAT-2 or a bacterial GFAT with respect to the modification of the codons of a nucleic acid molecule is to be applied here in a corresponding manner.

The present invention furthermore relates to plants containing plant cells according to the invention. Such plants may be generated by regeneration from plant cells according to the invention.

The present invention also relates to parts of plants according to the invention containing plant cells according to the invention.

In the context of the present invention, the term "plant parts" or "parts of plants" is to be understood as meaning, for example, processible plant parts used in the production of foodstuff or feedstuff, used as raw material source for industrial processes (for example for the isolation of glucosamine derivatives or glucosaminoglycans), as raw material source for the preparation of pharmaceuticals or as raw material source for the preparation of cosmetic products.

In the context of the present invention, the term "plant parts" or "parts of plants" is furthermore to be understood as meaning, for example, consumable plant parts which serve as food for man or which are used as animal feed.

Preferred "plant parts" or "parts of plants" are fruits, storage and other roots, flowers, buds, shoots, leaves or stalks, preferably seeds, fruits, grains or tubers.

The present invention also relates to propagation material of plants according to the invention. Preferably, propagation material according to the invention contains plant cells according to the invention, particularly preferably genetically modified plant cells according to the invention.

Here, the term "propagation material" comprises those components of the plant which are suitable for generating progeny via the vegetative or generative route. Suitable for vegetative propagation are, for example, cuttings, callus cultures, rhizomes or tubers. Other propagation material includes, for example, fruits, seeds, grains, seedlings, cell cultures, etc. The propagation material preferably takes the form of tubers, fruits, grains or seeds.

A further advantage of the present invention is the fact that parts of plants according to the invention have a higher content of N-acetylated glucosamine derivatives than known plants. Accordingly, plants according to the invention are particularly suitable for direct use as foodstuff/feedstuff or for preparing foodstuff/feedstuff having a prophylactic or therapeutic effect (for example for osteoarthritis prophylaxis). Since plants according to the invention have a higher content of N-acetylated glucosamine derivatives compared to known plants, the amounts of harvestable parts, propagation material, processible parts or consumable parts of plants according to the invention used for preparing foodstuff/feedstuff having an increased content of N-acetylated glucosamine derivatives can be reduced. If consumable parts of genetically modified plants according to the invention are consumed, for example, directly as so-called nutraceutical, a positive effect may be achieved even by the consumption of small amounts of substance. This may be of particular importance inter alia in the production of animal feed since animal feed with too high a content of plant components is unsuitable as feedstuff for various animal species. Furthermore, plant cells according to the invention or plants according to the invention have the advantage that they can also be used by vegans or for preparing kosher food. It is thus possible to administer food having an elevated content of N-acetylated glucosamines even to people following the ways of life mentioned.

It is known that N-acetylglucosamine has a stimulating effect on the growth of bifido bacteria (Liepke et al., 2002, Eur. J. Biochem. 269, 712-718). Furthermore, it has been shown that N-acetylglucosamine serves as a substrate for lactobacilli (for example *Lactobacillus casei* subspecies *paracasei*) from fish gut (Adolfo Bucio Galindo, 2004, Proefschrift, Wageningen Universiteit, ISBN 90-5808-943-6). Accordingly, N-acetylglucosamine has a positive effect on probiotic bacteria. Since plant cells according to the invention, plants according to the invention or parts of plants according to the invention have an elevated content of N-acetylglucosamine, they should consequently have a positive effect on the growth of probiotic bacteria and thus be suitable for use as a prebiotic foodstuff/feedstuff for man and animal.

The present invention furthermore relates to a process for producing a genetically modified plant which comprises the following steps:
a) introduction of a foreign nucleic acid molecule coding for a protein having the activity of a glutamine:fructose 6-phosphate amidotransferase of isoform II (GFAT-2) or coding for a protein having the activity of a bacterial glutamine:fructose 6-phosphate amidotransferase (bacterial GFAT) into a plant cell
b) regeneration of a plant from plant cells obtained according to step a)
c) if appropriate, generation of further plants with the aid of the plants according to step b).

The present invention furthermore relates to processes for producing a plant which synthesizes glucosaminoglycan, wherein
a) a plant cell is genetically modified, where the genetic modification comprises the following steps i to ii in any order or carrying out any combinations of the following steps i to ii individually or simultaneously
  i) introducing a foreign nucleic acid molecule coding for a protein having the activity of a glutamine:fructose 6-phosphate amidotransferase of isoform II (GFAT-2) or coding for a protein having the activity of a bacterial glutamine:fructose 6-phosphate amidotransferase (bacterial GFAT) into a plant cell
  ii) introducing a foreign nucleic acid molecule coding for a glucosaminoglycan synthase into a plant cell
b) a plant is regenerated from plant cells comprising the genetic modification according to steps
  i) a) i
  ii) a) ii
  iii) a) i and a) ii,
c) introducing into plant cells of plants according to step
  i) b) i a genetic modification according to step a) ii,
  ii) b) ii a genetic modification according to step a) i, and regenerating a plant
d) if appropriate, generating further plants with the aid of the plants obtained according to any of steps b) iii or c) i or c) ii.

With regard to the introduction of foreign nucleic acid molecules according to step a) of the process for producing a genetically modified plant or according to steps a) or c) of the process for producing a plant which synthesizes glucosaminoglycan into a plant cell, this introduction may, in principle, be any type of introduction of nucleic acid molecules suitable for integrating a foreign nucleic acid molecule into a plant cell or plant. Such methods have already been described above and can be applied here in a corresponding manner.

With respect to the foreign nucleic acid molecule coding for a protein having the activity of a GFAT-2 or coding for a protein having the activity of a bacterial GFAT according to step a) of the process for producing a genetically modified plant or with respect to the foreign nucleic acid molecule coding for a protein having the activity of a glucosaminoglycan synthase according to step a) ii) of the process for producing a plant which synthesizes glucosaminoglycan, various possible embodiments of the respective nucleic acid molecules have already been described in the context with plant cells according to the invention and plants according to the invention. All these preferred embodiments which have already been described can also be used for carrying out the processes according to the invention mentioned.

The regeneration of the plants depending on the process according to step b) and/or c) of the processes according to the invention can be carried out using methods known to the person skilled in the art (described, for example, in "Plant Cell Culture Protocols", 1999, edt. by R. D. Hall, Humana Press, ISBN 0-89603-549-2).

The generation of further plants depending on the process according to the step c) or d) of the processes according to the invention can be carried out, for example, by vegetative propagation (for example via cuttings, tubers or via callus culture and regeneration of intact plants) or via generative propagation. In this context, generative propagation preferably takes place under controlled conditions, i.e. selected plants with specific characteristics are hybridized with one another and multiplied. The selection preferably takes place in such a manner that the plants, depending on the process according to step b) or d), have the modifications introduced in step a).

In a further preferred embodiment, processes according to the invention for producing a genetically modified plant are used for producing plants according to the invention.

The present invention also provides plants obtainable by processes according to the invention for preparing a genetically modified plant.

The present invention furthermore relates to a process for producing glucosaminoglycans which comprises the step of the extraction of glucosaminoglycans from genetically modified plant cells according to the invention, from genetically modified plants according to the invention, propagation material according to the invention, parts of plants according to the invention or plants obtainable by a process according to the invention for preparing a genetically modified plant which synthesizes glucosaminoglycan. The process according to the invention is preferably used for producing chondroitin, hyaluronan, chitin or heparin (heparosan), particularly preferably for producing hyaluronan.

Preferably, such a process also comprises the step of harvesting the cultivated genetically modified plant cells according to the invention, the genetically modified plants according to the invention, the propagation material according to the invention, the parts of plants according to the invention prior to the extraction of the glucosaminoglycan and particularly preferably furthermore the step of the cultivation of genetically modified plant cells according to the invention or genetically modified plants according to the invention prior to harvesting.

In contrast to bacterial or animal tissues, plant tissues do not contain any glucosaminoglycan-degrading enzymes. Accordingly, extraction of glucosaminoglycans from plant tissue is possible using relatively simple methods. If required, aqueous extracts of plant cells or tissues containing glucosaminoglycan can be purified further using methods known to the person skilled in the art, such as, for example, repeated precipitation with ethanol. A preferred method for purifying, for example, hyaluronan is described under General Methods Item 5.

The present invention also provides the use of genetically modified plant cells according to the invention, genetically modified plants according to the invention, propagation material according to the invention, parts of plants according to the invention or plants obtainable by a process according to the invention for producing a genetically modified plant which synthesizes glucosaminoglycan for producing glucosaminoglycans.

The present invention also provides the use of nucleic acid molecules coding for a protein having the activity of a GFAT-2 or coding for a protein having the activity of a bacterial GFAT for preparing a genetically modified plant.

The present invention furthermore relates to a composition comprising genetically modified plant cells according to the invention.

Here, it is immaterial whether the plant cells are intact or no longer intact because they have been destroyed, for example, by processing. The compositions are preferably foodstuff, food supplements or feedstuff, pharmaceutical or cosmetic products.

The present invention preferably provides compositions according to the invention comprising recombinant nucleic acid molecules, the recombinant nucleic acid molecules being characterized in that they comprise nucleic acid molecules coding for a protein having the enzymatic activity of a GFAT-2 or a protein having the activity of a bacterial GFAT.

A stable integration of foreign nucleic acid molecules into the genome of a plant cell or plant results in the foreign nucleic acid molecules being flanked after integration into the genome of the plant cell or plant by genomic plant nucleic acid sequences. Accordingly, in a preferred embodiment, compositions according to the invention are characterized in that the recombinant nucleic acid molecules present in the composition according to the invention are flanked by genomic plant nucleic acid sequences.

Here, the genomic plant nucleic acid sequences may be any sequences naturally present in the genome of the plant cell or plant used for preparing the composition. That recombinant nucleic acid molecules which are present in the compositions according to the invention can be demonstrated using methods known to the person skilled in the art, such as, for example, methods based on hybridization or, preferably, methods based on PCR (Polymerase Chain Reaction).

Preferably, the compositions according to the invention comprise at least 0.05%, preferably at least 0.1%, particularly preferably at least 0.5%, very particularly preferably at least 1.0%, of N-acetylated glucosamine derivatives.

Preferably, the compositions according to the invention comprise at most 10%, preferably at most 5%, particularly preferably at most 3%, very particularly preferably at most 2%, of N-acetylated glucosamine derivatives.

Compositions according to the invention offer the advantage that they have an increased content of N-acetylated glucosamine derivatives or an increased content of glucosaminoglycans compared to compositions comprising not genetically modified plant cells. N-Acetylglucosamine has a stimulating effect on the growth of bifido bacteria (Liepke et al., 2002, Eur. J. Biochem. 269, 712-718). Furthermore, it has been shown that N-acetylglucosamine serves as substrate for lactobacilli (for example *Lactobacillus casei* subspecies *paracasei*) from fish gut (Adolfo Bucio Galindo, 2004, Proefschrift, Wageningen Universiteit, ISBN 90-5808-943-6). Accordingly, N-acetylglucosamine has a positive effect on probiotic bacteria. Since compositions according to the invention have increased N-acetylglucosamine contents, they should have a positive effect on the growth of probiotic bacteria.

The invention furthermore provides processes for preparing a composition according to the invention using plant cells according to the invention, plants according to the invention, propagation material according to the invention, parts of plants according to the invention or plants obtainable by a process according to the invention for producing a genetically modified plant. The processes for preparing a composition according to the invention are preferably processes for producing foodstuff, feedstuff or food supplements.

Processes for producing foodstuff, feedstuff, food supplements, pharmaceutical products or cosmetic products are known to the person skilled in the art and comprise inter alia, but are not exclusively limited to, the comminuting or the grinding of plants according to the invention or plant parts according to the invention.

The present invention also provides compositions obtainable by a process for preparing a composition according to the invention.

The present invention also relates to the use of genetically modified plant cells according to the invention or genetically modified plants according to the invention for preparing a composition according to the invention.

A preferred embodiment of compositions according to the invention are flours.

Parts of plants are frequently processed to flours. Examples of parts of plants which are used to prepare flours are, for example, tubers of potato plants and grains of cereal plants. To produce flours from cereal plants, the endosperm-containing grains of these plants are ground and sieved. In the case of other plants which do not contain any endosperm but, for example, tubers or storage roots, flour is often produced by comminuting, drying and subsequent grinding of the relevant parts of the plants. Plant cells according to the invention and plants according to the invention have an increased content of N-acetylated glucosamine derivatives or glucosaminoglycans compared to known plant cells or plants. Flours prepared from plant cells according to the invention, plants according to the invention, propagation material according to the invention or parts of plants according to the invention accordingly likewise contain an increased proportion of N-acetylated glucosamine derivatives or glucosaminoglycans.

Accordingly, the present invention furthermore relates to flours which obtainable from plant cells according to the invention, plants according to the invention or from parts of plants according to the invention. Preferred parts of plants according to the invention for producing flours are tubers and endosperm-containing grains. In the context of the present invention, particular preference is given to grains of plants of the (systematic) family Poaceae, especially preferably, the grains originate from corn, rice or wheat plants.

The present invention furthermore relates to flours according to the invention having a content of N-acetylated glucosamine derivatives of at least 10 µmol per gram, preferably at least 20 µmol per gram, more preferably at least 25 µmol per gram, particularly preferably at least 30 µmol per gram, very particularly preferably at least 35 µmol per gram and especially preferably at least 40 µmol per gram.

Flours according to the invention preferably have a content of N-acetylated glucosamine derivatives of at most 250 µmol per gram of fresh weight, preferably at most 200 µmol per gram of fresh weight, particularly preferably at most 150 µmol per gram of fresh weight, very particularly preferably at most 100 µmol per gram of fresh weight and especially preferably at most 50 µmol per gram of fresh weight.

In the context of the present invention, the term "flour" is to be understood as meaning a powder obtained by grinding plants or plant parts. If appropriate, the plants or plant parts are dried prior to grinding and, after grinding, further comminuted and/or sieved.

Compared to conventional flours, flours according to the invention have the advantage that they can be used for producing foodstuff, such as, for example, baked goods, having an increased content of N-acetylated glucosamine derivatives or glucosaminoglycans without it being necessary to add N-acetylated glucosamine derivatives or glucosaminoglycans obtained from animal or fungal raw material sources to the flour. The disadvantages of the use of N-acetylated glucosamine derivatives or glucosaminoglycans isolated from the raw material sources mentioned, such as, for example, the risk that they may contain pathogens or allergenic substances, have already been mentioned further above.

The present invention furthermore provides a process for producing flours which comprises the step of grinding plant cells according to the invention, plants according to the invention or parts of plants according to the invention.

Flours can be produced by grinding parts of plants. It is known to the person skilled in the art how to produce flours. A process for producing flours preferably also comprises the step of harvesting the cultivated plants according to the invention or parts of plants according to the invention and/or the propagation material according to the invention and particularly preferably furthermore the step of the cultivation of plants according to the invention prior to harvesting.

In a further embodiment of the present invention, the process for producing flours comprises processing of plants according to the invention, of parts of plants according to the invention or of propagation material according to the invention.

Here, processing may, for example, be heat treatment and/or drying. Heat treatment followed by drying of the heat-treated material is used, for example, when producing flours from storage roots, tubers such as, for example, from potato tubers, prior to grinding. Comminuting of plants according to the invention, of parts of plants according to the invention or of propagation material according to the invention may also constitute processing in the sense of the present invention. Removal of plant tissue, such as, for example, removal of the husk from the grains, prior to grinding also constitutes processing prior to grinding in the sense of the present invention.

In a further embodiment of the present invention, the process for producing flours comprises processing of the ground material after grinding.

Here, the ground material may, for example, be sieved after grinding, for example to produce different types of flour.

The present invention furthermore provides the use of plant cells according to the invention, plants according to the invention, of parts of plants according to the invention or of propagation material according to the invention for producing flours.

Description of the Sequences

SEQ ID NO 1: Nucleic acid sequence coding for a hyaluronan synthase of *Paramecium bursaria Chlorella* Virus 1.

SEQ ID NO 2: Amino acid sequence of a hyaluronan synthase of *Paramecium bursaria Chlorella* Virus 1. The amino acid sequence shown can be derived from SEQ ID NO 1.

SEQ ID NO 3: Synthetic nucleic acid sequence coding for a hyaluronan synthase of *Paramecium bursaria Chlorella* Virus 1. The codons of the sequence shown were synthesized in a manner such that they are adapted to the use of codons in plant cells. The nucleic acid sequence shown codes for a protein having the amino acid sequence shown under SEQ ID NO 2.

SEQ ID NO 4: Nucleic acid sequence coding for a protein having the activity of a GFAT-1 from the mouse.

SEQ ID NO 5: Amino acid sequence of a protein having the activity of a GFAT-1 from the mouse. The amino acid sequence shown can be derived from SEQ ID NO 4.

SEQ ID NO 6: Nucleic acid sequence coding for a protein having the activity of a GFAT-2 from the mouse.

SEQ ID NO 7: Amino acid sequence of a protein having the activity of a GFAT-2 from the mouse. The amino acid sequence shown can be derived from SEQ ID NO 6.

SEQ ID NO 8: Nucleic acid sequence coding for a protein having the activity of a bacterial GFAT from *Escherichia coli*.

SEQ ID NO 9: Amino acid sequence of a protein having the activity of a GFAT from *Escherichia coli*. The amino acid sequence shown can be derived from SEQ ID NO 8.

SEQ ID NO 10: Synthetic nucleic acid sequence coding for a protein having the activity of a GFAT from *Escherichia coli*. The codons of the sequence shown were synthesized in a manner such that they are adapted to the use of codons in plant cells. The nucleic acid sequence shown codes for a protein having the amino acid sequence shown under SEQ ID NO 9.

SEQ ID NO 11: Nucleic acid sequence coding for a protein having the activity of a UDP-glucose dehydrogenase of *Paramecium bursaria Chlorella* Virus 1.

SEQ ID NO 12: Amino acid sequence of a protein having the activity of a UDP-glucose dehydrogenase of *Paramecium bursaria Chlorella* Virus 1. The amino acid sequence shown can be derived from SEQ ID NO 11.

SEQ ID NO 13: Synthetic nucleic acid sequence coding for a protein having the activity of a UDP-glucose dehydrogenase of *Paramecium bursaria Chlorella* Virus 1. The codons of the sequence shown were synthesized in a manner such that they are adapted to the use of codons in plant cells. The nucleic acid sequence shown codes for a protein having the amino acid sequence shown under SEQ ID NO 12.

SEQ ID NO 14: Synthetic oligonucleotide which was used in example 6.

SEQ ID NO 15: Synthetic oligonucleotide which was used in example 6.

SEQ ID NO 16: Synthetic oligonucleotide which was used in example 15.

SEQ ID NO 17: Synthetic oligonucleotide which was used in example 15.

The content of all cited publications including the accession numbers of nucleic acid molecules and amino acid sequences mentioned for sequence databases is incorporated by reference into the description of the application.

Methods which can be used in connection with the present invention are described below. These methods are specific embodiments; however, the present invention is not limited to these methods. It is known to the person skilled in the art that the invention can be carried out in the same manner by modifying the methods described and/or by replacing individual methods or parts of methods by alternative methods or alternative parts of methods.

General Methods

1. Transformation of Potato Plants

Potato plants were transformed with the aid of *Agrobacterium*, as described in Rocha-Sosa et al. (EMBO J. 8, (1989), 23-29).

2. Transformation of Tomato Plants

Tomato plants were transformed with the aid of *Agrobacterium* according to the method described in U.S. Pat. No. 5,565,347.

3. Transformation of Rice Plants

Rice plants were transformed according to the method described by Hiei et al. (1994, Plant Journal 6(2), 271-282).

4. Determination of the Content of N-Acetylated Glucosamines

N-Acetylated glucosamine derivatives having a reducing end were determined similarly to the method of Elson and Morgan (1933, J. Biochem. 27, 1824) and the improved calorimetric determination method of Reissig et al. (1955, Biol. Chem. 217, 959-966). The calorimetric determination method is based on a reaction of chromogen III (Muckenschnabel et al., 1998, Cancer Letters 131, 13-20) with p-dimethylaminobenzaldehyde (DMAB, Ehrlich's reagent), yielding a red product whose concentration can be determined photometrically.

a) Work-Up of the Plant Material

First, harvested plant material was comminuted. Depending on the amount of plant material used, comminution was carried out in a laboratory oscillating ball mill (MM200, from Retsch, Germany) for 30 seconds at 30 Hz or using a Warring blender at maximum speed for about 30 seconds. In general, 0.5 g of the comminuted plant material (for example leaf, tuber or rice grain) was mixed with 1 ml of a solution consisting of 7% perchloric acid, 5 mM EGTA and incubated on ice for 20 minutes. The mixture was then centrifuged (5 minutes at 16 000×g, 4° C.). The supernatant obtained after centrifugation was taken off and neutralized using a solution consisting of 5M KOH, 1M TEA (adjusted pH 7.0) and then centrifuged again (5 min at 16 000×g, 4° C.). After the end of the centrifugation, the supernatant was taken off, its volume was determined and the amount of N-acetylated glucosamine derivatives having a reducing end was determined using the method described under b).

b) Determination of the Content of N-Acetylated Glucosamine Derivatives Having Reducing Ends 20 µl of a solution consisting of 0.8M $K_2B_4O_7$, pH 9.6, are added to 100 µl of the plant extract obtained by the method described under a) and, after thorough mixing, heated at 95° C. for 5 min. After cooling of the mixture to room temperature, 0.7 ml of Ehrlich's reagent (solution consisting of 10 g of DMAB in 12.5 ml of conc. HCl, 87.5 ml of glacial acetic acid, 1:10 diluted with glacial acetic acid) is added to the mixture, which is mixed again and incubated at 37° C. for a further 30 minutes. The mixture is then centrifuged at 16 000×g for 1 minute, and the optical density (OD) of the supernatant obtained after centrifugation is subsequently determined in a photometer at 585 nm.

c) Calculation of the Concentration of N-Acetylated Glucosamine Derivatives

First, a calibration curve was established using defined amounts of N-acetylglucosamine 6-phosphate. To this end, the OD of solutions comprising 0 mM, 0.1 mM, 0.5 mM, 1 mM, 5 mM and 10 mM of N-acetylglucosamine 6-phosphate was determined according to the method described under b).

The calibration curve was established in Microsoft Excel by fitting a second order polynomic trend/regression line of the formula $y=ax^2+bx+c$ or $y=x^2+px+q$ to the points measured for the individual concentrations. To calculate the values, the equation obtained was resolved for x, resulting in: $x=-p/2-\text{square root}(p^2/4-q)$, where $p=b/a$, $q=(c-y)/a$ and y is the measured OD of the unknown sample. Taking into account the fresh weight employed, the volume used and taking into account any dilution factor used, the contents were calculated in µmol (of the solution measured) or in µmol per g of fresh weight.

5. Isolation of Glucosaminoglycans from Plant Tissue Using the Example of Hyaluronan To detect the presence of hyaluronan and to determine the hyaluronan content in plant tissue, plant material was worked up as follows: 200 µl of water (demineralized, conductivity=18 MΩ) were added to about 0.3 g of leaf or tuber material, and the mixture was comminuted in a laboratory oscillating ball mill (MM200, from Retsch, Germany) (30 sec at 30 Hz). A further 800 µl of water (demineralized, conductivity=18 MΩ) were then added, and the mixture was mixed well (using, for example, a Vortex mixer). Cell debris and insoluble components were separated from the supernatant by centrifuging at 16 000×g for 5 minutes. An aliquot of the supernatant obtained was used to determine the amount of hyaluronan.

In the case of tomato fruits, in each case a whole ripe tomato fruit was worked up. To this end, the weight of the tomato fruit was determined, the tomato was comminuted in a Warring blender with a little water, the comminuted sample was freed from cell debris by centrifugation at 3600×g for 30 minutes and the volume of the extract was determined. An aliquot of the supernatant obtained was used to determine the amount of hyaluronan.

6. Purification of Glucosaminoglycans Using the Example of Hyaluronan

After addition of 100 ml of water (demineralized, conductivity=18 MΩ), about 100 grams of plant material were comminuted in a Warring blender at maximum speed for about 30 seconds. If relatively large parts of plants, such as, for example, tubers or tomato fruits, were used for isolation, they were cut beforehand into pieces of a size of about 1 $cm^3$. The cell debris was then removed using a tea sieve. The cell debris which had been separated off was once more suspended in 300 ml of water (demineralized, conductivity=18 MΩ) and again removed using a tea sieve. The two suspensions obtained (100 ml+300 ml) were combined and centrifuged at 13 000×g for 15 minutes. NaCl was added to the centrifugation supernatant obtained until a final concentration of 1% had been reached. After the NaCl had gone into solution, precipitation was carried out by addition of twice the volume of ethanol followed by thorough mixing and incubation at −20° C. overnight. The mixture was then centrifuged at 13 000×g for 15 minutes. The sedimented precipitate obtained after this centrifugation was dissolved in 100 ml of buffer (50 mM TrisHCl, pH 8, 1 mM $CaCl_2$) and proteinase K was then added to a final concentration of 100 μg/ml and the solution was incubated at 42° C. for 2 hours. This was followed by 10 minutes of incubation at 95° C. Once more, NaCl was added to this solution until a final concentration of 1% had been reached. After the NaCl had gone into solution, another precipitation was carried out by addition of twice the volume of ethanol, thorough mixing and incubation at −20° C. for about 96 hours. This was followed by 15 minutes of centrifugation at 13 000×g. The sedimented precipitate obtained after this centrifugation was dissolved in 30 ml of water (demineralized, conductivity=18 MΩ), and once more, NaCl was added to a final concentration of 1%. By adding twice the volume of ethanol, thorough mixing and incubation at −20° C. overnight, another precipitation was carried out. The precipitate obtained after subsequent centrifugation at 13 000×g for 15 minutes was dissolved in 20 ml of water (demineralized, conductivity=18 MΩ).

Further purification was carried out by centrifugal filtration. To this end, in each case 5 ml of the dissolved precipitate were applied to a membrane filter (CentriconAmicon, pore width 10 000 NMWL, Prod. No. UCF8 010 96), and the sample was centrifuged at 2200×g until only about 3 ml of the solution above the filter remained. Two more times, in each case 3 ml of water (demineralized, conductivity=18 MΩ) were then added to the solution above the membrane and in each case re-centrifuged under identical conditions until, at the end, only about 3 ml of the solution above the filter remained. The solutions still present above the membrane after centrifugal filtration were taken off, and the membrane was rinsed repeatedly (three to five times) with about 1.5 ml of water (demineralized, conductivity=18 MΩ). All solutions which were still present above the membrane and the solutions obtained from rinsing were combined, NaCl was added to a final concentration of 1%, after the NaCl had gone into solution, twice the volume of ethanol was added, the sample was mixed and a precipitate was obtained by storage at −20° C. overnight. The precipitate obtained after subsequent centrifugation at 13 000×g for 15 minutes was dissolved in 4 ml of water (demineralized, conductivity=18 MΩ) and then freeze-dried (24 hours under a pressure of 0.37 mbar, freeze drying apparatus Christ Alpha 1-4, from Christ, Osterode, Germany).

7. Detection of Hyaluronan and Determination of the Hyaluronan Content

Hyaluronan was detected using a commercial test (Hyaluronic Acid (HA) test kit from Corgenix, Inc., Colorado, USA, Prod. No. 029-001) according to the instructions of the manufacturer which are herewith incorporated into the description by way of reference. The test principle is based on the availability of a protein which binds specifically to hyaluronan (HABP) and is carried out similarly to an ELISA, where a color reaction indicates the hyaluronan content in the sample examined. Accordingly, for the quantitative determination of hyaluronan, the samples to be measured should be employed in a concentration such that it is within the stated limits (for example: dilution of the sample in question or use of less water for extracting hyaluronan from plant tissue, depending on whether a limit was exceeded or not reached).

8. Determination of the Activity of a GFAT

The activity of a protein having the activity of a GFAT is determined as described in Rachel et al. (1996, J. Bacteriol. 178 (8), 2320-2327).

To distinguish whether a protein has the activity of a GFAT-1 or GFAT-2, the method described in Hu et al. (2004, J. Biol. Chem. 279 (29), 29988-29993) is used.

9. Detection of N-Acetylated Glucosamine Derivatives by Mass Spectroscopy

To detect N-acetylated glucosamine derivatives by mass spectroscopy, plant tissue was worked up as under General Methods Item 4 a). To obtain an extract as free of salt as possible, the respective samples were, prior to the examination by mass spectroscopy, initially frozen at −20° C. and thawed during centrifugation (16 000×g at room temperature). For the measurement, the supernatant was diluted 1:20 with a methanol:water mixture in a ratio of 1:1 (volume/volume).

To increase the detection sensitivity for weak signals (peaks), MS spectra with three different detector sensitivities were recorded. However, in this case the response of the detector is no longer linear, which is noted when the signal intensities (peak areas) of different metabolites are compared and which should be taken into account. To ensure that the measurements can be compared with one another, it was ensured that the individual samples gave identical signal intensities (in cps, counts per second) at the same detector setting.

The areas of the resulting signals (peak areas) assigned to the different metabolites are stated relatively to the peak area of hexoses (m/z=179) in %. The ratio of the signal intensities (peak areas) in different samples can be used to infer the concentration ratios of the corresponding N-acetylated glucosamine derivatives in relation to the concentration of hexoses in the sample in question.

MS-MS measurements of the individual samples and of individual corresponding reference substances (glucosamine, N-acetyl glucosamine, glucosamine 6-phosphate glucosamine 1-phosphate, N-acetylglucosamine 6-phosphate, N-acetylglucosamine 1-phosphate, UDP-N-acetylglucosamine) were carried out in parallel. In this way, it is possible to assess whether the signal (peak) used for determining the area is a signal generated exclusively by a specific metabolite or by specific isomeric metabolites having the same mass, or whether the signal in question can be assigned only partially to the corresponding metabolite or the corresponding specific isomeric metabolites having the same mass.

MS and MS-MS spectra were recorded in the negative mode using a Q-STAR Pulsar i hybrid mass spectrometer from Applied Biosystems fitted with a nano-electrospray source. The ions detected were mainly deprotonated ions with a single charge.

The measurements were carried out under the following conditions:

| | |
|---|---|
| Mass range | 50-700 Da. |
| Detector sensitivity: | 2000, 2050 and 2100. |

For each of the three detector settings, it was ensured that the samples had similar signal intensities (in cps, counts per second).

EXAMPLES

1. Acquisition of Nucleic Acid Sequences Coding for a Protein Having the Activity of a GFAT-1 from the Mouse The nucleic acid sequence coding for a protein having the activity of a GFAT-1 (glutamine:fructose 6-phosphate amidotransferase or glucosamine 6-phosphate synthase, EC 2.6.1.16) was purchased from BioCat GmbH, Heidelberg, Germany (Art. No. MMM1013-65346, cDNA clone MGC: 58262, IMAGE:6742987). This is a clone which is produced by the I.M.A.G.E. consortium and distributed by BioCat GmbH. The cDNA coding for a protein having the activity of a GFAT-1 was cloned into the vector pCMV Sport 6 from Invitrogen. The plasmid was named IC 365-256. The nucleic acid sequence coding for the protein having the activity of a GFAT-1 from Mus musculus is shown under SEQ ID NO 4.

To facilitate subsequent cloning steps, the coding sequence of the GFAT-1 was excised using Xho I and Eco RV from the plasmid IC 365-256 and cloned into the plasmid pME9, which had been cut with the same restriction endonucleases. The plasmid obtained was named IC 367-256.

The plasmid pME9 is a pBlueSkript vector from Stratagene (Prod. No. 212207) where, in contrast to the pBlueSkript vector mentioned, pME9 contains a modified Multiple Cloning Site (MCS) which, in addition to the MCS present in the pBlueSkript vector, has an additional Pac I restriction site at both ends of the MCS.

2. Acquisition of a Nucleic Acid Sequence Coding for a Protein Having the Activity of a GFAT-2 from a Mouse The nucleic acid sequence coding for a protein having the activity of a GFAT-2 (glutamine:fructose 6-phosphate amidotransferase or glucosamine 6-phosphate synthase, EC 2.6.1.16) was purchased from Invitrogen (Clone ID 4167189, cDNA clone MGC:18324, IMAGE:4167189). This is a clone produced by the I.M.A.G.E. consortium and distributed by Invitrogen. The cDNA coding for a protein having the activity of a GFAT-2 was cloned into the vector pCMV Sport 6 from Invitrogen. The plasmid was named IC 369-256. The nucleic acid sequence coding for the protein having the activity of a GFAT-2 from Mus musculus is shown under SEQ ID NO 6.

3. Synthesis of the Nucleic Acid Sequences Coding for a Protein Having the Activity Of a Bacterial GFAT from Escherichia coli The nucleic acid sequence coding for a protein having the activity of a bacterial GFAT (glutamine:fructose 6-phosphate amidotransferase or glucosamine 6-phosphate synthase, glms, EC 2.6.1.16) from Escherichia coli was synthesized by Entelechon GmbH and cloned into the vector pCR4Topo from Invitrogen (Prod. No. K4510-20). The plasmid obtained was named IC 373-256. The synthetic nucleic acid sequence coding for the protein having the activity of a bacterial GFAT from Escherichia coli is shown under SEQ ID NO 10. The corresponding nucleic acid sequence originally isolated from Escherichia coli is shown under SEQ ID NO 8.

4. Synthesis of Nucleic Acid Molecules Coding for a Hyaluronan Synthase of Paramecium Bursaria Chlorella Virus 1

The nucleic acid sequence coding for a hyaluronan synthase of Paramecium bursaria Chlorella Virus 1 was synthesized by Medigenomix GmbH (Munich, Germany) and cloned into the vector pCR2.1 from Invitrogen (Prod. No. K2000-01). The plasmid obtained was named IC 323-215. The synthetic nucleic acid sequence coding for the HAS protein from Paramecium bursaria Chlorella Virus 1 is shown under SEQ ID NO 3. The corresponding nucleic acid sequence originally isolated from Paramecium bursaria Chlorella Virus 1 is shown under SEQ ID NO 1.

5. Synthesis of Nucleic Acid Molecules Coding for a Protein Having the Activity of a UDP-Glucose Dehydrogenase of Paramecium Bursaria Chlorella Virus 1

The nucleic acid sequence coding for a protein having the activity of a UDP-glucose dehydrogenase from Paramecium bursaria Chlorella Virus 1 was synthesized by Entelechon GmbH and cloned into the vector pCR4Topo from Invitrogen (Prod. No. K4510-20). The plasmid obtained was named IC 339-222. The synthetic nucleic acid sequence coding for the protein having the activity of a UDP-glucose dehydrogenase from Paramecium bursaria Chlorella Virus 1 is shown under SEQ ID NO 13. The corresponding nucleic acid sequence originally isolated from Paramecium bursaria Chlorella Virus 1 is shown under SEQ ID NO 11

6. Preparation of the Plant Expression Vector IR 47-71

The plasmid pBinAR is a derivative of the binary vector plasmid pBin19 (Bevan, 1984, Nucl Acids Res 12: 8711-8721) which was constructed as follows:

A 529 bp fragment comprising the nucleotides 6909-7437 of the 35S promoter of the cauliflower mosaic virus was isolated as EcoR I/Kpn I fragment from the plasmid pDH51 (Pietrzak et al, 1986 Nucleic Acids Res. 14, 5858) and ligated between the EcoR I and Kpn I restriction sites of the polylinker of pUC18. This gave the plasmid pUC18-35S. With the aid of the restriction endonucleases Hind III and Pvu II, a 192 bp fragment comprising the polyadenylation signal (3'-terminus) of the octopin synthase gene (Gen 3) of the T-DNA of the Ti plasmid pTiACH5 (Gielen et al, 1984, EMBO Journal 3, 835-846) (nucleotides 11749-11939) was isolated from the plasmid pAGV40 (Herrera-Estrella et al, 1983 Nature, 303, 209-213). After addition of Sph I linkers to the Pvu II restriction site, the fragment was ligated between the Sph I and Hind III restriction sites of pUC18-35S. This gave the plasmid pA7. From this plasmid, the entire polylinker comprising the 35S promoter and the OCS terminator was excised with EcoR I and Hind III and ligated into the appropriately cut vector pBin19. This gave the plant expression vector pBinAR (Höfgen and Willmitzer, 1990, Plant Science 66, 221-230).

The promoter of the Patatin gene B33 from Solanum tuberosum (Rocha-Sosa et al., 1989, EMBO J. 8, 23-29) was ligated as Dra I fragment (nucleotides-1512-+14) into the vector pUC19, which had been cut with Sst I and whose ends had been blunted with the aid of T4-DNA polymerase. This gave the plasmid pUC19-B33. Using EcoR I and Sma I, the B33 promoter was excised from this plasmid and ligated into the appropriately cut vector pBinAR. This gave the plant expression vector pBinB33.

To facilitate further cloning steps, the MCS (Multiple Cloning Site) was widened. To this end, two complementary oligonucleotides were synthesized, heated at 95° C. for 5 minutes and slowly cooled to room temperature, and the double-stranded fragment obtained was cloned into the Sal I and Kpn I restriction sites of pBinB33. The oligonucleotides used for this purpose had the following sequence:

```
5'-TCG ACA GGC CTG GAT CCT TAA TTA AAC TAG TCT CGA
GGA GCT CGG TAC-3' (SEQ ID NO: 14)
5'-CGA GCT CCT CGA GAC TAG TTT AAT TAA GGA TCC AGG
CCT G-3' (SEQ ID NO: 15)
```

The plasmid obtained was named IR 47-71.

7. Preparation of the Plant Expression Vector pBinARHyg

Using the restriction endonucleases EcoR I and Hind III, the fragment comprising the 35S promoter, the OCS terminator and the entire multiple cloning site was excised from the plasmid pA7 and cloned into the vector pBIBHyg (Becker, 1990, Nucleic Acids Res. 18, 203) which had been cut with the same restriction endonucleases. The plasmid obtained was named pBinARHyg.

8. Preparation of the Cloning Vector IC 317-204

Nucleic acid fragments comprising the OCS terminator were isolated from the plasmid IR 47-71 using the restriction endonucleases Xho I and Hind III and cloned into the vector pBlueScript KS (from Stratagene, Prod. No. 212207), which had been cut with the same restriction endonucleases. The plasmid obtained was named IC 306-204.

Nucleic acid fragments comprising the B33 promoter were isolated from the plasmid IR 47-71 using the restriction endonucleases Bam HI and Eco RI and cloned into the vector pBlueScript KS (from Stratagene, Prod. No. 212207), which had been cut with the same restriction endonucleases. The plasmid obtained was named IC 314-204.

From IC 306-204, the OCS terminator was isolated using the restriction endonuclease Bam HI and cloned into the plasmid IC 314-204, which had been cut with the same restriction endonuclease. The plasmid obtained was named IC 317-204.

9. Preparation of the Plant Expression Vector IC 341-222 Comprising a Coding Nucleic Acid Sequence for a Hyaluronan Synthase of Paramecium Bursaria *Chlorella* Virus 1

By restriction digestion with BamH I and Xho I, nucleic acid molecules comprising the coding sequence of hyaluronan synthase were isolated from the plasmid IC 323-215 and cloned into the BamH I and Xho I restriction sites of the plasmid IR 47-71. The plant expression vector obtained was named IC 341-222.

10. Preparation of the Plant Expression Vectors 349-222 Comprising Coding Nucleic Acid Sequences for a Protein Having the Activity of a UDP-Glucose Dehydrogenase from *Paramecium Bursaria Chlorella* Virus 1

Using restriction digestion with BamH I and Kpn I, nucleic acid molecules comprising the coding sequence for a protein having the activity of a UDP-glucose dehydrogenase from *Paramecium bursaria Chlorella* Virus 1 were isolated from the plasmid IC 339-222 and cloned into the plasmid pA7, which had been cut with the same restriction endonucleases. The plasmid obtained was named IC 342-222.

By restriction digestion with Xba I and Kpn I, nucleic acid molecules comprising the coding sequence for a protein having the activity a UDP-glucose dehydrogenase from *Paramecium bursaria Chlorella* Virus 1 were isolated from the plasmid IC 342-222 and cloned into the expression vector pBinAR Hyg, which had been cut with Xba I and Kpn I. The plasmid obtained was named IC 349-222.

11. Preparation of the Plant Expression Vectors IC 376-271 Comprising Coding Nucleic Acid Sequences for a Protein Having the Activity of a GFAT-1 from the Mouse and for a Protein Having the Activity of a UDP-Glucose Dehydrogenase from *Paramecium bursaria Chlorella* Virus 1

A nucleic acid fragment comprising the B33 promoter and the OCS terminator, which fragment had been isolated from IC 317-204 by restriction digestion using Eco RI, was cloned into the Eco RI restriction site of the plasmid IC 349-222. Here, head-to-head orientation of the promoters (25S and B33) was ensured. The vector obtained was named IC 354-222.

To obtain a plant expression vector comprising a nucleic acid sequence coding for a protein having the activity of a GFAT-1 from the mouse, the coding sequence of the protein having the activity of a GFAT-1 from the mouse was isolated by restriction digestion with Xho I and Eco RV from IC 365-256 and cloned into the plasmid IC 354-222, which had been cut with Xho I and Ecl136 II. The plant expression vector obtained was named IC 376-256.

12. Preparation of the Plant Expression Vector IC 372-256 Comprising Coding Nucleic Acid Sequences for a Protein Having the Activity of a GFAT-2 from the Mouse and for a Protein Having the Activity of a UDP-Glucose Dehydrogenase from *Paramecium bursaria Chlorella* Virus 1

A nucleic acid fragment comprising the coding sequence of the protein having the activity of a GFAT-2 from the mouse was isolated from IC 369-256 by restriction digestion with Xho I and Eco RV and cloned into the plasmid IC 354-222, which had been cut with Xho I and Ecl136 II. The plant expression vector obtained was named IC 372-256.

13. Preparation of the Plant Expression Vector 375-271 Comprising Coding Nucleic Acid Sequences for a Protein Having the Activity of a GFAT from *Escherichia coli* and for a Protein Having the Activity of a UDP-Glucose Dehydrogenase from *Paramecium bursaria Chlorella* Virus 1

A nucleic acid fragment comprising the coding sequence of the protein having the activity of a GFAT from *Escherichia coli* was isolated from IC 373-256 by restriction digestion with Xho I and Eco RV and cloned into the plasmid IC 354-222, which had been cut with Xho I and Ecl136 II. The plant expression vector obtained was named IC 375-271.

14. Preparation of the Plant Expression Vector IC 398-311 Comprising a Coding Nucleic Acid Sequence for a Protein Having the Activity of a GFAT from *Escherichia coli*

By restriction digestion with Ecl 136 I and Xho I, the coding sequence of the protein having the activity of a bacterial GFAT from *E. coli* was isolated from the plasmid IC 373-256 and ligated into the Sma I and Sal I restriction sites of the vector pBinAR Hyg. The plant expression vector obtained was named IC 398-311.

15. Preparation of the Plant Expression Vector IC 386-299

By PCR using genomic DNA isolated from leaves of rice (*Oryza sativa*, cultivar M202) using DNA polymerase (Expand High Fidelity PCR Systems, Roche Prod. No. 1732641), the DNA of the prolamin promoter from rice (EMBL Accession NO D63901, Sha et al., 1996, Biosci. Biotech. Biochem. 60, 335-337, Wu et al., 1998. Plant Cell Physiol. 39(8), 885-889) was isolated. The amplicon obtained from this PCR reaction was cloned into the vector pCR 2.1 using the TA cloning kit (Invitrogen Prod. No.: KNM2040-01). The plasmid obtained was named MI 4-154. Conditions used for the amplification of the DNA coding for the prolamin promoter:

The conditions and buffers stated by the manufacturer and 50 ng of total DNA were used.

```
0.83 µM dNTP mix
0.25 µM Primer prol-F1
5'-AAAAACTAGTTCTACATCGGCTTAGGTGTAGCAACACG
(SEQ ID NO: 16)

0.25 µM primer prol-R1
5'-AAAAGATATCTGTTGTTGGATTCTACTACTATGCTTCAA
(SEQ ID NO: 17)
```

Reaction conditions:

| | | |
|---|---|---|
| Step 1 | 94° C. | 15 sec |
| Step 2 | 60° C. | 15 sec |
| Step 3 | 72° C. | 45 sec |

First, the reaction according to steps 1 to 3 was carried out using 35 repetitions (cycles). After the reaction had ended, the reaction mixture was cooled to 4° C. Subsequent cloning into the vector pCR 2.1 using the TA cloning kit (Invitrogen Prod. No.: KNM2040-01) was carried out following the conditions stated by the manufacturer. The plasmid comprising the prolamin promoter from rice was named MI 4-154.

A nucleic acid fragment comprising the coding sequence of the protein having the activity of a GFAT-2 from the mouse was isolated by restriction digestion using the restriction endonucleases Not I and Kpn I from the plasmid IC 369-256 and cloned into the vector pMCS5 (purchased from MoBiTec), which had been digested with Not I and Kpn I. The plasmid obtained was named IC 385-299. In the next step, the nucleic acid fragment comprising the coding sequence of the protein having the activity of a GFAT-2 from the mouse was isolated by restriction digestion with the restriction endonucleases Xho I and Hpa I from IC 385-299 and cloned into the plasmid MI 9-154, which had been cut with Xho I and Ecl136 II. The plant expression vector obtained was named IC 386-299. Starting vector for the preparation of the vector MI 9-154 is the plasmid ML 18-56 (WO 05/030941). An MCS synthesized by two oligonucleotides and having the appropriate sticky ends and comprising the restriction sites Pst I, Sac I, Bln I, Xho I, Hpa I, Spe I and Hind III was introduced into the plasmid ML 18-56, which had been digested with Hind III and Pst I. The vector obtained was named MI 8-154.

By digestion with Eco RV and Spe I, the prolamin promoter was isolated from MI 4-154 and ligated into the vector MI 8-154, which had been digested with Hpa I and Spe I. The vector obtained was named MI 9-154.

16. Potato Plants Comprising a Nucleic Acid Molecule Coding for a Protein Having the Activity of a Bacterial GFAT a) Transformation of Potato Plants Potato plants (cultivar Désirée) were transformed by the method given in General Methods Item 1 using the plant expression vector IC 398-311, which comprises a coding nucleic acid sequence for a protein having the activity of a bacterial GFAT from *Escherichia coli* under the control of the promoter of the patatin gene B33 from *Solanum tuberosum* (Rocha-Sosa et al., 1989, EMBO J. 8, 23-29). The transgenic lines obtained, which are transformed with the plasmid IC 398-311, were named 432 ES.

b) Analysis of Lines 432 ES

Plants of the line 432 ES were cultivated in a greenhouse in soil in 6 cm pots. In each case about 0.3 g to 0.8 g of leaf material, harvested from individual plants, was worked up according to the method described under General Methods Item 4, and the content of N-acetylated glucosamine derivatives was determined. For individual plants having an increased content of N-acetylated glucosamine derivatives, the following results were obtained:

TABLE 1

Amount of N-acetylated glucosamine derivatives (in µmol per gram of fresh weight) measured in leaves of independent transgenic plants of the line 432 ES.

| Plant | µmol/g FW |
|---|---|
| 432ES 1 | 2.97 |
| 432ES 2 | 0.51 |
| 432ES 4 | 2.19 |
| 432ES 5 | 3.99 |
| 432ES 6 | 6.20 |
| 432ES 7 | 2.98 |
| 432ES 8 | 0.48 |
| 432ES 9 | 11.48 |
| 432ES 10 | 0.30 |
| 432ES 11 | 6.89 |
| 432ES 12 | 5.45 |
| 432ES 13 | 0.23 |
| 432ES 14 | 0.80 |
| 432ES 15 | 1.75 |
| 432ES 16 | 4.87 |
| 432ES 18 | 3.38 |
| 432ES 19 | 6.38 |
| 432ES 21 | 1.42 |
| 432ES 22 | 9.73 |
| 432ES 23 | 5.88 |
| 432ES 25 | 4.45 |
| 432ES 26 | 1.81 |
| 432ES 27 | 1.75 |
| 432ES 28 | 0.45 |
| 432ES 32 | 4.56 |
| 432ES 33 | 3.64 |
| 432ES 35 | 3.64 |
| 432ES 37 | 6.67 |
| 432ES 38 | 0.95 |
| 432ES 40 | 8.69 |
| 432ES 42 | 1.47 |
| 432ES 43 | 5.41 |
| 432ES 44 | 6.33 |
| 432ES 45 | 3.39 |
| wt 1 | 0.05 |
| wt 2 | 0.26 |
| wt 3 | 0.17 |

Column 1 refers in each case to the plant, independently obtained from the transformation, from which the material was harvested ("wt" refers to plants which have not been transformed).

These results show that plants having a foreign nucleic acid molecule coding for a protein having the activity of a bacterial GFAT have a considerably higher content of N-acetylated glucosamine derivatives than correspondingly non-transformed wild-type plants.

17. Rice Plants Comprising a Nucleic Acid Molecule Coding for a Protein Having the Activity of a GFAT-2 a) Transformation of Rice Plants

Rice plants (variety M202) were transformed according to the method given under General Methods Item 3 with the plant expression vector IC 386-299, which comprises a coding nucleic acid sequence for a protein having the activity of a GFAT-2 from the mouse under the control of the promoter of the 13 kDa prolamin polypeptide. The transgenic lines obtained, which are transformed with the plasmid IC 386-299, were named GAOS0788.

b) Analysis of the Lines GAOS0788

Independent plants, originating from the transformation with the plasmid IC 386-299, of the line GAOS0788 were cultivated in soil in a greenhouse. From each plant, about 20-25 ripe seeds (grains) were harvested, the husks were removed with a dehusker (Laboratory Paddy sheller, Grainman, Miami, Fla., USA) and about 7 brown rice seeds (pools) of each line were comminuted in a laboratory oscillating ball mill (MM200, from Retsch, Germany, 30 sec at 30 Hz), resulting in a flour. Using the method described under General Methods Item 4, the content of N-acetylated glucosamine derivatives was then determined. For individual plants having an increased content of N-acetylated glucosamine derivatives, the following results were obtained:

TABLE 2

Amount of N-acetylated glucosamine derivatives (in μmol per gram of fresh weight) measured in pools of ripe seeds of independent transgenic plants of the line GAOS0788.

| Plant | μmol/g FW |
|---|---|
| GAOS0788-00101 | 14.50 |
| GAOS0788-00202 | 17.36 |
| GAOS0788-00301 | 14.46 |
| GAOS0788-00501 | 23.07 |
| GAOS0788-00602 | 7.75 |
| GAOS0788-00701 | 4.44 |
| GAOS0788-00802 | 17.43 |
| GAOS0788-00901 | 10.13 |
| GAOS0788-01001 | 6.38 |
| GAOS0788-01202 | 8.32 |
| GAOS0788-01401 | 8.64 |
| GAOS0788-01502 | 2.97 |
| GAOS0788-01602 | 8.15 |
| GAOS0788-01701 | 16.50 |
| GAOS0788-02002 | 5.65 |
| GAOS0788-02202 | 5.15 |
| GAOS0788-02301 | 7.82 |
| GAOS0788-02401 | 20.89 |
| GAOS0788-02501 | 6.67 |
| GAOS0788-02601 | 7.34 |
| GAOS0788-02701 | 4.31 |
| GAOS0788-02802 | 8.02 |
| GAOS0788-02901 | 4.74 |
| GAOS0788-03001 | 4.36 |
| GAOS0788-03101 | 11.83 |
| GAOS0788-03202 | 2.76 |
| GAOS0788-03302 | 12.82 |
| Control | n.d. |
| Control | n.d. |

Column 1 refers to the plant, independently obtained from the transformation, from which material was harvested (here, "control" refers to plants transformed with a plasmid having no nucleic acid molecule coding for a protein having the activity of a GFAT. Non-detectable amounts are marked "n.d.".

c) Analysis of Individual Seeds of the Plants GAOS0788-02401 and GAOS0788-00501

The seeds harvested in Example b) originated from plants obtained directly after transformation, which plants were thus heterozygotic with respect to the respective integration sites of the T-DNAs in question. Accordingly, as a result of Mendel's laws of inheritance, the seed pools analyzed contained seeds comprising various amounts of the T-DNAs in question, it also being possible for individual seeds not having any T-DNAs integrated by transformation to be present in the respective pools. Thus, single, individual brown seeds from the plants of the line GAOS0788-02401 and plants of the line GAOS0788-00501 were each examined by the method described under General Methods Item 4 for their content of N-acetylated glucosamine derivatives. The following results were obtained:

TABLE 3

Amount of N-acetylated glucosamine derivatives (in μmol per gram of fresh weight) of individual seeds of the plants from lines GAOS0788-02401 and GAOS0788-00501.

| Sample | μmol/g FW |
|---|---|
| GAOS0788-02401 seed 1 | n.d |
| GAOS0788-02401 seed 2 | 22.41 |
| GAOS0788-02401 seed 3 | 38.47 |
| GAOS0788-02401 seed 4 | 16.57 |
| GAOS0788-02401 seed 5 | 17.67 |
| GAOS0788-02401 seed 6 | 3.79 |
| GAOS0788-02401 seed 7 | 10.14 |
| GAOS0788-02401 seed 8 | 18.70 |
| GAOS0788-00501 seed 1 | n.d |
| GAOS0788-00501 seed 2 | 17.20 |
| GAOS0788-00501 seed 3 | 19.89 |
| GAOS0788-00501 seed 4 | 15.47 |
| GAOS0788-00501 seed 5 | 9.31 |
| GAOS0788-00501 seed 6 | 20.88 |
| GAOS0788-00501 seed 7 | 25.31 |
| GAOS0788-00501 seed 8 | 31.92 |
| GAOS0788-00501 seed 9 | 28.82 |
| GAOS0788-00501 seed 10 | 43.35 |
| Control seed 1 | n.d |
| Control seed 2 | n.d |
| Control seed 3 | n.d |
| Control seed 4 | n.d |

In each case, column 1 refers to the plant, independently obtained from the transformation, from which individual seeds were harvested and analyzed (here, "control" refers to seeds of plants transformed with a construct comprising no nucleic acid molecule coding for a protein having the activity of a GFAT). Non-detectable amounts are marked "n.d.".

The results obtained show that flours from seeds (grains) of rice plants having a nucleic acid molecule coding for a protein having the activity of a GFAT-2 have a considerably higher content of N-acetylated glucosamine derivatives compared to flours produced from plants having no nucleic acid molecule coding for a protein having the activity of a GFAT-2.

18. Synthesis of N-Acetylated Glucosamine Derivatives in Tomato Plants Transformed with Nucleic Acid Molecules Coding for Various Isoforms of a Protein Having the Activity of a GFAT a) Production of Tomato Plants Comprising a Foreign Nucleic Acid Molecule Coding For a Protein Having the Activity of a GFAT-1

Tomato plants (cultivar Moneymaker) were transformed by the method given under General Methods Item 2 with the plant expression vector IC 376-271, which comprises a coding nucleic acid sequence for a protein having the activity of a UDP-glucose dehydrogenase and a foreign nucleic acid molecule coding for a protein having the activity of a GFAT-1. The transgenic lines obtained, which are transformed with the plasmid 376-271, were named 420 ES. Proteins having the activity of a UDP-glucose dehydrogenase catalyze the synthesis of UDP-GlcA from UDP-glucose. In addition to GlcNAc, some glucosaminoglycan synthases, such as, for example, hyaluronan synthase, require UDP-GlcA as substrate.

b) Analysis of the Lines 420 ES

Plants of the line 420 ES were cultivated in hydroculture in pots in a greenhouse. In each case about 5 g of plant material, harvested from individual plants, were worked up using the method described under General Methods Item 4, and the content of N-acetylated glucosamine derivatives was determined. Here, per plant, a plurality of independent measurements were carried out for each worked-up sample. The following results were obtained for individual plants:

TABLE 4

Amount of N-acetylated glucosamine derivatives (in µmol per gram of fresh weight) measured in leaves of independent transgenic plants of the line 420 ES.

| Plant | µmol/g FW | Mean [µmol/g FW] |
|---|---|---|
| 420ES 1 a | 0.15 | 0.15 |
| 420ES 1 b | 0.10 | |
| 420ES 1 c | 0.15 | |
| 420ES 2 a | 0.11 | 0.10 |
| 420ES 2 b | 0.09 | |
| 420ES 2 c | 0.10 | |
| 420ES 3 a | 0.29 | 0.28 |
| 420ES 3 b | 0.30 | |
| 420ES 3 c | 0.25 | |
| 420ES 4 a | 0.20 | 0.18 |
| 420ES 4 b | 0.19 | |
| 420ES 4 c | 0.16 | |
| 420ES 5 a | 0.10 | 0.09 |
| 420ES 5 b | 0.08 | |
| 420ES 5 c | 0.09 | |
| 420ES 6 a | 0.24 | 0.27 |
| 420ES 6 c | 0.29 | |
| 420ES 7 b | 1.12 | 1.31 |
| 420ES 7 c | 1.50 | |
| 420ES 8 a | 0.05 | 0.06 |
| 420ES 8 b | 0.05 | |
| 420ES 8 c | 0.06 | |
| 420ES 9 a | 0.02 | 0.02 |
| 420ES 9 b | 0.01 | |
| 420ES 9 c | 0.02 | |
| 420ES 10 a | 0.05 | 0.04 |
| 420ES 10 b | 0.03 | |
| 420ES 10 c | 0.05 | |
| 420ES 11 a | 0.06 | 0.06 |
| 420ES 11 b | 0.10 | |
| 420ES 11 c | 0.03 | |
| 420ES 12 a | 0.09 | 0.08 |
| 420ES 12 b | 0.06 | |
| 420ES 13 a | 0.02 | 0.02 |
| 420ES 13 b | 0.01 | |
| 420ES 13 c | 0.03 | |
| 420ES 14 a | 0.02 | 0.03 |
| 420ES 14 b | 0.04 | |
| 420ES 14 c | 0.04 | |
| 420ES 15 a | 0.05 | 0.06 |
| 420ES 15 b | 0.06 | |
| 420ES 15 c | 0.06 | |
| 420ES 16 a | 0.08 | 0.07 |
| 420ES 16 b | 0.06 | |
| 420ES 16 c | 0.07 | |
| 420ES 17 a | 0.08 | 0.07 |
| 420ES 17 b | 0.07 | |
| 420ES 17 c | 0.08 | |
| 420ES 18 a | 0.07 | 0.08 |
| 420ES 18 b | 0.09 | |
| 420ES 18 c | 0.09 | |
| 420ES 19 a | 0.03 | 0.03 |
| 420ES 19 b | 0.00 | |
| 420ES 19 c | 0.05 | |
| 420ES 20 a | 0.04 | 0.06 |
| 420ES 20 b | 0.07 | |
| 420ES 20 c | 0.05 | |
| 420ES 22 a | 0.08 | 0.08 |
| 420ES 22 b | 0.07 | |
| 420ES 22 c | 0.08 | |
| 420ES 23 a | 0.14 | 0.13 |
| 420ES 23 b | 0.11 | |
| 420ES 23 c | 0.13 | |
| 420ES 24 a | 0.05 | 0.05 |
| 420ES 24 b | 0.04 | |
| 420ES 24 c | 0.05 | |
| 420ES 25 a | 0.05 | 0.06 |
| 420ES 25 b | 0.07 | |
| 420ES 25 c | 0.06 | |
| 420ES 26 a | 0.13 | 0.09 |
| 420ES 26 b | 0.06 | |
| 420ES 26 c | 0.08 | |
| 420ES 27 a | 0.09 | 0.08 |
| 420ES 27 b | 0.10 | |
| 420ES 27 c | 0.05 | |
| 420ES 28 a | 0.01 | 0.01 |
| 420ES 28 b | 0.02 | |
| 420ES 28 c | 0.01 | |
| 420ES 29 a | 0.09 | 0.08 |
| 420ES 29 b | 0.07 | |
| 420ES 29 c | 0.07 | |
| 420ES 30 a | 0.04 | 0.03 |
| 420ES 30 b | 0.03 | |
| 420ES 30 c | 0.01 | |
| wt 7 a | 0.09 | 0.10 |
| wt 7 b | 0.11 | |
| wt 7 c | 0.09 | |
| wt 12 a | 0.02 | 0.01 |
| wt 12 b | n.d | |
| wt 12 c | 0.03 | |

Column 1 refers to the plant, independently originating from the transformation, from which the material was harvested (here, "wt" refers to non-transformed plants). The extension of the names of the plants by a, b or c denotes independent measurements carried out for the worked-up sample in question.
Non-detectable amounts are marked "n.d.".

These results show that plants having a foreign nucleic acid molecule coding for a protein having the activity of a GFAT-1 and coding for a protein having the activity of a UDP-glucose dehydrogenase have a content of N-acetylated glucosamine derivatives which is slightly higher than that of corresponding non-transformed wild-type plants.

c) Production of Tomato Plants Comprising a Foreign Nucleic Acid Molecule Coding for a Protein Having the Activity of a GFAT-2

Tomato plants (cultivar Moneymaker) were transformed by the method given under General Methods Item 2 with the plant expression vector IC 372-256 comprising a coding nucleic acid sequence for a protein having the activity of a UDP-glucose dehydrogenase and a foreign nucleic acid molecule coding for a protein having the activity of a GFAT-2. The transgenic lines obtained, which are transformed with the plasmid IC 372-256, were named 421 ES.

d) Analysis of Lines 421 ES

Plants of the line 421 ES were cultivated in hydroculture in pots in a greenhouse. In each case about 5 g of plant material, harvested from individual plants, were worked up using the method described under General Methods Item 4, and the content of N-acetylated glucosamine derivatives was determined. Here, per plant, a plurality of independent measurements were carried out for each worked-up sample. The following results were obtained for individual plants:

TABLE 5

Amount of N-acetylated glucosamine derivatives (in μmol per gram of fresh weight) measured in leaves of independent transgenic plants of the line 421 ES.

| Plant | μmol/g FW | Mean [μmol/g FW] |
|---|---|---|
| 421ES 1 a | 0.60 | 0.67 |
| 421ES 1 b | 0.61 | |
| 421ES 1 c | 0.80 | |
| 421ES 3 a | 1.07 | 1.10 |
| 421ES 3 b | 1.07 | |
| 421ES 3 c | 1.17 | |
| 421ES 4 a | 2.22 | 2.00 |
| 421ES 4 b | 1.88 | |
| 421ES 4 c | 1.89 | |
| 421ES 5 a | 0.79 | 0.87 |
| 421ES 5 b | 1.07 | |
| 421ES 5 c | 0.74 | |
| 421ES 6 a | 0.62 | 0.74 |
| 421ES 6 b | 0.76 | |
| 421ES 6 c | 0.85 | |
| 421ES 7 a | 1.20 | 1.01 |
| 421ES 7 b | 1.01 | |
| 421ES 7 c | 0.84 | |
| 421ES 9 a | 0.35 | 0.40 |
| 421ES 9 b | 0.36 | |
| 421ES 9 c | 0.48 | |
| 421ES 10 a | 0.08 | 0.16 |
| 421ES 10 b | 0.18 | |
| 421ES 10 c | 0.22 | |
| 421ES 11 a | 2.96 | 2.78 |
| 421ES 11 b | 2.61 | |
| 421ES 11 c | 2.78 | |
| 421ES 12 a | 1.13 | 0.96 |
| 421ES 12 b | 0.82 | |
| 421ES 12 c | 0.93 | |
| 421ES 19 a | 0.04 | 0.04 |
| 421ES 19 b | 0.03 | |
| 421ES 21 a | 0.21 | 0.25 |
| 421ES 21 b | 0.36 | |
| 421ES 21 c | 0.19 | |
| 421ES 23 a | 0.01 | 0.01 |
| 421ES 23 b | 0.01 | |
| 421ES 23 c | 0.02 | |
| 421ES 26 a | 0.18 | 0.16 |
| 421ES 26 b | 0.19 | |
| 421ES 26 c | 0.10 | |
| 421ES 27 a | 0.11 | 0.13 |
| 421ES 27 b | 0.16 | |
| 421ES 27 c | 0.12 | |
| 421ES 28 a | 0.02 | 0.01 |
| 421ES 28 b | n.d. | |
| 421ES 28 c | 0.01 | |
| 421ES 29 a | 0.35 | 0.40 |
| 421ES 29 b | 0.46 | |
| 421ES 29 c | 0.39 | |
| 421ES 31 a | 0.14 | 0.14 |
| 421ES 31 b | 0.16 | |
| 421ES 31 c | 0.11 | |
| 421ES 32 a | 0.04 | 0.03 |
| 421ES 32 b | 0.01 | |
| 421ES 32 c | 0.05 | |
| 421ES 33 a | 0.12 | 0.11 |
| 421ES 33 b | 0.08 | |
| 421ES 33 c | 0.13 | |
| 421ES 34 a | 0.32 | 0.34 |
| 421ES 34 b | 0.37 | |
| 421ES 34 c | 0.34 | |
| 421ES 35 a | 0.20 | 0.21 |
| 421ES 35 b | 0.24 | |
| 421ES 35 c | 0.17 | |
| 421ES 36 a | 0.07 | 0.06 |
| 421ES 36 b | 0.07 | |
| 421ES 36 c | 0.03 | |
| 421ES 37 a | 0.12 | 0.12 |
| 421ES 37 b | 0.11 | |
| 421ES 37 c | 0.14 | |
| 421ES 38 a | 0.32 | 0.34 |
| 421ES 38 b | 0.34 | |
| 421ES 38 c | 0.37 | |
| wt 8 a | n.d. | n.d. |
| wt 8 c | n.d. | |
| wt 13 a | n.d. | n.d. |
| wt 13 b | n.d. | |
| wt 13 c | n.d. | |

Column 1 refers to the plant, independently originating from the transformation, from which the material was harvested (here, "wt" refers to non-transformed plants). The extension of the names of the plants by a, b or c denotes independent measurements carried out for the worked-up sample in question.
Non-detectable amounts are marked "n.d.".

These results show that plants having a foreign nucleic acid molecule coding for a protein having the activity of a GFAT-2 and coding for a protein having the activity of a UDP-glucose dehydrogenase have a content of N-acetylated glucosamine derivatives which is considerably higher than that of correspondingly non-transformed wild-type plants.

e) Production of Tomato Plants Comprising a Foreign Nucleic Acid Molecule Coding for a Protein Having the Activity of a Bacterial GFAT Tomato plants (cultivar Moneymaker) were transformed by the method given under General Methods Item 2 with the plant expression vector IC 375-271 comprising a coding nucleic acid sequence for a protein having the activity of a UDP-glucose dehydrogenase and a foreign nucleic acid molecule coding for a protein having the activity of a bacterial GFAT. The transgenic lines obtained, which are transformed with the plasmid IC 375-271, were named 422 ES.

f) Analysis of Lines 422 ES

Plants of the line 422 ES were cultivated in hydroculture in pots in a greenhouse. In each case about 5 g of plant material, harvested from individual plants, were worked up using the method described under General Methods Item 4, and the content of N-acetylated glucosamine derivatives was determined. Here, per plant, a plurality of independent measurements were carried out for each worked-up sample. The following results were obtained for individual plants:

TABLE 6

Amount of N-acetylated glucosamine derivatives (in μmol per gram of fresh weight) measured in leaves of independent transgenic plants of the line 422 ES.

| Plant | μmol/g FW | Mean [μmol/g FW] |
|---|---|---|
| 422ES 2 a | 13.96 | 14.50 |
| 422ES 2 b | 13.39 | |
| 422ES 2 c | 16.13 | |
| 422ES 3 a | 0.28 | 0.29 |
| 422ES 3 b | 0.29 | |
| 422ES 3 c | 0.30 | |
| 422ES 4 a | 0.20 | 0.18 |
| 422ES 4 b | 0.13 | |
| 422ES 4 c | 0.21 | |
| 422ES 5 a | 10.57 | 9.97 |
| 422ES 5 b | 9.74 | |
| 422ES 5 c | 9.60 | |
| 422ES 6 a | 16.58 | 16.20 |
| 422ES 6 b | 16.11 | |
| 422ES 6 c | 15.91 | |
| 422ES 7 a | 3.13 | 2.99 |
| 422ES 7 b | 2.64 | |
| 422ES 7 c | 3.19 | |
| 422ES 8 a | 16.50 | 14.70 |
| 422ES 8 b | 14.32 | |

TABLE 6-continued

Amount of N-acetylated glucosamine derivatives (in μmol per gram of fresh weight) measured in leaves of independent transgenic plants of the line 422 ES.

| Plant | μmol/g FW | Mean [μmol/g FW] |
|---|---|---|
| 422ES 8 c | 13.27 | |
| 422ES 9 a | 9.76 | 9.72 |
| 422ES 9 b | 9.33 | |
| 422ES 9 c | 10.07 | |
| 422ES 11 a | 5.80 | 5.40 |
| 422ES 11 b | 5.34 | |
| 422ES 11 c | 5.05 | |
| 422ES 12 a | 11.57 | 12.23 |
| 422ES 12 b | 11.65 | |
| 422ES 12 c | 13.46 | |
| 422ES 13 a | 13.11 | 10.89 |
| 422ES 13 b | 10.54 | |
| 422ES 13 c | 9.02 | |
| 422ES 14 a | 7.68 | 7.75 |
| 422ES 14 b | 8.05 | |
| 422ES 14 c | 7.52 | |
| 422ES 16 a | 14.02 | 14.45 |
| 422ES 16 b | 13.35 | |
| 422ES 16 c | 15.98 | |
| 422ES 17 a | 10.79 | 9.72 |
| 422ES 17 b | 9.99 | |
| 422ES 17 c | 8.37 | |
| 422ES 18 a | 3.09 | 4.20 |
| 422ES 18 b | 4.55 | |
| 422ES 18 c | 4.96 | |
| 422ES 19 a | 6.43 | 5.99 |
| 422ES 19 b | 4.94 | |
| 422ES 19 c | 6.59 | |
| 422ES 20 a | 15.85 | 15.50 |
| 422ES 20 b | 15.87 | |
| 422ES 20 c | 14.79 | |
| 422ES 21 a | 0.32 | 0.35 |
| 422ES 21 c | 0.38 | |
| wt 9 a | 0.36 | 0.23 |
| wt 9 b | 0.19 | |
| wt 9 c | 0.13 | |
| wt 14 a | n.d. | n.d. |
| wt 14 b | n.d. | |
| wt 14 c | n.d. | |

Column 1 refers to the plant, independently originating from the transformation, from which the material was harvested (here, "wt" refers to non-transformed plants). The extension of the names of the plants by a, b or c denotes independent measurements carried out for the worked-up sample in question.
Non-detectable amounts are marked "n.d.".

g) Analysis of Fruits of Lines 420 ES, 421 ES and 422 ES

Ripe fruits were harvested from selected plants of lines 420 ES, 421 ES and 422 ES. Various whole tomato fruits of individual plants were harvested and worked up using the method described under General Methods Item 4, and the content of N-acetylated glucosamine derivatives was determined. Here, independent measurements were carried out for different fruits of a plant. The following results were obtained for individual plants:

TABLE 7

Amount of N-acetylated glucosamine derivatives (in μmol per gram of fresh weight) measured in fruits of independent transgenic plants of lines 420 ES, 421 ES and 422 ES.

| Plant | μmol/g FW | Mean [μmol/g FW] |
|---|---|---|
| 420ES 2 I | 0.01 | 0.01 |
| 420ES 2 II | 0.01 | |
| 420ES 3 I | 0.07 | 0.06 |
| 420ES 3 II | 0.06 | |
| 420ES 4 I | 0.04 | 0.04 |
| 420ES 4 II | n.d | |
| 420ES 4 III | 0.04 | |
| 420ES 6 I | 0.09 | 0.05 |
| 420ES 6 II | 0.03 | |
| 420ES 6 III | 0.04 | |
| 420ES 7 I | 0.01 | 0.03 |
| 420ES 7 II | 0.04 | |
| 420ES 7 III | 0.05 | |
| 420ES 7 IV | 0.03 | |
| 420ES 8 I | 0.03 | 0.04 |
| 420ES 8 II | 0.04 | |
| 420ES 8 III | 0.04 | |
| 420ES 12 I | 0.00 | 0.04 |
| 420ES 12 II | 0.07 | |
| 420ES 17 I | 0.05 | 0.05 |
| 420ES 17 II | 0.06 | |
| 420ES wt 7 I | n.d | 0.03 |
| 420ES wt 7 II | 0.04 | |
| 420ES wt 7 III | 0.03 | |
| 421ES 4 I | 0.94 | 0.86 |
| 421ES 4 II | 0.85 | |
| 421ES 4 III | 0.67 | |
| 421ES 4 IV | 0.79 | |
| 421ES 4 V | 1.02 | |
| 421ES 5 I | 0.35 | 0.53 |
| 421ES 5 II | 0.72 | |
| 421ES 5 III | 0.67 | |
| 421ES 5 IV | 0.45 | |
| 421ES 5 V | 0.48 | |
| 421ES 21 I | 2.02 | 1.17 |
| 421ES 21 II | 0.92 | |
| 421ES 21 III | 0.96 | |
| 421ES 21 IV | 0.79 | |
| 421ES 25 I | 0.61 | 0.76 |
| 421ES 25 II | 0.75 | |
| 421ES 25 III | 0.91 | |
| 421ES 27 I | 0.86 | 0.89 |
| 421ES 27 II | 0.91 | |
| 421ES 27 III | 0.90 | |
| 421ES 29 I | 0.48 | 0.76 |
| 421ES 29 II | 0.52 | |
| 421ES 29 III | 0.52 | |
| 421ES 29 IV | 1.53 | |
| 421ES 33 I | 0.74 | 0.67 |
| 421ES 33 II | 0.83 | |
| 421ES 33 III | 0.45 | |
| 421ES 35 I | 0.48 | 0.77 |
| 421ES 35 II | 0.79 | |
| 421ES 35 III | 0.87 | |
| 421ES 35 IV | 0.95 | |
| 421ES 38 I | 0.97 | 1.21 |
| 421ES 38 II | 1.35 | |
| 421ES 38 III | 1.29 | |
| 421ES wt 13 I | 0.03 | 0.04 |
| 421ES wt 13 II | 0.05 | |
| 421ES wt 13 III | n.d | |
| 422ES 2 I | 3.17 | 4.26 |
| 422ES 2 II | 3.74 | |
| 422ES 2 III | 5.79 | |
| 422ES 2 IV | 4.90 | |
| 422ES 2 V | 3.73 | |
| 422ES 5 I | 2.12 | 3.41 |
| 422ES 5 II | 1.76 | |
| 422ES 5 III | 1.99 | |
| 422ES 5 IV | 3.26 | |
| 422ES 5 V | 5.27 | |
| 422ES 5 VI | 4.49 | |
| 422ES 5 VII | 4.95 | |
| 422ES 6 I | 7.41 | 7.41 |
| 422ES 9 I | 3.67 | 3.34 |
| 422ES 9 II | 3.02 | |
| 422ES 11 I | 2.55 | 1.98 |
| 422ES 11 II | 1.92 | |
| 422ES 11 III | 1.47 | |
| 422ES 12 I | 3.76 | 7.65 |

TABLE 7-continued

Amount of N-acetylated glucosamine derivatives (in μmol per gram of fresh weight) measured in fruits of independent transgenic plants of lines 420 ES, 421 ES and 422 ES.

| Plant | μmol/g FW | Mean [μmol/g FW] |
|---|---|---|
| 422ES 12 II | 9.80 | |
| 422ES 12 III | 9.39 | |
| 422ES 13 I | 5.79 | 5.31 |
| 422ES 13 II | 5.04 | |
| 422ES 13 III | 5.11 | |
| 422ES 14 I | 4.08 | 3.50 |
| 422ES 14 II | 2.93 | |
| 422ES 16 I | 2.62 | 3.60 |
| 422ES 16 II | 2.72 | |
| 422ES 16 III | 5.45 | |
| 422ES 17 I | 7.25 | 7.57 |
| 422ES 17 II | 7.89 | |
| 422ES 18 I | n.d. | 2.30 |
| 422ES 18 II | 2.56 | |
| 422ES 18 III | 2.04 | |
| 422ES wt 9 I | 0.02 | 0.02 |
| 422ES wt 9 II | 0.01 | |
| 422ES wt 9 III | 0.00 | |
| 422ES wt 9 IV | 0.05 | |
| 422ES wt 9 V | n.d. | |
| 422ES wt 14 I | 0.05 | 0.05 |
| 422ES wt 14 II | n.d. | |
| 422ES wt 14 III | n.d. | |

Column 1 refers to the plant, independently originating from the transformation, from which material was harvested (here, "wt" refers to non-transformed plants). The extension of the names of the plants by Latin numerals denotes different fruits of the plant in question. Non-detectable amounts are marked "n.d.".

These results show that plants having a foreign nucleic acid molecule coding for a protein having the activity of a bacterial GFAT and coding for a protein having the activity of a UDP-glucose dehydrogenase have a considerably higher content of N-acetylated glucosamine derivatives than correspondingly non-transformed wild-type plants. Compared to plants having a foreign nucleic acid molecule coding for a protein having the activity of a GFAT-1 and coding for a protein having the activity of a UDP-glucose dehydrogenase, plants comprising a foreign nucleic acid molecule coding for a protein having the activity of a GFAT-2 and coding for a protein having the activity of a UDP-glucose dehydrogenase have an even higher content of N-acetylated glucosamine derivatives. This is true both for leaf material and for fruits of the plants in question.

h) Analysis of N-Acetylated Glucosamine Derivatives of Line 422 ES by Mass Spectroscopy Extracts of individual different fruits of the plant with the name 422 ES 13 were examined by mass spectroscopy according to the method described under General Methods Item 9 for the presence of N-acetylated glucosamine derivatives. The following results were obtained:

TABLE 8

Detection of the metabolites glucosamine (GlcN), N-acetylglucosamine (GlcNAc), glucosamine phosphate (GlcN-P), N-acetylglucosamine phosphate (GlcNAc-P) and UDP-N-acetylglucosamine (UDP-GlcNAc) in fruits of the plant 422 ES 13 by mass spectroscopy. What is shown is the proportion of the signal intensity (peak area) obtained for the stated metabolite in the mass spectrum, based on the signal intensity for hexoses (m/z = 179) obtained in the same measurement, in percent. The different measurements were carried out at the stated detector settings with respect to sensitivity ("d.v.") and signal intensity ("cps") (column 1). Column 2 denotes the plant, independently originating from the transformation, from which material was harvested (here, "wt" refers to non-transformed plants). The extension of the names of the plants by Latin numerals denote different fruits of the plant in question.

| | | Mass (m/z) with associated metabolites | | | | |
|---|---|---|---|---|---|---|
| Detector | Sample | 178 GlcN | 220 GlcNAc | 258 GlcN-P | 300 GlcNAc-P | 302.5 UDP-GlcNAc |
| cps: 9.5-10 e4 | 422 ES 13 I | 0.08 | 5.08 | 0.56 | 1.44 | 0.14 |
| (d.v.: 2000) | 422 ES 13 II | 0.09 | 6.41 | 0.61 | 1.48 | 0.14 |
| | 422 ES 13 III | 0.09 | 5.95 | 1.05 | 1.51 | 0.18 |
| | wt | 0.06 | 0.05 | 0.10 | 0.06 | 0.00 |
| cps: 1.6-1.8 e5 | 422 ES 13 I | 0.37 | 10.69 | 1.91 | 4.31 | 0.42 |
| (d.v.: 2050) | 422 ES 13 II | 0.37 | 13.92 | 2.10 | 4.49 | 0.45 |
| | 422 ES 13 III | 0.30 | 12.96 | 3.43 | 3.98 | 0.55 |
| | wt | 0.30 | 0.25 | 0.49 | 0.38 | 0.03 |
| cps: 2.0-2.2 e5 | 422 ES 13 I | 0.71 | 18.77 | 3.95 | 8.70 | 0.73 |
| (d.v.: 2100) | 422 ES 13 II | 0.68 | 21.81 | 3.88 | 8.32 | 0.67 |
| | 422 ES 13 III | 0.48 | 19.82 | 6.25 | 7.14 | 0.84 |
| | wt | 0.55 | 0.53 | 1.05 | 0.94 | 0.05 |

In parallel, via MS-MS measurements of samples 422 ES 13 I and fruits of a wild-type plant (wt) using reference substances (glucosamine, N-acetylgucosamine, glucosamine 6-phosphate, glucosamine 1-phosphate, N-acetylgucosamine 6-phosphate, N-acetylglucosamine 1-phosphate, UDP-N-acetylglucosamine) it was analyzed whether the detected signal intensities (peak areas) in question of the MS spectra were really due to the presence of the corresponding metabolite or the corresponding isomeric metabolites of the same mass, or whether the signal intensities in question in the MS spectrum were possibly caused by interference by signals of other substances. The following observations were made:

Glucosamine (GlcN, m/z=178): The highest amounts of GlcN detected in the MS spectra of samples 422 ES 13 I and wt were in the range of the lower detection limit. In the MS spectrum, no significant differences between the sample 422 ES 13 I and the wt samples were noticed. Accordingly, it was not possible to determine with any degree of certainty whether the samples contained GlcN.

N-Acetylglucosamine (GlcNAc, m/z=220): The most significant differences in the MS spectra of samples 422 ES 13 and the wt sample were found for this metabolite. In the MS spectra of samples 422 ES 13 I, 422 ES 13 II and 422 ES 13 III, considerable amounts of GlcNAc were detected. The corresponding MS-MS spectrum for the sample 422 ES 13 I corresponds to the spectrum of the reference substance (N-acetylglucosamine) and has, if any, only very small amounts of substances which may interfere with the relevant signal in the MS spectrum. In contrast, in the MS spectrum of the wt sample the signal intensity for m/z=220 was very low. The MS-MS spectrum of the wt sample showed that GlcNAc is only present in traces, if at all. The MS-MS spectrum very clearly showed that the signal intensity determined for m/z=220 of the wt sample in the MS spectrum was the result mainly of other substances interfering with the signal.

Glucosamine phosphates (GlcN-P, m/z=258): The signal intensity of the MS spectra for the wt sample is considerably lower than for samples 422 ES 13 I, 422 ES 13 II and 422 ES 13 III. All samples measured by MS-MS show that the signal for m/z=258 is not only due to the presence of GlcN-P but also to interference of the signal by other substances. The MS-MS spectrum of the wt sample showed that only traces of GlcN-P are present, if any. In contrast, the corresponding signal for sample 422 ES 13 I in the MS-MS spectrum showed the presence of significant amounts of GlcN-P in the relevant signal of the MS spectrum.

N-Acetylglucosamine phosphate (GlcNAc-P, m/z=300): For the wt sample, the signal intensities for m/z=300 in the MS spectrum are substantially lower than for the samples 422 ES 13 I, 422 ES 13 II and 422 ES 13 III. The values determined by MS-MS for the wt sample show that, if any, only traces of GlcNAc-P are present. In contrast, for sample 422 ES 13 I it was possible to demonstrate by MS-MS measurement that the predominant part of the signal intensity determined for m/z=300 in the MS spectrum of this sample is due to GlcNAc-P.

UDP-N-Acetylglucosamine (UDP-GlcNAc, m/z=302.5): In the wild-type, the signal intensities of the MS spectrum are considerably lower than in samples 422 ES 13 I, 422 ES II and 422 ES III. The corresponding MS-MS spectra show that in all samples a certain part of the signal intensity of the MS spectra is not only due to the presence of UDP-GlcNAc, but also due to signal interference by other substances. However, the MS-MS measurements showed that compared to the signal-interfering substances, the proportion of UDP-GlcNAc in the MS spectra of sample 422 ES 13 I is substantially higher than for the wt sample.

19. Production of Plants which Synthesize Glucosaminoglycans

To determine whether plants having an increased content of N-acetylated glucosamine derivatives are suitable for producing plants having an increased glucosaminoglycan content, at first plants expressing a glucosaminoglycan synthase (hyaluronan synthase) were generated.

a) Plants Comprising a Nucleic Acid Molecule Coding for a Protein Having the Activity of a Hyaluronan Synthase Potato plants (cultivar Désirée) and tomato plants (cultivar Moneymaker) were transformed using the method given under General Methods Item 1 (potato plants) and under General Methods Item 2 (tomato plants) respectively, with the plant expression vector IC 341-222 which comprises a coding nucleic acid sequence for a protein having the activity of a hyaluronan synthase from *Paramecium bursaria Chlorella* Virus 1 under the control of the promoter of the patatin gene B33 from *Solanum tuberosum* (Rocha-Sosa et al., 1989, EMBO J. 8, 23-29). The transgenic lines obtained, which are transformed with the plasmid IC 341-222, were named 365 ES (potato plants) and 367 ES (tomato plants), respectively.

b) Analysis of the Lines 365 ES

Individual plants of the line 365 ES were cultivated in soil in 6 cm pots in a greenhouse. In each case about 0.3 g of material of potato tubers of the individual plants was worked up using the method described under General Methods Item 5. The amount of the hyaluronan present in the respective plant extracts was determined using the method described under General Methods Item 7. Here, the supernatant obtained after centrifugation was diluted 1:10 to determine the hyaluronan content. The following results were obtained for selected plants:

TABLE 9

Amount of hyaluronan (in μg per gram of fresh weight) produced by independent selected transgenic plants of line 365 ES.

| Plant | Hyaluronan [μg/g FW] |
|---|---|
| 365 ES 13 | 47 |
| 365 ES 74 | 68 |
| wt | n.d. |

Column 1 refers to the plant from which tuber material was harvested (here, "wt" refers to non-transformed plants). Column 2 states the value for the amount of hyaluronan determined in leaves of the plant in question. Non-detectable amounts are marked "n.d.".

c) Analysis of Plants of Line 367 ES

From different selected tomato plants of line 367 ES which had been cultivated in soil in a greenhouse, in each case 1 leaf was harvested and frozen in liquid nitrogen. Further work-up and determination of the hyaluronan content was carried out as described in Example 19b) for tubers of potato plants. The following results were obtained:

TABLE 10

Amount of hyaluronan (in μg per gram of fresh weight) produced in leaves of independent selected transgenic plants of lines 367 ES.

| Plant | Hyaluronan [μg/g FW] |
|---|---|
| 367 ES 25 | 57.19 |
| 367 ES 42 | 88.99 |
| wt | 0.06 |

Column 1 refers to the plant from which leaf material was harvested (here, "wt" refers to non-transformed plants). Column 2 states the value of the amount of hyaluronan determined in leaves of the plants in question.

20. Plants Comprising a Foreign Nucleic Acid Molecule Coding for a Protein Having The Activity of a UDP-Glucose Dehydrogenase and a Nucleic Acid Molecule Coding for a Protein Having the Activity of a Glucosaminoglycan Synthase Some glucosaminoglycan synthases (such as, for example, hyaluronan synthase) require, as substrate, N-acetylated glucosamine derivatives and UDP-GlcA. Accordingly, we first generated plants having an increased activity of a protein having the activity of a UDP-glucose dehydrogenase and an increased activity of a protein having the activity of a hyaluronan synthase.

a) Production of Potato Plants

Potato plants of line 365 ES 74 (see Example 19b)) were transformed using the method given under General Methods Item 1 with the plant expression vector IC 349-222 comprising a coding nucleic acid sequence for a protein having the activity of a UDP-glucose dehydrogenase under the control of the 35S promoter. The transgenic lines obtained, which are transformed with the plasmid IC 349-222, were named 423 ES.

b) Analysis of Plants of Line 423 ES

Plants of line 423 ES were cultivated in soil in 6 cm pots in a greenhouse. In each case about 0.3 g to 0.8 g of leaf material, harvested from individual plants, was worked up using the method described under General Methods Item 5, and the content of Hyaluronan was determined using the method described under General Methods Item 7. For individual plants having an increased content of N-acetylglucosamine derivatives, the following results were obtained:

TABLE 11

Amount of hyaluronan (in µg per gram of fresh weight) measured in leaves of independent transgenic plants of line 423 ES.

| Plant | Hyaluronan [µg/g FW] |
| --- | --- |
| 423ES 1 | 328.75 |
| 423ES 3 | 210.38 |
| 423ES 5 | 340.99 |
| 423ES 6 | 250.88 |
| 423ES 7 | 214.53 |
| 423ES 8 | 309.22 |
| 423ES 9 | 253.31 |
| 423ES 10 | 229.61 |
| 423ES 11 | 234.40 |
| 423ES 12 | 480.22 |
| 423ES 13 | 253.63 |
| 423ES 14 | 221.77 |
| 423ES 15 | 202.46 |
| 423ES 17 | 281.46 |
| 423ES 18 | 310.41 |
| 423ES 19 | 268.91 |
| 423ES 20 | 394.04 |
| 423ES 21 | 462.64 |
| 423ES 24 | 438.33 |
| 423ES 25 | 419.50 |
| 423ES 26 | 342.89 |
| 423ES 27 | 383.32 |
| 423ES 28 | 236.83 |
| 423ES 29 | 332.63 |
| 423ES 32 | 254.88 |
| 423ES 33 | 283.31 |
| 423ES 35 | 276.60 |
| 423ES 36 | 308.85 |
| 423ES 38 | 307.72 |
| 423ES 41 | 259.89 |
| 423ES 43 | 244.62 |
| 423ES 47 | 229.25 |
| 423ES 48 | 238.22 |
| 423ES 49 | 285.19 |
| 423ES 51 | 213.97 |

TABLE 11-continued

Amount of hyaluronan (in µg per gram of fresh weight) measured in leaves of independent transgenic plants of line 423 ES.

| Plant | Hyaluronan [µg/g FW] |
| --- | --- |
| 423ES 53 | 328.76 |
| 423ES 54 | 358.23 |
| 423ES 55 | 154.06 |
| 423ES 59 | 276.32 |
| 423ES 60 | 498.70 |
| 423ES 61 | 300.97 |
| 423ES 62 | 292.08 |
| 423ES 65 | 230.38 |
| 423ES 67 | 267.54 |
| 423ES 68 | 370.08 |
| wt 1 | 0.38 |
| wt 2 | 0.12 |
| wt 3 | 0.07 |
| wt 4 | n.d. |
| wt 5 | 0.47 |
| wt 6 | n.d. |
| wt 7 | 0.05 |
| wt 8 | 0.05 |
| wt 9 | 0.10 |
| wt 10 | n.d. |
| 365ES 74-1 | 348.43 |
| 365ES 74-2 | 214.59 |
| 365ES 74-3 | 391.88 |
| 365ES 74-4 | 442.60 |
| 365ES 74-5 | 293.01 |
| 365ES 74-6 | 323.47 |
| 365ES 74-7 | 464.21 |
| 365ES 74-8 | 341.32 |
| 365ES 74-9 | 338.93 |
| 365ES 74-10 | 438.55 |

Column 1 refers in each case to the plants, independently originating from the transformation, from which material was harvested (here, "wt 1" to "wt 10" refer to independent non-transformed plants). For comparison, values for 10 different progeny of plants of line 365 ES used as starting line for the transformation (365 ES-1 to 365 ES-10) are shown. Non-detectable amounts are marked "n.d.".

It can be seen from the results that plants comprising a foreign nucleic acid molecule coding for a protein having the activity of a UDP-glucose-dehydrogenase and a nucleic acid molecule coding for a protein having the activity of a hyaluronan synthase do not synthesize any statically significant increased amounts of hyaluronan compared to plants having only a nucleic acid molecule coding for a protein having the activity of a hyaluronan synthase.

21. Plants Synthesizing Increased Amounts of Glucosaminoglycan a) Production of Tomato Plants Synthesizing Increased Amounts of Glucosaminoglycan Tomato plants of lines 367 ES 25 (see example 19c)), having a nucleic acid molecule coding for a hyaluronan synthase were transformed again using the method given under General Methods Item 2 with the plant expression vectors IC 372-256 or IC 375-271 comprising nucleic acid molecules coding for different isoforms of proteins having the activity of a GFAT.

The transgenic tomato plants obtained after transformation of line 367 ES 25, with the plasmid IC 372-256 (GFAT-2), were named 399 ES.

The transgenic tomato plants obtained after transformation of line 367 ES 25 with the plasmid IC 375-271 (bacterial GFAT), were named 405 ES.

b) Analysis of Lines 399 ES and 405 ES

Ripe fruits were harvested from different tomato plants of lines 399 ES and 405 ES cultivated in soil in a greenhouse, and the hyaluronan content was determined as described under General Methods Item 7. The following results were obtained:

TABLE 12

Amount of hyaluronan ("HA" in μg per gram of fresh weight) measured in fruits of independent transgenic plants of lines 399 ES and 405 ES.

| Sample | HA [μg/g FW] | Mean [μg/g FW] |
|---|---|---|
| 399ES 1 I | 63.38 | 87.02 |
| 399ES 1 II | 96.45 | |
| 399ES 1 III | 101.23 | |
| 399ES 11 I | 388.83 | 292.79 |
| 399ES 11 II | 244.01 | |
| 399ES 11 III | 254.91 | |
| 399ES 11 IV | 285.72 | |
| 399ES 11 V | 297.99 | |
| 399ES 11 VI | 285.29 | |
| wt I | 0.02 | 0.01 |
| wt II | 0.02 | |
| wt III | 0.01 | |
| wt IV | n.d. | |
| 367ES 25-1 I | 9.77 | 12.04 |
| 367ES 25-1 II | 8.21 | |
| 367ES 25-1 III | 18.04 | |
| 367ES 25-1 IV | 13.86 | |
| 367ES 25-1 V | 10.33 | |
| 367ES 25-2 I | 9.31 | 11.96 |
| 367ES 25-2 II | 10.55 | |
| 367ES 25-2 III | 11.53 | |
| 367ES 25-2 IV | 16.54 | |
| 367ES 25-2 V | 11.86 | |
| 367ES 25-3 I | 6.99 | 8.51 |
| 367ES 25-3 II | 7.94 | |
| 367ES 25-3 III | 9.23 | |
| 367ES 25-3 IV | 7.09 | |
| 367ES 25-3 V | 11.28 | |
| 405ES 5 I | 207.20 | 254.94 |
| 405ES 5 II | 302.67 | |
| 405ES 10 I | 1232.38 | 1074.94 |
| 405ES 10 II | 917.50 | |
| wt I | 0.86 | 0.46 |
| wt II | 0.06 | |
| 367ES 25-8 I | 136.67 | 155.70 |
| 367ES 25-8 II | 174.72 | |
| 367ES 25-9 I | 37.76 | |

Column 1 refers to the plants, independently originating from the transformation, from which material was harvested (here, "wt" refers to non-transformed plants). For comparison, values of different progeny of plants of line 367 ES used as starting line for the transformation are shown. The extensions of the names of the plants by Latin numerals denote different fruits of the plant in question.
Non-detectable amounts are marked "n.d.".

These results show that plants comprising foreign nucleic acid molecules coding for a glucosaminoglycan synthase and coding for a protein having the activity of a UDP-glucose dehydrogenase and coding for a protein having the activity of a GFAT-2 or a bacterial GFAT synthesize considerably higher amounts of glucosaminoglycans than plants having only a foreign nucleic acid molecule coding for a glucosaminoglycan synthase.

c) Production of Potato Plants Synthesizing Increased Amounts of Glucosaminoglycan Potato plants of lines 365 ES 74 (see example 19b)) comprising a nucleic acid molecule coding for a hyaluronan synthase were transformed again using the method stated under General Methods Item 1 with the plant expression vectors IC 376-271, IC 372-256 or IC 375-271 comprising nucleic acid molecules coding for different isoforms of proteins having the activity of a GFAT.

The transgenic potato plants obtained after transformation of line 365 ES 74 with the plasmid IC 376-271 (GFAT-1), were named 409 ES.

The transgenic potato plants obtained after transformation of line 365 ES 74 with the plasmid IC 372-256 (GFAT-2), were named 396 ES.

The transgenic potato plants obtained after transformation of line 365 ES 74 with the plasmid IC 375-271 (bacterial GFAT), were named 404 ES.

d) Analysis of Lines 396 ES, 404 ES and 409 ES

Leaf and/or tuber material was harvested from different potato plants of lines 396 ES (GFAT-2), 404 ES (bacterial GFAT) and 409 ES (GFAT-1) cultivated in soil in a greenhouse, and the hyaluronan content was determined as described under General Methods Item 7. The following results were obtained for plants of line 409 ES:

TABLE 13

Amount of hyaluronan ("HA" in μg per gram of fresh weight) measured in leaves and tubers of independent transgenic plants of line 409 ES.

| Plant | HA in leaves [μg/g FW] | HA in tubers [μg/g FW] |
|---|---|---|
| 409 ES 2 | 54.01 | |
| 409 ES 3 | 68.75 | 212.24 |
| 409 ES 4 | 59.80 | 111.54 |
| 409 ES 5 | 26.90 | |
| 409 ES 6 | 38.01 | 182.39 |
| 409 ES 7 | 25.80 | 95.68 |
| 409 ES 8 | 51.92 | 99.35 |
| 409 ES 9 | 48.43 | 168.61 |
| 409 ES 10 | 52.52 | |
| 409 ES 13 | 55.87 | |
| 409 ES 14 | 45.91 | 143.96 |
| 409 ES 15 | 52.76 | |
| 409 ES 16 | 60.28 | |
| 409 ES 22 | 69.47 | 114.97 |
| 409 ES 23 | 108.67 | |
| 409 ES 26 | 38.81 | |
| 409 ES 27 | 24.71 | 126.74 |
| 409 ES 28 | 66.95 | |
| 409 ES 29 | 79.58 | 164.66 |
| wt-1 | n.d. | |
| wt-2 | n.d. | |
| wt-3 | n.d. | |
| wt-4 | n.d. | |
| 365 ES 74-1 | 25.19 | |
| 365 ES 74-2 | 31.15 | |
| 365 ES 74-3 | 72.96 | |
| 365 ES 74-4 | 35.98 | |
| 365 ES 74-5 | 40.18 | 123.66 |
| 365 ES 74-6 | 37.70 | |

Column 1 refers to the plants, independently originating from the transformation, from which material was harvested (here, "wt" refers to non-transformed plants). Values for different progeny of plants of line 365 ES 74, which was used as starting line for the transformation, are shown for comparison.
Non-detectable amounts are marked "n.d.".

The following results were obtained for plants of line 396 ES:

TABLE 14

Amount of hyaluronan ("HA" in μg per gram of fresh weight) measured in leaves and tubers of independent transgenic plants of line 396 ES.

| Plant | HA in leaves [μg/g FW] | HA in tubers [μg/g FW] |
|---|---|---|
| 396 ES 2 | | 470.93 |
| 396 ES 9 | | 735.40 |
| 396 ES 11 | 938.33 | |
| 396 ES 15 | | 393.64 |
| 396 ES 16 | 416.43 | |
| 396 ES 17 | 426.79 | |
| 396 ES 23 | 271.85 | |
| 396 ES 24 | 443.57 | |
| 396 ES 25 | 801.58 | |
| 396 ES 28 | | 484.76 |
| 396 ES 30 | | 224.06 |
| 396 ES 32 | 941.89 | |
| 396 ES 33 | | 1295.98 |

TABLE 14-continued

Amount of hyaluronan ("HA" in μg per gram of fresh weight) measured in leaves and tubers of independent transgenic plants of line 396 ES.

| Plant | HA in leaves [μg/g FW] | HA in tubers [μg/g FW] |
|---|---|---|
| 396 ES 34 | 796.79 | |
| 396 ES 36 | 204.49 | |
| 396 ES 36 | 860.54 | |
| 396 ES 42 | | 1445.51 |
| 396 ES 44 | | 1312.56 |
| 396 ES 48 | 461.05 | |
| 396 ES 49 | 538.75 | |
| 396 ES 50 | 619.23 | |
| 396 ES 51 | 1160.57 | |
| 396 ES 57 | 428.33 | |
| 396 ES 57 | 807.97 | |
| 365 ES 74-1 | 265.10 | |
| 366 ES 74-2 | | 91.84 |
| 365 ES 74-3 | 193.50 | |
| 367 ES 74-4 | | 175.48 |
| 365 ES 74-5 | 73.90 | |
| 368 ES 74-6 | | 168.68 |
| 365 ES 74-7 | 67.58 | |
| 369 ES 74-8 | | 121.89 |
| 365 ES 74-9 | 62.23 | |
| 370 ES 74-10 | | 275.24 |
| 365 ES 74-11 | 134.56 | |
| wt-1 | 0.07 | 2.27 |
| wt-2 | 0.11 | |
| wt-3 | 0.12 | 1.07 |
| wt-4 | 0.04 | 0.78 |
| wt-5 | 0.10 | |
| wt-5 | 0.24 | |

Column 1 refers to the plants, independently originating from the transformation, from which material was harvested (here, "wt" refers to non-transformed plants). Values for different progeny of plants of line 365 ES 74, which was used as starting line for the transformation, are shown for comparison.

The following results were obtained for plants of 404 ES:

TABLE 15

Amount of hyaluronan (in μg per gram of fresh weight) measured in leaves of independent transgenic plants of line 404 ES.

| Plant | Hyaluronan in leaves [μg/g FW] |
|---|---|
| 404 ES 1 | 801.14 |
| 404 ES 6 | 365.15 |
| 404 ES 7 | 218.42 |
| 404 ES 8 | 521.92 |
| 404 ES 9 | 366.46 |
| 404 ES 10 | 226.83 |
| 404 ES 11 | 231.39 |
| 404 ES 13 | 1547.12 |
| 404 ES 14 | 616.79 |
| 404 ES 15 | 832.32 |
| 404 ES 20 | 581.11 |
| 404 ES 21 | 489.73 |
| 404 ES 23 | 817.91 |
| 404 ES 24 | 434.06 |
| 404 ES 26 | 205.00 |
| 404 ES 28 | 359.96 |
| 404 ES 29 | 1146.68 |
| 404 ES 34 | 310.76 |
| 404 ES 35 | 1388.51 |
| 404 ES 36 | 1095.11 |
| 404 ES 37 | 533.89 |
| 404 ES 38 | 651.12 |
| 404 ES 39 | 353.74 |
| 404 ES 40 | 371.88 |
| 404 ES 42 | 849.43 |
| 404 ES 43 | 479.34 |
| 404 ES 44 | 921.11 |
| 404 ES 46 | 846.81 |
| 404 ES 48 | 302.54 |

TABLE 15-continued

Amount of hyaluronan (in μg per gram of fresh weight) measured in leaves of independent transgenic plants of line 404 ES.

| Plant | Hyaluronan in leaves [μg/g FW] |
|---|---|
| wt-1 | 0.20 |
| wt-2 | 0.30 |
| wt-3 | 0.19 |
| wt-4 | 0.39 |
| wt-5 | 0.20 |
| 365 ES 74-1 | 72.44 |
| 365 ES 74-2 | 135.60 |
| 365 ES 74-3 | 19.56 |
| 365 ES 74-4 | 114.83 |
| 365 ES 74-5 | 73.77 |

Column 1 refers to the plants, independently originating from the transformation, from which material was harvested here, ("wt" refers to non-transformed plants). Values for different progeny of plants of line 365 ES 74, which was used as starting line for the transformation, are shown for comparison.

These results show that plants comprising foreign nucleic acid molecules coding for a glucosaminoglycan synthase and coding for a protein having the activity of a UDP-glucose dehydrogenase and coding for a protein having the activity of a GFAT-2 or a bacterial GFAT synthesize considerably higher amounts of glucosaminoglycan than plants comprising foreign nucleic acid molecules coding for a glucosaminoglycan synthase and coding for a protein having the activity of a UDP-glucose dehydrogenase and coding for a protein having the activity of a GFAT-1.

e) Production of Plants Comprising Foreign Nucleic Acid Molecules Coding for a Hyaluronan Synthase and a Protein Having the Activity of a Bacterial GFAT Potato plants of line 365 ES 74 (see example 19b)), comprising a nucleic acid molecule coding for a hyaluronan synthase were transformed again using the method given under General Methods Item 1 with the plant expression vector IC 398-311 comprising nucleic acid molecules coding for a protein having the activity of a bacterial GFAT. The lines originating from this transformation were named 433 ES.

f) Analysis of Line 433 ES

Leaf and/or tuber material was harvested from different potato plants of line 433 ES cultivated in soil in a greenhouse, and the hyaluronan content was determined as described under General Methods Item 7. The following results were obtained for plants of line 433 ES:

TABLE 16

Amount of hyaluronan ("HA" in μg per gram of fresh weight) measured in leaves and tubers of independent transgenic plants of line 433 ES.

| Plant | HA in leaves [μg/g FW] | HA in tubers [μg/g FW] |
|---|---|---|
| 433ES 1 | 111.84 | 126.70 |
| 433ES 3 | 303.34 | 203.16 |
| 433ES 4 | 3142.41 | |
| 433ES 5 | 312.98 | 825.96 |
| 433ES 7 | 1492.94 | |
| 433ES 8 | 914.03 | |
| 433ES 9 | 1858.68 | |
| 433ES 10 | 357.90 | |
| 433ES 11 | 5962.82 | |
| 433ES 12 | | 662.99 |
| 433ES 13 | 626.52 | 624.33 |
| 433ES 14 | 665.23 | |
| 433ES 15 | 601.36 | |
| 433ES 16 | 3416.94 | |
| 433ES 18 | 781.02 | |

TABLE 16-continued

Amount of hyaluronan ("HA" in µg per gram of fresh weight) measured in leaves and tubers of independent transgenic plants of line 433 ES.

| Plant | HA in leaves [µg/g FW] | HA in tubers [µg/g FW] |
|---|---|---|
| 433ES 19 | 3294.09 | |
| 433ES 20 | 1348.85 | 975.18 |
| 433ES 21 | 937.92 | |
| 433ES 22 | 1086.45 | |
| 433ES 23 | 1327.28 | |
| 433ES 24 | 340.80 | 76.00 |
| 433ES 25 | 1529.95 | |
| 433ES 26 | 375.53 | |
| 433ES 27 | | 425.65 |
| 433ES 28 | 1850.99 | 294.98 |
| 433ES 30 | 2512.40 | |
| 433ES 31 | 3337.54 | |
| 433ES 32 | 1583.60 | |
| 433ES 34 | 3552.44 | |
| 433ES 35 | 5419.43 | |
| 433ES 36 | 902.01 | |
| 433ES 37 | 829.35 | |
| 433ES 38 | 1536.55 | |
| wt-1 | 0.40 | n.d. |
| wt-2 | 0.34 | n.d. |
| wt-3 | n.d. | |
| 365 ES 74-1 | 265.1 | |
| 366 ES 74-2 | | 91.84 |
| 365 ES 74-3 | 193.5 | |
| 367 ES 74-4 | | 175.48 |
| 365 ES 74-5 | 73.9 | |
| 368 ES 74-6 | | 168.68 |
| 365 ES 74-7 | 67.58 | |
| 369 ES 74-8 | | 121.89 |
| 365 ES 74-9 | 62.23 | |
| 370 ES 74-10 | | 275.24 |
| 365 ES 74-11 | 134.56 | |

Column 1 refers to the plants, independently originating from the transformation, from which material was harvested (here, "wt" refers to non-transformed plants). Values for different progeny of plants of line 365 ES 74, which was used as starting line for the transformation, are shown for comparison. The values for line 365 ES 74 correspond to those in Table 14, since all plants were cultivated simultaneously in a greenhouse.

These results show that plants comprising foreign nucleic acid molecules coding for a glucosaminoglycan synthase and coding for a protein having the activity of a bacterial GFAT synthesize considerably higher amounts of glucosaminoglycan than plants having only foreign nucleic acid molecules coding for a glucosaminoglycan synthase.

22. Summary of the Results

The results in Example 16 show that plants comprising a nucleic acid molecule coding for a protein having the activity of a bacterial GFAT have considerably increased contents of N-acetylated glucosamine derivatives compared to non-transformed wild-type plants.

The results in Example 17 show that plants comprising a nucleic acid molecule coding for a protein having the activity of a GFAT-2 have considerably higher contents of N-acetylated glucosamine derivatives than non-transformed wild-type plants.

All transformed plants described in Example 18 have, in addition to nucleic acid molecules coding for different isoforms of a protein having the activity of a GFAT, in each case the same nucleic acid molecule coding for a protein having the activity of a UDP-glucose dehydrogenase. Accordingly, the essential difference of the transformed plants described in Example 18 are the different foreign nucleic acid molecules coding for the different isoforms of a protein having the activity of a GFAT. Example 18b) shows that the content of N-acetylated glucosamine derivatives in plants having a foreign nucleic acid molecule coding for a protein having the activity of a GFAT-1 is increased only slightly compared to non-transformed plants.

Furthermore, it can be seen from Example 18d) that plants comprising a foreign nucleic acid molecule coding for a protein having the activity of a GFAT-2 have a considerably higher content of N-acetylated glucosamine derivatives than non-transformed wild-type plants. The content of N-acetylated glucosamine derivatives in plants having a foreign nucleic acid molecule coding for a protein having the activity of a GFAT-2 is also considerably higher than in plants having a foreign nucleic acid molecule coding for a protein having the activity of a GFAT-1.

Furthermore, it can be seen from Examples 18f) and g) that plants comprising a foreign nucleic acid molecule coding for a protein having the activity of a bacterial GFAT have even higher contents of N-acetylated glucosamine derivatives than plants comprising a foreign nucleic acid molecule coding for a protein having the activity of a GFAT-2.

The results in Example 21f) show that plants comprising foreign nucleic acid molecules coding for a glucosaminoglycan synthase and coding for a protein having the activity of a bacterial GFAT synthesize considerably higher amounts of glucosaminoglycan than plants having only foreign nucleic acid molecules coding for a glucosaminoglycan synthase.

Thus, it can be concluded that the amount of glucosaminoglycans synthesized in plants can be increased considerably by generating plants which, in addition to foreign nucleic acid molecules coding for a glucosaminoglycan synthase, additionally comprise foreign nucleic acid molecules coding for a protein having the activity of a bacterial GFAT.

All transformed plants whose results are shown in Examples 21b) and d) have, in addition to nucleic acid molecules coding for different isoforms of a protein having the activity of a GFAT, also foreign nucleic acid molecules coding for a protein having the activity of a UDP-glucose dehydrogenase and foreign nucleic acid molecules coding for a glucosaminoglycan synthase. The essential difference between the transformed plants whose results are shown in Examples 21b) and d) accordingly consists in the different nucleic acid molecules coding for the different isoforms of a protein having the activity of a GFAT.

The results shown in Example 21b) show that the content of glucosaminoglycans in plants having a foreign nucleic acid molecule coding for a protein having the activity of a GFAT-2 or coding for a protein having the activity of a bacterial GFAT is increased considerably compared to plants having only the activity of a glucosaminoglycan synthase.

The results shown in Example 21d) show that plants comprising a foreign nucleic acid molecule coding a protein having the activity of a GFAT-1 contain a slightly higher amount of glucosaminoglycans than plants having only the activity of a glucosaminoglycan synthase. In contrast, the content of glucosaminoglycans in plants comprising a foreign nucleic acid molecule coding for a protein having the activity of a GFAT-2 is considerably higher than in plants having a foreign nucleic acid molecule coding for a protein having the activity of a GFAT-1. Furthermore, it can be seen from Example 21d) that individual plants comprising a foreign nucleic acid molecule coding for a protein having the activity of a bacterial GFAT contain even higher amounts of glucosaminoglycans than plants having a foreign nucleic acid molecule coding for a protein having the activity of a GFAT-2.

The results in Example 20b) show that plants comprising a foreign nucleic acid molecule coding for a protein having the activity of a UDP-glucose dehydrogenase and a nucleic acid molecule coding for a protein having the activity of a glucosaminoglycan synthase do not have any statistically significantly increased amounts of glucosaminoglycan compared to plants comprising only a foreign nucleic acid molecule coding for a protein having the activity of a glucosaminoglycan synthase.

To conclude, the results shown indicate that the considerable increases in the amounts of glucosaminoglycans in plants comprising foreign nucleic acid molecules coding for a protein having the activity of a UDP-glucose dehydrogenase and coding for a protein having the activity of a glucosaminoglycan synthase and having the activity of a GFAT-2 or having the activity of a bacterial GFAT is not due to the presence of the foreign nucleic acid molecules having the activity of a UDP-glucose dehydrogenase but to the presence of nucleic acid molecules having the activity of a GFAT-2 or having the activity of a bacterial GFAT.

Since hyaluronan synthases used in an exemplary manner as proteins having the activity of a glucosaminoglycan synthase require, as substrates, both UDP-Glc-NAc and UDP-GlcA, it may also be concluded from the results shown that the increased amounts of hyaluronan (glucosaminoglycan) are due to increased amounts of N-acetylated glucosamine derivatives and not to increased amounts of UDP-GlcA in these plants.

The invention claimed is:

1. A genetically modified plant cell or plant comprising a foreign nucleic acid molecule that codes for a protein having the activity of a glutamine:fructose 6-phosphate amidotransferase of isoform II (GFAT-2) or a protein having the activity of a bacterial glutamine:fructose 6-phosphate amidotransferase (bacterial GFAT), wherein said genetically modified plant cell or plant comprises a content of N-acetylated glucosamine derivatives of at least 2 μmol per gram of fresh weight.

2. A genetically modified plant cell or plant comprising a first foreign nucleic acid molecule coding for a protein having the activity of a GFAT-2 or bacterial GFAT and a second foreign nucleic acid molecule coding for a protein having the activity of a glucosaminoglycan synthase, wherein said genetically modified plant cell or plant comprises a content of glucosaminoglycans of at least 300 μg of glucosaminoglycan per gram of fresh weight.

3. A plant part comprising the plant cell of claim 1.

4. A plant part comprising the plant cell of claim 2.

5. Propagation material comprising the plant cell of claim 1.

6. Propagation material comprising the plant cell of claim 2.

7. A process for producing a genetically modified plant comprising:
   a) introducing a foreign nucleic acid molecule coding for a protein having the activity of a glutamine:fructose 6-phosphate amidotransferase of isoform II (GFAT-2) or coding for a protein having the activity of a bacterial glutamine:fructose 6-phosphate amidotransferase into a plant cell;
   b) regenerating a plant from plant cells obtained according to step a); and
   c) optionally, generating further plants with the aid of the plants according to step b).

8. A process for producing a plant which synthesizes glucosaminoglycan comprising
   a) genetically modifying a plant cell comprising steps i to ii in any order or carrying out any combinations of the following steps i to ii individually or simultaneously
      i) introducing a foreign nucleic acid molecule coding for a protein having the activity of a glutamine:fructose 6-phosphate amidotransferase of isoform II (GFAT-2) or coding for a protein having the activity of a bacterial glutamine:fructose 6-phosphate amidotransferase (bacterial GFAT) into a plant cell; and
      ii) introducing a foreign nucleic acid molecule coding for a glucosaminoglycan synthase into a plant cell;
   b) regenerating a plant from a plant cell comprising the genetic modification according to steps
      i) a) i
      ii) a) ii
      iii) a) i and a) ii,
   c) introducing into plant cells of plant according to step
      i) b) i a genetic modification according to step a)
      ii) b) ii a genetic modification according to step a) i, and regenerating a plant; and
   d) optionally, generating further plants with the aid of the plants obtained according to any of steps b) iii or c) i or c) ii.

9. A process for producing glucosaminoglycans comprising extracting glucosaminoglycans from the plant cell of claim 2.

10. A composition comprising a genetically modified plant cell of claim 1.

11. A process for producing flour comprising grinding the plant part of claim 3.

12. A process for producing glucosaminoglycans comprising extracting glucosaminoglycans from the plant part of claim 4.

13. A process for producing glucosaminoglycans comprising extracting glucosaminoglycans from the propagation material of claim 6.

14. A composition comprising a genetically modified plant cell of claim 2.

15. A process for producing flour comprising grinding the plant part of claim 4.

16. The genetically modified plant or plant cell of claim 1, wherein
   (i) the foreign nucleic acid molecule that codes for a protein having the activity of a GFAT-2 is
      a) a nucleic acid molecule coding for a protein having the amino acid sequence of SEQ ID NO: 7;
      b) a nucleic acid molecule coding for a protein having a sequence at least 95% identity to the amino acid sequence shown under SEQ ID NO: 7;
      c) a nucleic acid molecule comprising the nucleotide sequence of SEQ ID NO: 6 or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.1×SSC and 0.1% SDS; and
   (ii) the foreign nucleic acid molecule that codes for a protein having the activity of a bacterial GFAT is
      a) a nucleic acid molecule coding for a protein having the amino acid sequence of SEQ ID NO: 9;
      b) a nucleic acid molecule coding for a protein having a sequence at least 95% identity to the amino acid sequence shown under SEQ ID NO: 9;
      c) a nucleic acid molecule comprising the nucleotide sequence of SEQ ID NO: 8, SEQ ID NO: 10, or a sequence complementary thereto;

d) a nucleic acid molecule having at least 95% identity to the nucleic acid sequence of a) or c); or
e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

17. The genetically modified plant or plant cell of claim 2, wherein
   (i) the foreign nucleic acid molecule that codes for a protein having the activity of a GFAT-2 is
      a) a nucleic acid molecule coding for a protein having the amino acid sequence of SEQ ID NO: 7;
      b) a nucleic acid molecule coding for a protein having a sequence at least 95% identity to the amino acid sequence shown under SEQ ID NO: 7;
      c) a nucleic acid molecule comprising the nucleotide sequence of SEQ ID NO: 6 or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; and
   (ii) the foreign nucleic acid molecule that codes for a protein having the activity of a bacterial GFAT is
      a) a nucleic acid molecule coding for a protein having the amino acid sequence of SEQ ID NO: 9;
      b) a nucleic acid molecule coding for a protein having a sequence at least 95% identity to the amino acid sequence shown under SEQ ID NO: 9;
      c) a nucleic acid molecule comprising the nucleotide sequence of SEQ ID NO: 8, SEQ ID NO: 10, or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

18. The process of claim 7, wherein
   (i) the foreign nucleic acid molecule that codes for a protein having the activity of a GFAT-2 is
      a) a nucleic acid molecule coding for a protein having the amino acid sequence of SEQ ID NO: 7;
      b) a nucleic acid molecule coding for a protein having a sequence at least 95% identity to the amino acid sequence shown under SEQ ID NO: 7;
      c) a nucleic acid molecule comprising the nucleotide sequence of SEQ ID NO: 6 or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; and
   (ii) the foreign nucleic acid molecule that codes for a protein having the activity of a bacterial GFAT is
      a) a nucleic acid molecule coding for a protein having the amino acid sequence of SEQ ID NO: 9;
      b) a nucleic acid molecule coding for a protein having a sequence at least 95% identity to the amino acid sequence shown under SEQ ID NO: 9;
      c) a nucleic acid molecule comprising the nucleotide sequence of SEQ ID NO: 8, SEQ ID NO: 10, or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

19. The process of claim 8, wherein
   (i) the foreign nucleic acid molecule that codes for a protein having the activity of a GFAT-2 is
      a) a nucleic acid molecule coding for a protein having the amino acid sequence of SEQ ID NO: 7;
      b) a nucleic acid molecule coding for a protein having a sequence at least 95% identity to the amino acid sequence shown under SEQ ID NO: 7;
      c) a nucleic acid molecule comprising the nucleotide sequence of SEQ ID NO: 6 or a sequence complementary thereto;
      d) a nucleic acid molecule having at least 95% identity to the nucleic acid sequence of a) or c); or
      e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; and (ii) the foreign nucleic acid molecule that codes for a protein having the activity of a bacterial GFAT is
   a) a nucleic acid molecule coding for a protein having the amino acid sequence of SEQ ID NO: 9;
   b) a nucleic acid molecule coding for a protein having a sequence at least 95% identity to the amino acid sequence shown under SEQ ID NO: 9;
   c) a nucleic acid molecule comprising the nucleotide sequence of SEQ ID NO: 8, SEQ ID NO: 10, or a sequence complementary thereto;
   d) a nucleic acid molecule having at least 95% identity to the nucleic acid sequence of a) or c); or
   e) a nucleic acid molecule that hybridizes under stringent conditions with at least one strand of the nucleic acid sequences described under a) or c), wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

20. The genetically modified plant cell or plant of claim 16, wherein the plant cell or plant is potato, tomato, or rice.

21. The genetically modified plant cell or plant of claim 17, wherein the plant cell or plant is potato, tomato, or rice.

22. A genetically modified plant cell or plant comprising a foreign nucleic acid molecule that codes for a protein having the activity of a glutamine:fructose 6-phosphate amidotransferase of isoform II (GFAT-2) or a protein having the activity of a bacterial glutamine:fructose 6-phosphate amidotransferase (bacterial GFAT),
   wherein said genetically modified plant cell or plant comprises an increased content of N-acetylated glucosamine derivatives as compared to a wild-type plant cell or plant.

23. A genetically modified plant cell or plant comprising a first foreign nucleic acid molecule coding for a protein having the activity of a GFAT-2 or bacterial GFAT and a second foreign nucleic acid molecule coding for a protein having the activity of a glucosaminoglycan synthase,
   wherein said genetically modified plant cell or plant comprises an increased content of glucosaminoglycans as compared to a wild-type plant cell or plant.

24. The genetically modified plant cell or plant of claim 1, wherein said plant cell or plant comprises a content of N-acetylated glucosamine derivatives of at least 10 µmol per gram of fresh weight.

25. The genetically modified plant cell or plant of claim 1, wherein said plant cell or plant comprises a content of N-acetylated glucosamine derivatives of at least 15 µmol per gram of fresh weight.

26. The genetically modified plant cell or plant of claim 1, wherein said plant cell or plant comprises a content of N-acetylated glucosamine derivatives of at least 20 µmol per gram of fresh weight.

27. The genetically modified plant cell or plant of claim 2, wherein said plant cell or plant comprises a content of glucosaminoglycans of at least 500 µg of glucosaminoglycan per gram of fresh weight.

28. The genetically modified plant cell or plant of claim 2, wherein said plant cell or plant comprises a content of glucosaminoglycans of at least 1500 µg of glucosaminoglycan per gram of fresh weight.

29. The genetically modified plant cell or plant of claim 2, wherein said plant cell or plant comprises a content of glucosaminoglycans of at least 3500 µg of glucosaminoglycan per gram of fresh weight.

30. The genetically modified plant cell or plant of claim 2, wherein said plant cell or plant comprises a content of glucosaminoglycans of at least 4000 µg of glucosaminoglycan per gram of fresh weight.

31. The genetically modified plant cell or plant of claim 1, wherein the plant cell or plant is potato, tomato, or rice.

32. The genetically modified plant cell or plant of claim 2, wherein the plant cell or plant is potato, tomato, or rice.

33. The process of claim 18, wherein the plant cell is potato, tomato, or rice.

34. The process of claim 19, wherein the plant cell is potato, tomato, or rice.

35. The genetically modified plant cell or plant of claim 24, wherein the plant cell or plant is potato, tomato, or rice.

36. The genetically modified plant cell or plant of claim 25, wherein the plant cell or plant is potato, tomato, or rice.

37. The genetically modified plant cell or plant of claim 26, wherein the plant cell or plant is potato, tomato, or rice.

38. The genetically modified plant cell or plant of claim 27, wherein the plant cell or plant is potato, tomato, or rice.

39. The genetically modified plant cell or plant of claim 28, wherein the plant cell or plant is potato, tomato, or rice.

40. The genetically modified plant cell or plant of claim 29, wherein the plant cell or plant is potato, tomato, or rice.

41. The genetically modified plant cell or plant of claim 30, wherein the plant cell or plant is potato, tomato, or rice.

* * * * *

SEQUENCE LISTING

```
<160> NUMBER OF SEQ ID NOS: 17

<210> SEQ ID NO 1
<211> LENGTH: 1707
<212> TYPE: DNA
<213> ORGANISM: Paramecium bursaria Chlorella Virus 1
<220> FEATURE:
<221> NAME/KEY: CDS
<222> LOCATION: (1)..(1707)
<300> PUBLICATION INFORMATION:
<308> DATABASE ACCESSION NUMBER: PB42580
<309> DATABASE ENTRY DATE: 1995-12-24
<313> RELEVANT RESIDUES IN SEQ ID NO: (50903)..(52609)

<400> SEQUENCE: 1 atg ggt aaa aat ata atc ata atg gtt tcg tgg tac acc atc ata act        48
Met Gly Lys Asn Ile Ile Ile Met Val Ser Trp Tyr Thr Ile Ile Thr
1               5                   10                  15 tca aat cta atc gcg gtt gga gga gcc tct cta atc ttg gct ccg gca        96
Ser Asn Leu Ile Ala Val Gly Gly Ala Ser Leu Ile Leu Ala Pro Ala
                20                  25                  30 att act ggg tat gtt cta cat tgg aat att gct ctc tcg aca atc tgg       144
Ile Thr Gly Tyr Val Leu His Trp Asn Ile Ala Leu Ser Thr Ile Trp
            35                  40                  45 gga gta tca gct tat ggt att ttc gtt ttt ggg ttt ttc ctt gca caa       192
Gly Val Ser Ala Tyr Gly Ile Phe Val Phe Gly Phe Phe Leu Ala Gln
        50                  55                  60 gtt tta ttt tca gaa ctg aac agg aaa cgt ctt cgc aag tgg att tct       240
Val Leu Phe Ser Glu Leu Asn Arg Lys Arg Leu Arg Lys Trp Ile Ser
65                  70                  75                  80 ctc aga cct aag ggt tgg aat gat gtt cgt ttg gct gtg atc att gct       288
Leu Arg Pro Lys Gly Trp Asn Asp Val Arg Leu Ala Val Ile Ile Ala
                85                  90                  95 gga tat cgc gag gat cct tat atg ttc cag aag tgc ctc gag tct gta       336
Gly Tyr Arg Glu Asp Pro Tyr Met Phe Gln Lys Cys Leu Glu Ser Val
            100                 105                 110 cgt gac tct gat tat ggc aac gtt gcc cgt ctg att tgt gtg att gac       384
Arg Asp Ser Asp Tyr Gly Asn Val Ala Arg Leu Ile Cys Val Ile Asp
        115                 120                 125 ggt gat gag gac gat gat atg agg atg gct gcc gtt tac aag gcg atc       432
Gly Asp Glu Asp Asp Asp Met Arg Met Ala Ala Val Tyr Lys Ala Ile
    130                 135                 140 tac aat gat aat atc aag aag ccc gag ttt gtt ctg tgt gag tca gac       480
Tyr Asn Asp Asn Ile Lys Lys Pro Glu Phe Val Leu Cys Glu Ser Asp
145                 150                 155                 160 gac aag gaa ggt gaa cgc atc gac tct gat ttc tct cgc gac att tgt       528
Asp Lys Glu Gly Glu Arg Ile Asp Ser Asp Phe Ser Arg Asp Ile Cys
                165                 170                 175
```

```
gtc ctc cag cct cat cgt gga aaa cgg gag tgt ctt tat act ggg ttt     576
Val Leu Gln Pro His Arg Gly Lys Arg Glu Cys Leu Tyr Thr Gly Phe
            180                 185                 190 caa ctt gca aag atg gac ccc agt gtc aat gct gtc gtt ctg att gac     624
Gln Leu Ala Lys Met Asp Pro Ser Val Asn Ala Val Val Leu Ile Asp
        195                 200                 205 agc gat acc gtt ctc gag aag gat gct att ctg gaa gtt gta tac cca     672
Ser Asp Thr Val Leu Glu Lys Asp Ala Ile Leu Glu Val Val Tyr Pro
    210                 215                 220 ctt gca tgc gat ccc gag atc caa gcc gtt gca ggt gag tgt aag att     720
Leu Ala Cys Asp Pro Glu Ile Gln Ala Val Ala Gly Glu Cys Lys Ile
225                 230                 235                 240 tgg aac aca gac act ctt ttg agt ctt ctc gtc gct tgg cgg tac tat     768
Trp Asn Thr Asp Thr Leu Leu Ser Leu Leu Val Ala Trp Arg Tyr Tyr
                245                 250                 255 tct gcg ttt tgt gtg gag agg agt gcc cag tct ttt ttc agg act gtt     816
Ser Ala Phe Cys Val Glu Arg Ser Ala Gln Ser Phe Phe Arg Thr Val
            260                 265                 270 cag tgc gtt ggg ggg cca ctg ggt gcc tac aag att gat atc att aag     864
Gln Cys Val Gly Gly Pro Leu Gly Ala Tyr Lys Ile Asp Ile Ile Lys
        275                 280                 285 gag att aag gac ccc tgg att tcc cag cgc ttt ctt ggt cag aag tgt     912
Glu Ile Lys Asp Pro Trp Ile Ser Gln Arg Phe Leu Gly Gln Lys Cys
    290                 295                 300 act tac ggt gac gac cgc cgg cta acc aac gag atc ttg atg cgt ggt     960
Thr Tyr Gly Asp Asp Arg Arg Leu Thr Asn Glu Ile Leu Met Arg Gly
305                 310                 315                 320 aaa aag gtt gtg ttc act cca ttt gct gtt ggt tgg tct gac agt ccg    1008
Lys Lys Val Val Phe Thr Pro Phe Ala Val Gly Trp Ser Asp Ser Pro
                325                 330                 335 acc aat gtg ttt cgg tac atc gtt cag cag acc cgc tgg agt aag tcg    1056
Thr Asn Val Phe Arg Tyr Ile Val Gln Gln Thr Arg Trp Ser Lys Ser
            340                 345                 350 tgg tgc cgc gaa att tgg tac acc ctc ttc gcc gcg tgg aag cac ggt    1104
Trp Cys Arg Glu Ile Trp Tyr Thr Leu Phe Ala Ala Trp Lys His Gly
        355                 360                 365 ttg tct gga att tgg ctg gcc ttt gaa tgt ttg tat caa att aca tac    1152
Leu Ser Gly Ile Trp Leu Ala Phe Glu Cys Leu Tyr Gln Ile Thr Tyr
    370                 375                 380 ttc ttc ctc gtg att tac ctc ttt tct cgc cta gcc gtt gag gcc gac    1200
Phe Phe Leu Val Ile Tyr Leu Phe Ser Arg Leu Ala Val Glu Ala Asp
385                 390                 395                 400 cct cgc gcc cag aca gcc acg gtg att gtg agc acc acg gtt gca ttg    1248
Pro Arg Ala Gln Thr Ala Thr Val Ile Val Ser Thr Thr Val Ala Leu
                405                 410                 415 att aag tgt ggg tat ttt tca ttc cga gcc aag gat att cgg gcg ttt    1296
Ile Lys Cys Gly Tyr Phe Ser Phe Arg Ala Lys Asp Ile Arg Ala Phe
            420                 425                 430 tac ttt gtg ctt tat aca ttt gtt tac ttt ttc tgt atg att ccg gcc    1344
Tyr Phe Val Leu Tyr Thr Phe Val Tyr Phe Phe Cys Met Ile Pro Ala
        435                 440                 445 agg att act gca atg atg acg ctt tgg gac att ggc tgg ggt act cgc    1392
Arg Ile Thr Ala Met Met Thr Leu Trp Asp Ile Gly Trp Gly Thr Arg
    450                 455                 460 ggt gga aac gag aag cct tcc gtt ggc acc cgg gtc gct ctg tgg gca    1440
Gly Gly Asn Glu Lys Pro Ser Val Gly Thr Arg Val Ala Leu Trp Ala
465                 470                 475                 480 aag caa tat ctc att gca tat atg tgg tgg gcc gcg gtt gtt ggc gct    1488
Lys Gln Tyr Leu Ile Ala Tyr Met Trp Trp Ala Ala Val Val Gly Ala
                485                 490                 495
```

```
gga gtt tac agc atc gtc cat aac tgg atg ttc gat tgg aat tct ctt    1536
Gly Val Tyr Ser Ile Val His Asn Trp Met Phe Asp Trp Asn Ser Leu
        500                 505                 510 tct tat cgt ttt gct ttg gtt ggt att tgt tct tac att gtt ttt att    1584
Ser Tyr Arg Phe Ala Leu Val Gly Ile Cys Ser Tyr Ile Val Phe Ile
        515                 520                 525 gtt att gtg ctg gtg gtt tat ttc acc ggc aaa att acg act tgg aat    1632
Val Ile Val Leu Val Val Tyr Phe Thr Gly Lys Ile Thr Thr Trp Asn
530                 535                 540 ttc acg aag ctt cag aag gag cta atc gag gat cgc gtt ctg tac gat    1680
Phe Thr Lys Leu Gln Lys Glu Leu Ile Glu Asp Arg Val Leu Tyr Asp
545                 550                 555                 560 gca act acc aat gct cag tct gtg tga                                1707
Ala Thr Thr Asn Ala Gln Ser Val
                565

<210> SEQ ID NO 2
<211> LENGTH: 568
<212> TYPE: PRT
<213> ORGANISM: Paramecium bursaria Chlorella Virus 1

<400> SEQUENCE: 2

Met Gly Lys Asn Ile Ile Met Val Ser Trp Tyr Thr Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
```

```
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Phe Cys Met Ile Pro Ala
        435                 440                 445

Arg Ile Thr Ala Met Met Thr Leu Trp Asp Ile Gly Trp Gly Thr Arg
    450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
                485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
        515                 520                 525

Val Ile Val Leu Val Val Tyr Phe Thr Gly Lys Ile Thr Thr Trp Asn
    530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565
```

<210> SEQ ID NO 3
<211> LENGTH: 1707
<212> TYPE: DNA
<213> ORGANISM: Artificial Sequence
<220> FEATURE:
<223> OTHER INFORMATION: Synthetic sequence encoding Paramecium bursaria Chlorella Virus Hyaluronansynthase protein

<400> SEQUENCE: 3

```
atgggtaaga acattatcat tatggtgtcc tggtacacaa ttattacaag taatctcatc     60
gcagttggtg gtgcatctct tattctcgct ccagctatca ctggatatgt tcttcactgg    120
aacatcgccc tctcaactat ttggggagtt tccgcatatg gtatttttgt tttcgggttc    180
tttttggctc aggttctgtt ctcagagctc aatcgtaaga gactcaggaa gtggattagc    240
cttagaccaa aggggtggaa tgacgttcgt ctcgctgtca ttatcgctgg ctaccgtgaa    300
gatccttaca tgtttcaaaa gtgcttggaa tcagttaggg atagtgatta tggcaacgtc    360
gctagactga tctgtgtgat tgatggagat gaggacgacg atatgaggat ggcagctgtt    420
```

```
tataaggcta tctataatga taacattaag aagcctgaat tgttcttg cgagtctgat      480
gacaaggaag gagaacggat tgattcagat ttctcacgtg atatctgcgt tctccaacct    540
catcgtggga agcgtgaatg tctttataca ggtttccaac tcgccaaaat ggacccatca    600
gtgaacgctg tggttcttat cgatagtgat actgtgctgg agaaagatgc tatcttggag    660
gttgtttacc ctcttgcctg tgatcctgaa attcaagctg tggctggaga gtgcaagatc    720
tggaacacag atactcttct ttctctgctt gtcgcatgga gatattactc cgcattctgt    780
gtggagagga gcgctcaatc cttttttccgt accgttcaat gcgttggtgg tcctttggga    840
gcttacaaaa ttgatatcat caaggagatt aaggacccat ggattagtca aaggtttctt    900
ggtcagaagt gcacttatgg cgatgatcgt agattgacta cgaaatcct tatgaggggc     960
aagaaagtcg ttttactcc atttgctgtc ggatggtctg attcacctac aaatgttttc   1020
cgttatattg tgcaacaaac acgttggagt aagagctggt gtagggagat ctggtacact   1080
ttgttcgctg cttggaagca cgggcttagc ggaatttggc ttgcttttga atgcctttac   1140
cagattacat acttttctt ggtgatctat ttgttttcac gtcttgccgt cgaggctgac    1200
cctagagcac agactgcaac tgtgattgtt tctactacag tcgcacttat taagtgtggc   1260
tatttcagtt ttagagcaaa agatattaga gccttctatt tgttttgta cacatttgtt    1320
tatttctttt gcatgattcc agctcgtatt accgctatga tgaccttgtg ggacatcgga   1380
tggggaacta gaggtggtaa cgaaaagcct tctgtgggaa caagggtggc cctttgggca   1440
aaacaatatc tcatcgccta catgtggtgg gccgctgtcg ttggtgccgg agtgtactca   1500
atcgttcata actggatgtt tgactggaac tctttgagct atcgtttcgc tcttgtgggt   1560
atttgttctt acattgtttt catcgtgatt gtgctcgttg tgtatttcac tggtaaaatc   1620
acaacctgga atttcactaa acttcaaaag gaattgattg aagacagggt tctgtatgat   1680
gctactacca acgcccagtc agtttaa                                       1707

<210> SEQ ID NO 4
<211> LENGTH: 2298
<212> TYPE: DNA
<213> ORGANISM: Mus musculus
<220> FEATURE:
<221> NAME/KEY: CDS
<222> LOCATION: (150)..(2192)
<300> PUBLICATION INFORMATION:
<308> DATABASE ACCESSION NUMBER: BC050762.1
<309> DATABASE ENTRY DATE: 2005-03-08
<313> RELEVANT RESIDUES IN SEQ ID NO: (150)..(2195)

<400> SEQUENCE: 4
gagagcgaag cgagcgctga gtcggactgt cgggtctgag ctgtcgcatc ccagagtcct     60
ctcattgcca ccaccccggc ccgagctcac cctcgcttct gaagctctcc gcgcgcccga    120
cagctcagcc ctcgccgtg accaacatc atg tgc ggt ata ttt gct tat tta      173
                                Met Cys Gly Ile Phe Ala Tyr Leu
                                  1               5 aat tac cat gtt cct cga aca aga cga gaa atc ttg gag aca cta atc     221
Asn Tyr His Val Pro Arg Thr Arg Arg Glu Ile Leu Glu Thr Leu Ile
         10                  15                  20 aaa ggc ctt cag aga ctg gaa tac aga gga tat gat tct gct ggt gtg     269
Lys Gly Leu Gln Arg Leu Glu Tyr Arg Gly Tyr Asp Ser Ala Gly Val
 25                  30                  35                  40 gga ctt gac gga ggc aat gac aaa gac tgg gaa gcc aac gcc tgc aaa     317
Gly Leu Asp Gly Gly Asn Asp Lys Asp Trp Glu Ala Asn Ala Cys Lys
                 45                  50                  55
```

```
atc cag ctc att aag aag aaa gga aaa gtt aag gca ctg gat gaa gaa    365
Ile Gln Leu Ile Lys Lys Lys Gly Lys Val Lys Ala Leu Asp Glu Glu
            60              65              70 gtt cac aaa caa caa gat atg gac ttg gat ata gaa ttt gat gtg cat    413
Val His Lys Gln Gln Asp Met Asp Leu Asp Ile Glu Phe Asp Val His
     75              80              85 ctt gga ata gct cat acc cgt tgg gcg aca cat gga gaa ccc aat cct    461
Leu Gly Ile Ala His Thr Arg Trp Ala Thr His Gly Glu Pro Asn Pro
 90              95             100 gtc aat agt cac ccc cag cgc tct gat aaa aat aat gaa ttc att gtt    509
Val Asn Ser His Pro Gln Arg Ser Asp Lys Asn Asn Glu Phe Ile Val
105             110             115             120 att cat aat gga atc atc acc aac tac aaa gac ttg aaa aag ttt ctg    557
Ile His Asn Gly Ile Ile Thr Asn Tyr Lys Asp Leu Lys Lys Phe Leu
                125             130             135 gaa agc aaa ggc tat gac ttt gaa tct gaa aca gac aca gaa acc att    605
Glu Ser Lys Gly Tyr Asp Phe Glu Ser Glu Thr Asp Thr Glu Thr Ile
            140             145             150 gcc aag ctc gtc aag tac atg tat gac aac tgg gag agc cag gac gtc    653
Ala Lys Leu Val Lys Tyr Met Tyr Asp Asn Trp Glu Ser Gln Asp Val
        155             160             165 agt ttt acc acc ttg gtg gag aga gtt atc caa caa ttg gaa ggc gcc    701
Ser Phe Thr Thr Leu Val Glu Arg Val Ile Gln Gln Leu Glu Gly Ala
170             175             180 ttt gct ctt gtg ttt aaa agt gtc cat ttt ccc ggg caa gca gtt ggc    749
Phe Ala Leu Val Phe Lys Ser Val His Phe Pro Gly Gln Ala Val Gly
185             190             195             200 aca agg cga ggt agc cct ctc ttg att ggt gtg cgg agt gaa cat aag    797
Thr Arg Arg Gly Ser Pro Leu Leu Ile Gly Val Arg Ser Glu His Lys
            205             210             215 ctt tct aca gat cac att ccg att ctg tac aga aca ggc aaa gac aag    845
Leu Ser Thr Asp His Ile Pro Ile Leu Tyr Arg Thr Gly Lys Asp Lys
        220             225             230 aaa gga agc tgc ggt ctt tcc cgt gtg gac agc acg aca tgc ctg ttc    893
Lys Gly Ser Cys Gly Leu Ser Arg Val Asp Ser Thr Thr Cys Leu Phe
235             240             245 cct gtt gag gaa aag gca gtt gaa tat tac ttt gct tct gat gca agt    941
Pro Val Glu Glu Lys Ala Val Glu Tyr Tyr Phe Ala Ser Asp Ala Ser
250             255             260 gcc gtg ata gag cac acc aat cgt gtc atc ttt ctg gaa gat gat gat    989
Ala Val Ile Glu His Thr Asn Arg Val Ile Phe Leu Glu Asp Asp Asp
265             270             275             280 gtt gca gca gtg gtg gat ggc cgt ctc tct atc cac cga att aaa cga   1037
Val Ala Ala Val Val Asp Gly Arg Leu Ser Ile His Arg Ile Lys Arg
            285             290             295 act gca gga gac cat cct ggc cga gct gtg caa act ctc cag atg gag   1085
Thr Ala Gly Asp His Pro Gly Arg Ala Val Gln Thr Leu Gln Met Glu
        300             305             310 ctc cag cag atc atg aag ggc aac ttt agt tca ttt atg cag aag gaa   1133
Leu Gln Gln Ile Met Lys Gly Asn Phe Ser Ser Phe Met Gln Lys Glu
315             320             325 att ttt gag cag cca gaa tct gtt gtg aac aca atg aga gga aga gtc   1181
Ile Phe Glu Gln Pro Glu Ser Val Val Asn Thr Met Arg Gly Arg Val
330             335             340 aat ttt gat gac tac act gtg aat ttg gga ggt ttg aaa gat cac att   1229
Asn Phe Asp Asp Tyr Thr Val Asn Leu Gly Gly Leu Lys Asp His Ile
345             350             355             360 aag gag atc cag cgg tgt cgg cgg ttg att ctt att gct tgt ggc aca   1277
Lys Glu Ile Gln Arg Cys Arg Arg Leu Ile Leu Ile Ala Cys Gly Thr
            365             370             375
```

```
agt tac cac gct ggt gtg gca acc cgt cag gtc ctg gag gag ctg acc    1325
Ser Tyr His Ala Gly Val Ala Thr Arg Gln Val Leu Glu Glu Leu Thr
            380                 385                 390 gag ctg ccc gtg atg gtg gag ctt gcc agt gac ttc ttg gat aga aac    1373
Glu Leu Pro Val Met Val Glu Leu Ala Ser Asp Phe Leu Asp Arg Asn
        395                 400                 405 act cca gtc ttt cga gat gat gtt tgc ttt ttc att agt caa tca ggc    1421
Thr Pro Val Phe Arg Asp Asp Val Cys Phe Phe Ile Ser Gln Ser Gly
    410                 415                 420 gag aca gct gac acc ctg atg gga ctt cgt tac tgt aag gag aga gga    1469
Glu Thr Ala Asp Thr Leu Met Gly Leu Arg Tyr Cys Lys Glu Arg Gly
425                 430                 435                 440 gcc tta act gtg ggg atc aca aat aca gtc ggc agt tct ata tca agg    1517
Ala Leu Thr Val Gly Ile Thr Asn Thr Val Gly Ser Ser Ile Ser Arg
                445                 450                 455 gag aca gat tgc ggg gtt cat att aat gct ggt cct gag att ggc gtg    1565
Glu Thr Asp Cys Gly Val His Ile Asn Ala Gly Pro Glu Ile Gly Val
            460                 465                 470 gcc agt aca aag gca tac acc agc cag ttt gtg tcc ctc gtg atg ttt    1613
Ala Ser Thr Lys Ala Tyr Thr Ser Gln Phe Val Ser Leu Val Met Phe
        475                 480                 485 gct ctc atg atg tgt gat gac agg atc tcc atg caa gag aga cgc aaa    1661
Ala Leu Met Met Cys Asp Asp Arg Ile Ser Met Gln Glu Arg Arg Lys
    490                 495                 500 gag atc atg ctc gga ctg aag cga ctg ccg gac ttg att aag gaa gtg    1709
Glu Ile Met Leu Gly Leu Lys Arg Leu Pro Asp Leu Ile Lys Glu Val
505                 510                 515                 520 ctg agc atg gat gat gaa atc cag aag ctg gcg acg gag ctt tac cac    1757
Leu Ser Met Asp Asp Glu Ile Gln Lys Leu Ala Thr Glu Leu Tyr His
                525                 530                 535 cag aag tcg gtc ctg ata atg ggg cgg ggc tac cat tat gct aca tgc    1805
Gln Lys Ser Val Leu Ile Met Gly Arg Gly Tyr His Tyr Ala Thr Cys
            540                 545                 550 ctt gaa ggg gct ctg aaa atc aag gag att act tat atg cat tcg gaa    1853
Leu Glu Gly Ala Leu Lys Ile Lys Glu Ile Thr Tyr Met His Ser Glu
        555                 560                 565 ggc atc ctt gct ggt gag ctc aag cac ggc cct ctg gcc ttg gtg gac    1901
Gly Ile Leu Ala Gly Glu Leu Lys His Gly Pro Leu Ala Leu Val Asp
    570                 575                 580 aag ttg atg cct gtc atc atg atc atg cga gac cac act tat gcc        1949
Lys Leu Met Pro Val Ile Met Ile Met Arg Asp His Thr Tyr Ala
585                 590                 595                 600 aag tgc cag aac gct ctt cag cag gtg gtt gca cgg cag ggg cgt cca    1997
Lys Cys Gln Asn Ala Leu Gln Gln Val Val Ala Arg Gln Gly Arg Pro
                605                 610                 615 gtc gtg atc tgt gat aag gag gat act gag acc att aag aat aca aaa    2045
Val Val Ile Cys Asp Lys Glu Asp Thr Glu Thr Ile Lys Asn Thr Lys
            620                 625                 630 agg aca atc aag gtg ccc cac tca gtg gac tgc ttg cag ggc att ctc    2093
Arg Thr Ile Lys Val Pro His Ser Val Asp Cys Leu Gln Gly Ile Leu
        635                 640                 645 agt gtg att ccc ctg cag ctg ctg gct ttc cac ctg gct gtg ctg aga    2141
Ser Val Ile Pro Leu Gln Leu Leu Ala Phe His Leu Ala Val Leu Arg
    650                 655                 660 ggc tac gat gtt gat ttt cca cgg aat ctt gcc aaa tct gta aca gta    2189
Gly Tyr Asp Val Asp Phe Pro Arg Asn Leu Ala Lys Ser Val Thr Val
665                 670                 675                 680 gag taacagacac ctgaaactta agacagttaa gcaacacgag atacctttg          2242
Glu tatttaaatt tttgatttaa actatcaaaa aaaaaaaaaa aaaaaaaaaa aaaaaa      2298
```

<210> SEQ ID NO 5
<211> LENGTH: 681
<212> TYPE: PRT
<213> ORGANISM: Mus musculus

<400> SEQUENCE: 5

```
Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30

Arg Gly Tyr Asp Ser Ala Gly Val Gly Leu Asp Gly Gly Asn Asp Lys
        35                  40                  45

Asp Trp Glu Ala Asn Ala Cys Lys Ile Gln Leu Ile Lys Lys Lys Gly
    50                  55                  60

Lys Val Lys Ala Leu Asp Glu Glu Val His Lys Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Asn Pro Val Asn Ser His Pro Gln Arg Ser
            100                 105                 110

Asp Lys Asn Asn Glu Phe Ile Val Ile His Asn Gly Ile Ile Thr Asn
        115                 120                 125

Tyr Lys Asp Leu Lys Lys Phe Leu Glu Ser Lys Gly Tyr Asp Phe Glu
    130                 135                 140

Ser Glu Thr Asp Thr Glu Thr Ile Ala Lys Leu Val Lys Tyr Met Tyr
145                 150                 155                 160

Asp Asn Trp Glu Ser Gln Asp Val Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
        195                 200                 205

Ile Gly Val Arg Ser Glu His Lys Leu Ser Thr Asp His Ile Pro Ile
    210                 215                 220

Leu Tyr Arg Thr Gly Lys Asp Lys Lys Gly Ser Cys Gly Leu Ser Arg
225                 230                 235                 240

Val Asp Ser Thr Thr Cys Leu Phe Pro Val Glu Glu Lys Ala Val Glu
                245                 250                 255

Tyr Tyr Phe Ala Ser Asp Ala Ser Ala Val Ile Glu His Thr Asn Arg
            260                 265                 270

Val Ile Phe Leu Glu Asp Asp Val Ala Ala Val Val Asp Gly Arg
        275                 280                 285

Leu Ser Ile His Arg Ile Lys Arg Thr Ala Gly Asp His Pro Gly Arg
    290                 295                 300

Ala Val Gln Thr Leu Gln Met Glu Leu Gln Gln Ile Met Lys Gly Asn
305                 310                 315                 320

Phe Ser Ser Phe Met Gln Lys Glu Ile Phe Glu Gln Pro Glu Ser Val
                325                 330                 335

Val Asn Thr Met Arg Gly Arg Val Asn Phe Asp Asp Tyr Thr Val Asn
            340                 345                 350

Leu Gly Gly Leu Lys Asp His Ile Lys Glu Ile Gln Arg Cys Arg Arg
        355                 360                 365

Leu Ile Leu Ile Ala Cys Gly Thr Ser Tyr His Ala Gly Val Ala Thr
    370                 375                 380
```

```
Arg Gln Val Leu Glu Glu Leu Thr Glu Leu Pro Val Met Val Glu Leu
385                 390                 395                 400

Ala Ser Asp Phe Leu Asp Arg Asn Thr Pro Val Phe Arg Asp Asp Val
            405                 410                 415

Cys Phe Phe Ile Ser Gln Ser Gly Glu Thr Ala Asp Thr Leu Met Gly
        420                 425                 430

Leu Arg Tyr Cys Lys Glu Arg Gly Ala Leu Thr Val Gly Ile Thr Asn
    435                 440                 445

Thr Val Gly Ser Ser Ile Ser Arg Glu Thr Asp Cys Gly Val His Ile
450                 455                 460

Asn Ala Gly Pro Glu Ile Gly Val Ala Ser Thr Lys Ala Tyr Thr Ser
465                 470                 475                 480

Gln Phe Val Ser Leu Val Met Phe Ala Leu Met Met Cys Asp Asp Arg
            485                 490                 495

Ile Ser Met Gln Glu Arg Arg Lys Glu Ile Met Leu Gly Leu Lys Arg
        500                 505                 510

Leu Pro Asp Leu Ile Lys Glu Val Leu Ser Met Asp Asp Glu Ile Gln
    515                 520                 525

Lys Leu Ala Thr Glu Leu Tyr His Gln Lys Ser Val Leu Ile Met Gly
530                 535                 540

Arg Gly Tyr His Tyr Ala Thr Cys Leu Glu Gly Ala Leu Lys Ile Lys
545                 550                 555                 560

Glu Ile Thr Tyr Met His Ser Glu Gly Ile Leu Ala Gly Glu Leu Lys
            565                 570                 575

His Gly Pro Leu Ala Leu Val Asp Lys Leu Met Pro Val Ile Met Ile
        580                 585                 590

Ile Met Arg Asp His Thr Tyr Ala Lys Cys Gln Asn Ala Leu Gln Gln
    595                 600                 605

Val Val Ala Arg Gln Gly Arg Pro Val Val Ile Cys Asp Lys Glu Asp
610                 615                 620

Thr Glu Thr Ile Lys Asn Thr Lys Arg Thr Ile Lys Val Pro His Ser
625                 630                 635                 640

Val Asp Cys Leu Gln Gly Ile Leu Ser Val Ile Pro Leu Gln Leu Leu
            645                 650                 655

Ala Phe His Leu Ala Val Leu Arg Gly Tyr Asp Val Asp Phe Pro Arg
        660                 665                 670

Asn Leu Ala Lys Ser Val Thr Val Glu
    675                 680

<210> SEQ ID NO 6
<211> LENGTH: 2049
<212> TYPE: DNA
<213> ORGANISM: Mus musculus
<220> FEATURE:
<221> NAME/KEY: CDS
<222> LOCATION: (1)..(2046)
<300> PUBLICATION INFORMATION:
<308> DATABASE ACCESSION NUMBER: BC031928.1
<309> DATABASE ENTRY DATE: 2003-10-07
<313> RELEVANT RESIDUES IN SEQ ID NO: (51)..(299)

<400> SEQUENCE: 6 atg tgc gga atc ttt gcc tac atg aat tac aga gtt ccc aag aca agg     48
Met Cys Gly Ile Phe Ala Tyr Met Asn Tyr Arg Val Pro Lys Thr Arg
1               5                   10                  15 aaa gag att ttc gaa acc ctt atc agg ggt ctg cag cgg ctg gag tac     96
Lys Glu Ile Phe Glu Thr Leu Ile Arg Gly Leu Gln Arg Leu Glu Tyr
            20                  25                  30
```

| | | | | | | | | | | | | | | |
|---|---|---|---|---|---|---|---|---|---|---|---|---|---|---|
| cgg | ggc | tat | gac | tct | gcg | ggg | gtt | gcc | att | gat | ggg | aat | aac cac gaa | 144 |
| Arg | Gly | Tyr | Asp | Ser | Ala | Gly | Val | Ala | Ile | Asp | Gly | Asn | Asn His Glu | |
| | 35 | | | | 40 | | | | 45 | | | | | |

| gtc | aaa | gaa | aga | cac | atc | cat | ctt | gtg | aag | aaa | agg | ggg | aaa gta aag | 192 |
| Val | Lys | Glu | Arg | His | Ile | His | Leu | Val | Lys | Lys | Arg | Gly | Lys Val Lys | |
| 50 | | | | | 55 | | | | 60 | | | | | |

| gct | ctg | gat | gaa | gaa | ctt | tac | aag | caa | gat | agc | atg | gac | ttg aag gtg | 240 |
| Ala | Leu | Asp | Glu | Glu | Leu | Tyr | Lys | Gln | Asp | Ser | Met | Asp | Leu Lys Val | |
| 65 | | | | | 70 | | | | | 75 | | | | 80 |

| gag | ttt | gag | aca | cac | ttc | ggc | att | gcc | cac | aca | cgt | tgg | gcc acc cac | 288 |
| Glu | Phe | Glu | Thr | His | Phe | Gly | Ile | Ala | His | Thr | Arg | Trp | Ala Thr His | |
| | | | | 85 | | | | | 90 | | | | 95 | |

| ggg | gtt | ccc | aat | gct | gtc | aac | agt | cac | ccg | cag | cgt | tcg | gac aaa gac | 336 |
| Gly | Val | Pro | Asn | Ala | Val | Asn | Ser | His | Pro | Gln | Arg | Ser | Asp Lys Asp | |
| | | | 100 | | | | | 105 | | | | 110 | | |

| aat | gaa | ttt | gtt | gtc | atc | cac | aac | ggg | atc | atc | act | aat | tac aag gat | 384 |
| Asn | Glu | Phe | Val | Val | Ile | His | Asn | Gly | Ile | Ile | Thr | Asn | Tyr Lys Asp | |
| | | | 115 | | | | | 120 | | | | | 125 | |

| cta | agg | aag | ttt | ctg | gaa | agc | aaa | ggc | tac | gag | ttt | gag | tca gaa aca | 432 |
| Leu | Arg | Lys | Phe | Leu | Glu | Ser | Lys | Gly | Tyr | Glu | Phe | Glu | Ser Glu Thr | |
| 130 | | | | | 135 | | | | | 140 | | | | |

| gac | acg | gag | acc | atc | gcc | aag | ctg | att | aaa | tat | gta | ttt | gac aac aga | 480 |
| Asp | Thr | Glu | Thr | Ile | Ala | Lys | Leu | Ile | Lys | Tyr | Val | Phe | Asp Asn Arg | |
| 145 | | | | | 150 | | | | | 155 | | | | 160 |

| gag | act | gag | gac | ata | acg | ttt | tcc | aca | ttg | gtc | gaa | aga | gtc att cag | 528 |
| Glu | Thr | Glu | Asp | Ile | Thr | Phe | Ser | Thr | Leu | Val | Glu | Arg | Val Ile Gln | |
| | | | | | 165 | | | | | 170 | | | | 175 |

| cag | ttg | gaa | ggc | gcc | ttt | gca | ctg | gtt | ttc | aag | agt | att | cac tac ccg | 576 |
| Gln | Leu | Glu | Gly | Ala | Phe | Ala | Leu | Val | Phe | Lys | Ser | Ile | His Tyr Pro | |
| | | | | 180 | | | | | 185 | | | | 190 | |

| gga | gaa | gct | gtc | gcc | acg | agg | aga | ggc | agc | ccc | ttg | ctc | atc ggg gta | 624 |
| Gly | Glu | Ala | Val | Ala | Thr | Arg | Arg | Gly | Ser | Pro | Leu | Leu | Ile Gly Val | |
| | | | | | 195 | | | | 200 | | | | | 205 |

| cga | agc | aaa | tac | aaa | ctc | tcc | aca | gag | cag | atc | ccc | gtc | tta tat ccg | 672 |
| Arg | Ser | Lys | Tyr | Lys | Leu | Ser | Thr | Glu | Gln | Ile | Pro | Val | Leu Tyr Pro | |
| | 210 | | | | | 215 | | | | | 220 | | | |

| aca | tgc | aat | atc | gag | aat | gtg | aag | aat | atc | tgc | aag | act | agg atg aag | 720 |
| Thr | Cys | Asn | Ile | Glu | Asn | Val | Lys | Asn | Ile | Cys | Lys | Thr | Arg Met Lys | |
| 225 | | | | | 230 | | | | | 235 | | | | 240 |

| aga | ctg | gac | agc | tcc | acc | tgc | ctg | cac | gct | gtg | ggc | gat | aaa gct gtg | 768 |
| Arg | Leu | Asp | Ser | Ser | Thr | Cys | Leu | His | Ala | Val | Gly | Asp | Lys Ala Val | |
| | | | | 245 | | | | | 250 | | | | 255 | |

| gaa | ttc | ttc | ttt | gct | tct | gat | gca | agt | gcc | atc | ata | gaa | cac acc aac | 816 |
| Glu | Phe | Phe | Phe | Ala | Ser | Asp | Ala | Ser | Ala | Ile | Ile | Glu | His Thr Asn | |
| | | | 260 | | | | | 265 | | | | 270 | | |

| cgg | gtc | atc | ttc | tta | gaa | gat | gat | gat | atc | gct | gca | gtg | gct gat ggg | 864 |
| Arg | Val | Ile | Phe | Leu | Glu | Asp | Asp | Asp | Ile | Ala | Ala | Val | Ala Asp Gly | |
| | | 275 | | | | | 280 | | | | | 285 | | |

| aaa | ctc | tcc | att | cac | cga | gtc | aag | cgc | tca | gct | act | gat | gac ccc tcc | 912 |
| Lys | Leu | Ser | Ile | His | Arg | Val | Lys | Arg | Ser | Ala | Thr | Asp | Asp Pro Ser | |
| 290 | | | | | 295 | | | | | 300 | | | | |

| cga | gcc | atc | cag | acc | ttg | cag | atg | gaa | ctg | cag | caa | ata | atg aaa ggt | 960 |
| Arg | Ala | Ile | Gln | Thr | Leu | Gln | Met | Glu | Leu | Gln | Gln | Ile | Met Lys Gly | |
| 305 | | | | | 310 | | | | | 315 | | | | 320 |

| aac | ttc | agc | gca | ttt | atg | cag | aag | gag | atc | ttc | gag | cag | cca gaa tca | 1008 |
| Asn | Phe | Ser | Ala | Phe | Met | Gln | Lys | Glu | Ile | Phe | Glu | Gln | Pro Glu Ser | |
| | | | | 325 | | | | | 330 | | | | 335 | |

| gtt | ttt | aat | acc | atg | aga | ggt | cgg | gtg | aat | ttt | gag | acc | aac aca gtg | 1056 |
| Val | Phe | Asn | Thr | Met | Arg | Gly | Arg | Val | Asn | Phe | Glu | Thr | Asn Thr Val | |
| | | | 340 | | | | | 345 | | | | 350 | | |

```
ctc ctg ggt ggc ttg aag gac cat ttg aaa gag atc cga cga tgc cga   1104
Leu Leu Gly Gly Leu Lys Asp His Leu Lys Glu Ile Arg Arg Cys Arg
        355                 360                 365 agg ctc att gtg att ggc tgt gga acc agc tac cat gcc gct gtg gct   1152
Arg Leu Ile Val Ile Gly Cys Gly Thr Ser Tyr His Ala Ala Val Ala
    370                 375                 380 aca cgg caa gtc tta gag gaa ctg acc gag ctg cct gtg atg gtt gaa   1200
Thr Arg Gln Val Leu Glu Glu Leu Thr Glu Leu Pro Val Met Val Glu
385                 390                 395                 400 ctt gcc agt gac ttt ctg gac agg aac aca cct gtg ttc agg gat gac   1248
Leu Ala Ser Asp Phe Leu Asp Arg Asn Thr Pro Val Phe Arg Asp Asp
                405                 410                 415 gtt tgc ttt ttc ata agc caa tca ggt gag act gca gac acg ctc ctg   1296
Val Cys Phe Phe Ile Ser Gln Ser Gly Glu Thr Ala Asp Thr Leu Leu
            420                 425                 430 gcg ctg cga tac tgt aag gat cga ggt gcg ctg acc gtg ggc atc acc   1344
Ala Leu Arg Tyr Cys Lys Asp Arg Gly Ala Leu Thr Val Gly Ile Thr
        435                 440                 445 aac acc gtg ggt agc tcc atc tcc cgg gag act gac tgt ggc gtc cac   1392
Asn Thr Val Gly Ser Ser Ile Ser Arg Glu Thr Asp Cys Gly Val His
450                 455                 460 atc aac gca ggg ccc gag att ggg gtg gcc agc acc aag gcg tac acc   1440
Ile Asn Ala Gly Pro Glu Ile Gly Val Ala Ser Thr Lys Ala Tyr Thr
465                 470                 475                 480 agc cag ttc atc tct ctg gtg atg ttt ggt ttg atg atg tct gaa gat   1488
Ser Gln Phe Ile Ser Leu Val Met Phe Gly Leu Met Met Ser Glu Asp
                485                 490                 495 cga att tct cta cag aac agg aga caa gag atc atc cgt ggc ctc aga   1536
Arg Ile Ser Leu Gln Asn Arg Arg Gln Glu Ile Ile Arg Gly Leu Arg
            500                 505                 510 tct tta ccg gag ctg atc aaa gaa gtg ctg tcc ctg gat gag aag atc   1584
Ser Leu Pro Glu Leu Ile Lys Glu Val Leu Ser Leu Asp Glu Lys Ile
        515                 520                 525 cat gac ttg gcc ctg gag ctc tac aca caa agg tct ctc ctc gtg atg   1632
His Asp Leu Ala Leu Glu Leu Tyr Thr Gln Arg Ser Leu Leu Val Met
    530                 535                 540 gga cgg gga tat aac tat gcc aca tgt ctg gaa ggt gcc ttg aaa att   1680
Gly Arg Gly Tyr Asn Tyr Ala Thr Cys Leu Glu Gly Ala Leu Lys Ile
545                 550                 555                 560 aag gag ata acc tac atg cat tca gaa ggt atc cta gcc gga gag ctg   1728
Lys Glu Ile Thr Tyr Met His Ser Glu Gly Ile Leu Ala Gly Glu Leu
                565                 570                 575 aag cac ggg ccc ctt gct ctc gtc gac aag cag atg cca gtc atc atg   1776
Lys His Gly Pro Leu Ala Leu Val Asp Lys Gln Met Pro Val Ile Met
            580                 585                 590 gtc atc atg aag gat cct tgc ttt gcc aag tgc cag aat gcc ctg cag   1824
Val Ile Met Lys Asp Pro Cys Phe Ala Lys Cys Gln Asn Ala Leu Gln
        595                 600                 605 cag gtc act gcc cgc cag ggt cgc cca atc ata ctg tgt tcc aag gat   1872
Gln Val Thr Ala Arg Gln Gly Arg Pro Ile Ile Leu Cys Ser Lys Asp
    610                 615                 620 gac acc gag agc tcc aag ttt gca tat aaa acc att gaa ctt ccc cac   1920
Asp Thr Glu Ser Ser Lys Phe Ala Tyr Lys Thr Ile Glu Leu Pro His
625                 630                 635                 640 aca gtg gac tgt ctc cag ggt atc ctg agc gtg att cca ctc cag ctt   1968
Thr Val Asp Cys Leu Gln Gly Ile Leu Ser Val Ile Pro Leu Gln Leu
                645                 650                 655 ctg tcc ttc cac ctg gct gtc ctc cga ggt tat gat gtt gac ttc ccc   2016
Leu Ser Phe His Leu Ala Val Leu Arg Gly Tyr Asp Val Asp Phe Pro
            660                 665                 670
```

```
aga aac cta gcc aag tct gtc act gtg gaa tga                    2049
Arg Asn Leu Ala Lys Ser Val Thr Val Glu
        675                 680

<210> SEQ ID NO 7
<211> LENGTH: 682
<212> TYPE: PRT
<213> ORGANISM: Mus musculus

<400> SEQUENCE: 7

Met Cys Gly Ile Phe Ala Tyr Met Asn Tyr Arg Val Pro Lys Thr Arg
1               5                   10                  15

Lys Glu Ile Phe Glu Thr Leu Ile Arg Gly Leu Gln Arg Leu Glu Tyr
            20                  25                  30

Arg Gly Tyr Asp Ser Ala Gly Val Ala Ile Asp Gly Asn Asn His Glu
        35                  40                  45

Val Lys Glu Arg His Ile His Leu Val Lys Arg Gly Lys Val Lys
50                  55                  60

Ala Leu Asp Glu Glu Leu Tyr Lys Gln Asp Ser Met Asp Leu Lys Val
65                  70                  75                  80

Glu Phe Glu Thr His Phe Gly Ile Ala His Thr Arg Trp Ala Thr His
            85                  90                  95

Gly Val Pro Asn Ala Val Asn Ser His Pro Gln Arg Ser Asp Lys Asp
            100                 105                 110

Asn Glu Phe Val Val Ile His Asn Gly Ile Ile Thr Asn Tyr Lys Asp
        115                 120                 125

Leu Arg Lys Phe Leu Glu Ser Lys Gly Tyr Glu Phe Glu Ser Glu Thr
130                 135                 140

Asp Thr Glu Thr Ile Ala Lys Leu Ile Lys Tyr Val Phe Asp Asn Arg
145                 150                 155                 160

Glu Thr Glu Asp Ile Thr Phe Ser Thr Leu Val Glu Arg Val Ile Gln
            165                 170                 175

Gln Leu Glu Gly Ala Phe Ala Leu Val Phe Lys Ser Ile His Tyr Pro
        180                 185                 190

Gly Glu Ala Val Ala Thr Arg Arg Gly Ser Pro Leu Leu Ile Gly Val
        195                 200                 205

Arg Ser Lys Tyr Lys Leu Ser Thr Glu Gln Ile Pro Val Leu Tyr Pro
210                 215                 220

Thr Cys Asn Ile Glu Asn Val Lys Asn Ile Cys Lys Thr Arg Met Lys
225                 230                 235                 240

Arg Leu Asp Ser Ser Thr Cys Leu His Ala Val Gly Asp Lys Ala Val
            245                 250                 255

Glu Phe Phe Phe Ala Ser Asp Ala Ser Ala Ile Ile Glu His Thr Asn
        260                 265                 270

Arg Val Ile Phe Leu Glu Asp Asp Ile Ala Ala Val Ala Asp Gly
        275                 280                 285

Lys Leu Ser Ile His Arg Val Lys Arg Ser Ala Thr Asp Asp Pro Ser
290                 295                 300

Arg Ala Ile Gln Thr Leu Gln Met Glu Leu Gln Gln Ile Met Lys Gly
305                 310                 315                 320

Asn Phe Ser Ala Phe Met Gln Lys Glu Ile Phe Glu Gln Pro Glu Ser
            325                 330                 335

Val Phe Asn Thr Met Arg Gly Arg Val Asn Phe Glu Thr Asn Thr Val
        340                 345                 350

Leu Leu Gly Gly Leu Lys Asp His Leu Lys Glu Ile Arg Arg Cys Arg
```

-continued

```
                355                 360                 365
Arg Leu Ile Val Ile Gly Cys Gly Thr Ser Tyr His Ala Ala Val Ala
    370                 375                 380

Thr Arg Gln Val Leu Glu Glu Leu Thr Glu Leu Pro Val Met Val Glu
385                 390                 395                 400

Leu Ala Ser Asp Phe Leu Asp Arg Asn Thr Pro Val Phe Arg Asp Asp
                405                 410                 415

Val Cys Phe Phe Ile Ser Gln Ser Gly Glu Thr Ala Asp Thr Leu Leu
            420                 425                 430

Ala Leu Arg Tyr Cys Lys Asp Arg Gly Ala Leu Thr Val Gly Ile Thr
        435                 440                 445

Asn Thr Val Gly Ser Ser Ile Ser Arg Glu Thr Asp Cys Gly Val His
    450                 455                 460

Ile Asn Ala Gly Pro Glu Ile Gly Val Ala Ser Thr Lys Ala Tyr Thr
465                 470                 475                 480

Ser Gln Phe Ile Ser Leu Val Met Phe Gly Leu Met Met Ser Glu Asp
                485                 490                 495

Arg Ile Ser Leu Gln Asn Arg Gln Glu Ile Ile Arg Gly Leu Arg
            500                 505                 510

Ser Leu Pro Glu Leu Ile Lys Glu Val Leu Ser Leu Asp Glu Lys Ile
        515                 520                 525

His Asp Leu Ala Leu Glu Leu Tyr Thr Gln Arg Ser Leu Leu Val Met
    530                 535                 540

Gly Arg Gly Tyr Asn Tyr Ala Thr Cys Leu Glu Gly Ala Leu Lys Ile
545                 550                 555                 560

Lys Glu Ile Thr Tyr Met His Ser Glu Gly Ile Leu Ala Gly Glu Leu
                565                 570                 575

Lys His Gly Pro Leu Ala Leu Val Asp Lys Gln Met Pro Val Ile Met
            580                 585                 590

Val Ile Met Lys Asp Pro Cys Phe Ala Lys Cys Gln Asn Ala Leu Gln
        595                 600                 605

Gln Val Thr Ala Arg Gln Gly Arg Pro Ile Ile Leu Cys Ser Lys Asp
    610                 615                 620

Asp Thr Glu Ser Ser Lys Phe Ala Tyr Lys Thr Ile Glu Leu Pro His
625                 630                 635                 640

Thr Val Asp Cys Leu Gln Gly Ile Leu Ser Val Ile Pro Leu Gln Leu
                645                 650                 655

Leu Ser Phe His Leu Ala Val Leu Arg Gly Tyr Asp Val Asp Phe Pro
            660                 665                 670

Arg Asn Leu Ala Lys Ser Val Thr Val Glu
        675                 680
```

<210> SEQ ID NO 8
<211> LENGTH: 1830
<212> TYPE: DNA
<213> ORGANISM: Escherichia coli
<220> FEATURE:
<221> NAME/KEY: CDS
<222> LOCATION: (1)..(1827)
<300> PUBLICATION INFORMATION:
<308> DATABASE ACCESSION NUMBER: U00096.2
<309> DATABASE ENTRY DATE: 2005-09-08
<313> RELEVANT RESIDUES IN SEQ ID NO: (3909862)..(3911691)

<400> SEQUENCE: 8

```
atg tgt gga att gtt ggc gcg atc gcg caa cgt gat gta gca gaa atc      48
Met Cys Gly Ile Val Gly Ala Ile Ala Gln Arg Asp Val Ala Glu Ile
1               5                   10                  15
```

```
ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
         20              25              30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
             35              40              45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
     50              55              60 cat ggc ggc act ggt att gct cac act cgc tgg gcg acc cac ggt gaa     240
His Gly Gly Thr Gly Ile Ala His Thr Arg Trp Ala Thr His Gly Glu
65              70              75              80 cct tca gaa gtg aat gcg cat ccg cat gtt tct gaa cac att gtg gtg     288
Pro Ser Glu Val Asn Ala His Pro His Val Ser Glu His Ile Val Val
             85              90              95 gtg cat aac ggc atc atc gaa aac cat gaa ccg ctg cgt gaa gag cta     336
Val His Asn Gly Ile Ile Glu Asn His Glu Pro Leu Arg Glu Glu Leu
        100             105             110 aaa gcg cgt ggc tat acc ttc gtt tct gaa acc gac acc gaa gtg att     384
Lys Ala Arg Gly Tyr Thr Phe Val Ser Glu Thr Asp Thr Glu Val Ile
         115             120             125 gcc cat ctg gtg aac tgg gag ctg aaa caa ggc ggg act ctg cgt gag     432
Ala His Leu Val Asn Trp Glu Leu Lys Gln Gly Gly Thr Leu Arg Glu
     130             135             140 gcc gtt ctg cgt gct atc ccg cag ctg cgt ggt gcg tac ggt aca gtg     480
Ala Val Leu Arg Ala Ile Pro Gln Leu Arg Gly Ala Tyr Gly Thr Val
145             150             155             160 atc atg gac tcc cgt cac ccg gat acc ctg ctg gcg gca cgt tct ggt     528
Ile Met Asp Ser Arg His Pro Asp Thr Leu Leu Ala Ala Arg Ser Gly
             165             170             175 agt ccg ctg gtg att ggc ctg ggg atg ggc gaa aac ttt atc gct tct     576
Ser Pro Leu Val Ile Gly Leu Gly Met Gly Glu Asn Phe Ile Ala Ser
        180             185             190 gac cag ctg gcg ctg ttg ccg gtg acc cgt cgc ttt atc ttc ctt gaa     624
Asp Gln Leu Ala Leu Leu Pro Val Thr Arg Arg Phe Ile Phe Leu Glu
         195             200             205 gag ggc gat att gcg gaa atc act cgc cgt tcg gta aac atc ttc gat     672
Glu Gly Asp Ile Ala Glu Ile Thr Arg Arg Ser Val Asn Ile Phe Asp
     210             215             220 aaa act ggc gcg gaa gta aaa cgt cag gat atc gaa tcc aat ctg caa     720
Lys Thr Gly Ala Glu Val Lys Arg Gln Asp Ile Glu Ser Asn Leu Gln
225             230             235             240 tat gac gcg ggc gat aaa ggc att tac cgt cac tac atg cag aaa gag     768
Tyr Asp Ala Gly Asp Lys Gly Ile Tyr Arg His Tyr Met Gln Lys Glu
             245             250             255 atc tac gaa cag ccg aac gcg atc aaa aac acc ctt acc gga cgc atc     816
Ile Tyr Glu Gln Pro Asn Ala Ile Lys Asn Thr Leu Thr Gly Arg Ile
        260             265             270 agc cac ggt cag gtt gat tta agc gag ctg gga ccg aac gcc gac gaa     864
Ser His Gly Gln Val Asp Leu Ser Glu Leu Gly Pro Asn Ala Asp Glu
         275             280             285 ctg ctg tcg aag gtt gag cat att cag atc ctc gcc tgt ggt act tct     912
Leu Leu Ser Lys Val Glu His Ile Gln Ile Leu Ala Cys Gly Thr Ser
     290             295             300 tat aac tcc ggt atg gtt tcc cgc tac tgg ttt gaa tcg cta gca ggt     960
Tyr Asn Ser Gly Met Val Ser Arg Tyr Trp Phe Glu Ser Leu Ala Gly
305             310             315             320 att ccg tgc gac gtc gaa atc gcc tct gaa ttc cgc tat cgc aaa tct    1008
Ile Pro Cys Asp Val Glu Ile Ala Ser Glu Phe Arg Tyr Arg Lys Ser
             325             330             335
```

```
gcc gtg cgt cgt aac agc ctg atg atc acc ttg tca cag tct ggc gaa     1056
Ala Val Arg Arg Asn Ser Leu Met Ile Thr Leu Ser Gln Ser Gly Glu
        340                 345                 350 acc gcg gat acc ctg gct ggc ctg cgt ctg tcg aaa gag ctg ggt tac     1104
Thr Ala Asp Thr Leu Ala Gly Leu Arg Leu Ser Lys Glu Leu Gly Tyr
                355                 360                 365 ctt ggt tca ctg gca atc tgt aac gtt ccg ggt tct tct ctg gtg cgc     1152
Leu Gly Ser Leu Ala Ile Cys Asn Val Pro Gly Ser Ser Leu Val Arg
370                 375                 380 gaa tcc gat ctg gcg cta atg acc aac gcg ggt aca gaa atc ggc gtg     1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg     1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat     1296
Val Ala Lys Leu Ser Arg Leu Lys Gly Leu Asp Ala Ser Ile Glu His
                420                 425                 430 gac atc gtg cat ggt ctg cag gcg ctg ccg agc cgt att gag cag atg     1344
Asp Ile Val His Gly Leu Gln Ala Leu Pro Ser Arg Ile Glu Gln Met
            435                 440                 445 ctg tct cag gac aaa cgc att gaa gcg ctg gca gaa gat ttc tct gac     1392
Leu Ser Gln Asp Lys Arg Ile Glu Ala Leu Ala Glu Asp Phe Ser Asp
450                 455                 460 aaa cat cac gcg ctg ttc ctg ggc cgt ggc gat cag tac cca atc gcg     1440
Lys His His Ala Leu Phe Leu Gly Arg Gly Asp Gln Tyr Pro Ile Ala
465                 470                 475                 480 ctg gaa ggc gca ttg aag ttg aaa gag atc tct tac att cac gct gaa     1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat     1536
Ala Tyr Ala Ala Gly Glu Leu Lys His Gly Pro Leu Ala Leu Ile Asp
                500                 505                 510 gcc gat atg ccg gtt att gtt gtt gca ccg aac aac gaa ttg ctg gaa     1584
Ala Asp Met Pro Val Ile Val Val Ala Pro Asn Asn Glu Leu Leu Glu
            515                 520                 525 aaa ctg aaa tcc aac att gaa gaa gtt cgc gcg cgt ggc ggt cag ttg     1632
Lys Leu Lys Ser Asn Ile Glu Glu Val Arg Ala Arg Gly Gly Gln Leu
530                 535                 540 tat gtc ttc gcc gat cag gat gcg ggt ttt gta agt agc gat aac atg     1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc     1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa     1776
Tyr Thr Val Pro Leu Gln Leu Leu Ala Tyr His Val Ala Leu Ile Lys
                580                 585                 590 ggc acc gac gtt gac cag ccg cgt aac ctg gca aaa tcg gtt acg gtt     1824
Gly Thr Asp Val Asp Gln Pro Arg Asn Leu Ala Lys Ser Val Thr Val
            595                 600                 605 gag taa                                                              1830
Glu

<210> SEQ ID NO 9
<211> LENGTH: 609
<212> TYPE: PRT
<213> ORGANISM: Escherichia coli

<400> SEQUENCE: 9
```

-continued

```
Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
                100                 105                 110

Lys Ala Arg Gly Tyr Thr Phe Val Ser Glu Thr Asp Thr Glu Val Ile
            115                 120                 125

Ala His Leu Val Asn Trp Glu Leu Lys Gln Gly Gly Thr Leu Arg Glu
        130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
        290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
    370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430
```

```
Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 10
<211> LENGTH: 1830
<212> TYPE: DNA
<213> ORGANISM: Artificial Sequence
<220> FEATURE:
<223> OTHER INFORMATION: Synthetic sequence encoding an Escherichia coli
      protein having the activity of a GFAT

<400> SEQUENCE: 10
atgtgcggaa ttgttggtgc tatcgcccaa agagacgttg ctgagatttt gttagagggt      60
ctgcgaaggc tagagtatag aggatatgac tccgctggtc tggctgtcgt tgatgctgag     120
ggtcatatga caaggctaag aaggttagga aaggttcaga tgcttgctca ggcagctgag     180
gaacatccat tgcatggagg tactggtatt gcacatacca ggtgggctac tcatggggag     240
ccatcagaag ttaatgctca tccacatgtg agtgagcata tcgttgtagt tcacaatggg     300
ataattgaaa accacgaacc attgagggaa gagttaaagg caagaggata tacttttgtg     360
agtgagactg acactgaggt tattgcacat ttagtgaact gggaactcaa acagggggc      420 acattgcgtg aggctgtgtt aagagctatt cctcaactta gaggtgcata cggtactgtt     480
attatggatt caagacaccc agatactctc cttgcagcta gatcaggtag tcccttggtc     540
ataggacttg aatgggtgaa aatttatc gctagcgacc aattggcctt attgccagtt      600
acaagacgat ttattttcct tgaagagggc gatattgctg agattactag aaggtctgtg     660
aacatctttg ataagactgg cgctgaggtt aaacgtcagg atatcgagtc taaccttcaa     720
tacgatgctg gtgataaagg aatttacagg cattatatgc aaaaggaaat ttatgaacaa     780
ccaaatgcta tcaaaaacac acttactggc cgtatttctc atggacaggt cgatttaagc     840
gagcttggtc ctaatgcaga cgaactgcta tcaaaagttg agcacataca gatactggca     900
tgcggaacta gttataattc aggaatggtc tctagatact ggttcgaaag cttggcaggt     960 atacctgtg atgtagagat cgcttctgag tttaggtata gaaagtctgc tgtgcgtaga    1020
```

```
aattcattaa tgattacatt atctcaatcc ggagaaacag cagatacact ggctggattg    1080
aggctttcta aggaactcgg atatctgggt tcacttgcta tttgtaatgt accaggttcc    1140
tcattggttc gtgaatcaga tctagcactt atgacaaatg caggaactga ataggtgtg     1200 gcaagtacca aggctttcac aacccaactg accgtacttt taatgttggt agcaaaactc    1260
agtcgattaa aggggctaga tgcatctatc gaacatgata ttgttcacgg gcttcaagct    1320
ctcccttcaa gaattgaaca aatgcttcca caagataaga gaatagaggc attggctgaa    1380 gattttccg acaaacatca cgcattgttt cttggacgtg gcgatcaata tccaattgca     1440
ttggaaggag ctttgaagtt gaaagaaata agttacattc acgcagaagc atatgcagct    1500
ggagaactca agcatggtcc tttggcactc atcgacgctg acatgcccgt gatcgtagtg    1560
gctcctaata acgaactgct cgaaaagctt aaatcaaata tcgaagaggt tcgagctaga    1620
ggaggtcagc tttacgtttt cgctgaacaa gatgctggat tcgtgtcaag cgataatatg    1680
catataattg aaatgcctca cgttgaagaa gtgattgcac ctatatttta tacagtccca    1740
ttgcaacttc tagcttacca tgttgcactt attaaaggaa ctgatgttga tcagcctaga    1800
aacctagcaa aatctgtaac agtcgaataa                                     1830

<210> SEQ ID NO 11
<211> LENGTH: 1260
<212> TYPE: DNA
<213> ORGANISM: Paramecium bursaria Chlorella Virus 1
<220> FEATURE:
<221> NAME/KEY: CDS
<222> LOCATION: (62)..(1228)
<300> PUBLICATION INFORMATION:
<308> DATABASE ACCESSION NUMBER: U42580.4
<309> DATABASE ENTRY DATE: 2004-09-20
<313> RELEVANT RESIDUES IN SEQ ID NO: (291749.)..(292918)

<400> SEQUENCE: 11
atcaacgtga tttatatttt aaacaaagac cattcacatc tttagtactt aattaattat    60 a atg tca cga atc gca gtc gtt ggt tgt ggt tac gtc gga acc gct tgt   109
  Met Ser Arg Ile Ala Val Val Gly Cys Gly Tyr Val Gly Thr Ala Cys
  1               5                  10                  15 gca gta ctt ctt gct caa aaa aac gaa gtc atc gtg ctt gat att agc    157
Ala Val Leu Leu Ala Gln Lys Asn Glu Val Ile Val Leu Asp Ile Ser
             20                  25                  30 gaa gac cgt gtt caa cta atc aag aac aag aag agt cca atc gag gac    205
Glu Asp Arg Val Gln Leu Ile Lys Asn Lys Lys Ser Pro Ile Glu Asp
 35                  40                  45 aag gaa atc gaa gag ttt ctc gaa acg aaa gac ctg aac ctg acc gcg    253
Lys Glu Ile Glu Glu Phe Leu Glu Thr Lys Asp Leu Asn Leu Thr Ala
     50                  55                  60 acg act gac aag gtt ctt gca tac gaa aac gcc gaa ttt gtc atc atc    301
Thr Thr Asp Lys Val Leu Ala Tyr Glu Asn Ala Glu Phe Val Ile Ile
65                  70                  75                  80 gca acc ccg act gac tat gac gtg gtt act agg tat ttt aac acg aaa    349
Ala Thr Pro Thr Asp Tyr Asp Val Val Thr Arg Tyr Phe Asn Thr Lys
                 85                  90                  95 tct gtg gaa aac gtc att ggg gac gtg atc aaa aat aca cag acc cat    397
Ser Val Glu Asn Val Ile Gly Asp Val Ile Lys Asn Thr Gln Thr His
            100                 105                 110 cca act atc gtg att aaa tct acc atc ccc att gga ttt gtt gat aag    445
Pro Thr Ile Val Ile Lys Ser Thr Ile Pro Ile Gly Phe Val Asp Lys
        115                 120                 125 gtt cgt gag caa ttc gac tac caa aat atc att ttc tcc cca gaa ttt    493
Val Arg Glu Gln Phe Asp Tyr Gln Asn Ile Ile Phe Ser Pro Glu Phe
```

```
ctg cgt gaa ggt aga gcc ttg tat gat aat ctc tac cca tcc cgt atc       541
Leu Arg Glu Gly Arg Ala Leu Tyr Asp Asn Leu Tyr Pro Ser Arg Ile
145                 150                 155                 160 atc gta gga gat gat tcc ccc att gcg ctt aag ttc gca aac ctt ctc       589
Ile Val Gly Asp Asp Ser Pro Ile Ala Leu Lys Phe Ala Asn Leu Leu
                165                 170                 175 gtt gaa ggt tct aaa act ccg ctt gcc cct gtc ctg acg atg gga act       637
Val Glu Gly Ser Lys Thr Pro Leu Ala Pro Val Leu Thr Met Gly Thr
            180                 185                 190 cgc gaa gcc gag gcc gtc aaa cta ttc tct aac acg tat ctt gca atg       685
Arg Glu Ala Glu Ala Val Lys Leu Phe Ser Asn Thr Tyr Leu Ala Met
        195                 200                 205 cga gtt gca tac ttc aac gaa cta gat aca ttc gca atg tct cac ggt       733
Arg Val Ala Tyr Phe Asn Glu Leu Asp Thr Phe Ala Met Ser His Gly
    210                 215                 220 atg aat gcg aaa gaa atc att gat ggt gtg act ctg gag cct cgc att       781
Met Asn Ala Lys Glu Ile Ile Asp Gly Val Thr Leu Glu Pro Arg Ile
225                 230                 235                 240 ggt cag ggg tac tca aac cct tcg ttc ggt tat gga gct tat tgc ttt       829
Gly Gln Gly Tyr Ser Asn Pro Ser Phe Gly Tyr Gly Ala Tyr Cys Phe
                245                 250                 255 cca aag gat acg aag caa ctg ctg gct aat ttc gag gga gtg cct caa       877
Pro Lys Asp Thr Lys Gln Leu Leu Ala Asn Phe Glu Gly Val Pro Gln
            260                 265                 270 gat atc atc gga gca att gta gaa tca aat gag act cgc aag gaa gtg       925
Asp Ile Ile Gly Ala Ile Val Glu Ser Asn Glu Thr Arg Lys Glu Val
        275                 280                 285 att gtg agt gaa gta gaa aat cgt ttc ccc acg act gtt ggt gtg tat       973
Ile Val Ser Glu Val Glu Asn Arg Phe Pro Thr Thr Val Gly Val Tyr
    290                 295                 300 aag ctc gcc gct aaa gcg ggt tct gat aat ttt cgg agt tct gca att      1021
Lys Leu Ala Ala Lys Ala Gly Ser Asp Asn Phe Arg Ser Ser Ala Ile
305                 310                 315                 320 gta gac ata atg gag cga ctt gca aac aag ggt tat cac att aag att      1069
Val Asp Ile Met Glu Arg Leu Ala Asn Lys Gly Tyr His Ile Lys Ile
                325                 330                 335 ttc gaa cca act gtg gaa caa ttc gaa aac ttt gaa gtt gat aac aac      1117
Phe Glu Pro Thr Val Glu Gln Phe Glu Asn Phe Glu Val Asp Asn Asn
            340                 345                 350 ctg aca aca ttt gcg act gag agc gat gta att atc gca aac aga gtt      1165
Leu Thr Thr Phe Ala Thr Glu Ser Asp Val Ile Ile Ala Asn Arg Val
        355                 360                 365 ccc gtt gaa cat cgc att ctc ttt ggt aaa aaa tta atc aca cgt gat      1213
Pro Val Glu His Arg Ile Leu Phe Gly Lys Lys Leu Ile Thr Arg Asp
    370                 375                 380 gta tat ggc gat aac taaaatgttt tcaatatgat gttgttaatg at             1260
Val Tyr Gly Asp Asn
385

<210> SEQ ID NO 12
<211> LENGTH: 389
<212> TYPE: PRT
<213> ORGANISM: Paramecium bursaria Chlorella Virus 1

<400> SEQUENCE: 12

Met Ser Arg Ile Ala Val Val Gly Cys Gly Tyr Val Gly Thr Ala Cys
1               5                   10                  15

Ala Val Leu Leu Ala Gln Lys Asn Glu Val Ile Val Leu Asp Ile Ser
            20                  25                  30
```

Glu Asp Arg Val Gln Leu Ile Lys Asn Lys Ser Pro Ile Glu Asp
             35                  40                  45

Lys Glu Ile Glu Glu Phe Leu Glu Thr Lys Asp Leu Asn Leu Thr Ala
 50                  55                  60

Thr Thr Asp Lys Val Leu Ala Tyr Glu Asn Ala Glu Phe Val Ile Ile
 65                  70                  75                  80

Ala Thr Pro Thr Asp Tyr Asp Val Val Thr Arg Tyr Phe Asn Thr Lys
                 85                  90                  95

Ser Val Glu Asn Val Ile Gly Asp Val Ile Lys Asn Thr Gln Thr His
             100                 105                 110

Pro Thr Ile Val Ile Lys Ser Thr Ile Pro Ile Gly Phe Val Asp Lys
         115                 120                 125

Val Arg Glu Gln Phe Asp Tyr Gln Asn Ile Ile Phe Ser Pro Glu Phe
130                 135                 140

Leu Arg Glu Gly Arg Ala Leu Tyr Asp Asn Leu Tyr Pro Ser Arg Ile
145                 150                 155                 160

Ile Val Gly Asp Asp Ser Pro Ile Ala Leu Lys Phe Ala Asn Leu Leu
                165                 170                 175

Val Glu Gly Ser Lys Thr Pro Leu Ala Pro Val Leu Thr Met Gly Thr
            180                 185                 190

Arg Glu Ala Glu Ala Val Lys Leu Phe Ser Asn Thr Tyr Leu Ala Met
195                 200                 205

Arg Val Ala Tyr Phe Asn Glu Leu Asp Thr Phe Ala Met Ser His Gly
210                 215                 220

Met Asn Ala Lys Glu Ile Ile Asp Gly Val Thr Leu Glu Pro Arg Ile
225                 230                 235                 240

Gly Gln Gly Tyr Ser Asn Pro Ser Phe Gly Tyr Gly Ala Tyr Cys Phe
                245                 250                 255

Pro Lys Asp Thr Lys Gln Leu Leu Ala Asn Phe Glu Gly Val Pro Gln
            260                 265                 270

Asp Ile Ile Gly Ala Ile Val Glu Ser Asn Glu Thr Arg Lys Glu Val
        275                 280                 285

Ile Val Ser Glu Val Glu Asn Arg Phe Pro Thr Thr Val Gly Val Tyr
290                 295                 300

Lys Leu Ala Ala Lys Ala Gly Ser Asp Asn Phe Arg Ser Ser Ala Ile
305                 310                 315                 320

Val Asp Ile Met Glu Arg Leu Ala Asn Lys Gly Tyr His Ile Lys Ile
                325                 330                 335

Phe Glu Pro Thr Val Glu Gln Phe Asn Phe Glu Val Asp Asn Asn
            340                 345                 350

Leu Thr Thr Phe Ala Thr Glu Ser Asp Val Ile Ile Ala Asn Arg Val
        355                 360                 365

Pro Val Glu His Arg Ile Leu Phe Gly Lys Lys Leu Ile Thr Arg Asp
370                 375                 380

Val Tyr Gly Asp Asn
385

<210> SEQ ID NO 13
<211> LENGTH: 1170
<212> TYPE: DNA
<213> ORGANISM: Artificial Sequence
<220> FEATURE:
<223> OTHER INFORMATION: Synthetic sequence encoding a Paramecium
      bursaria Chlorella Virus protein having the activity of a
      UDP-Glc-DH

<400> SEQUENCE: 13

```
atgtctcgca tagctgttgt aggatgtggc tatgtgggaa ctgcatgtgc ggttctactt    60
gctcaaaaga acgaagttat tgtgcttgat attagtgaag accgtgttca acttattaag   120
aacaagaagt ctcctattga ggataaggaa atcgaagagt tcttggaaac aaaggatctt   180
aatcttactg cgactacaga taaggttctt gcctacgaga acgctgagtt tgtgataatc   240
gctacaccaa ccgattacga cgttgtgact cgatatttca ataccaaatc cgtggaaaac   300
gttataggag atgttatcaa gaacactcaa acccacccta ctatcgtcat caagtccaca   360
attcccatcg gtttcgttga taaggtcaga gagcagtttg attatcaaaa cattatcttc   420
tcacctgagt tcttaaggga gggtcgtgct ctctacgata atttgtatcc gtcccgtatt   480
atcgttggcg acgattctcc tatcgctctc aagttcgcaa atctcttagt tgagggtagt   540
aagacccctt tggctcctgt tttgacaatg ggaaccagag aagcagaagc tgtcaagcta   600
ttctctaata cctaccttgc catgagggta gcatacttta cgaacttga tacatttgct    660 atgtcgcatg gtatgaatgc caaggagatt atagatggtg tcactttaga gcccaggatc   720
ggtcaaggat attctaaccc atcattcggc tatggagctt actgctttcc taaggacact   780
aagcagttgc tggcaaactt cgagggagtt cctcaagaca tcataggcgc tattgtggag   840
tcaaacgaaa caaggaaaga ggtgatagtt agtgaggtag agaatcgttt cccaacgaca   900
gtcggtgttt acaaactggc agctaaagct ggtagcgata cttcaggtc aagtgctatt    960 gtcgacatca tggaacgcct ggctaacaaa ggttaccaca ttaagatctt tgagccaact  1020
gtagagcagt cgaaaattt cgaagttgac aataacttga caacgtttgc tactgagtca   1080
gacgttatta tcgcaaatcg tgtccctgtg aacatagaa tcctatttgg aaagaagctc   1140
attaccagag atgtttacgg tgataattaa                                    1170

<210> SEQ ID NO 14
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 14
tcgacaggcc tggatcctta attaaactag tctcgaggag ctcggtac              48

<210> SEQ ID NO 15
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 15
cgagctcctc gagactagtt taattaagga tccaggcctg                       40

<210> SEQ ID NO 16
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 16
aaaaactagt tctacatcgg cttaggtgta gcaacacg                         38

<210> SEQ ID NO 17
<211> LENGTH: 39
```

-continued

```
<212> TYPE: DNA
<213> ORGANISM: Artificial Sequence
<220> FEATURE:
<223> OTHER INFORMATION: synthetic oligonucleotide

<400> SEQUENCE: 17
aaaagatatc tgttgttgga ttctactact atgcttcaa                          39
```